(12) United States Patent  
Ino et al.

(10) Patent No.: US 6,953,785 B2  
(45) Date of Patent: Oct. 11, 2005

(54) ESTRA-1,3,5(10)-TRIENE DERIVATIVES

(75) Inventors: Yoji Ino, Sunto-gun (JP); Nobuyoshi Amishiro, Champaign, IL (US); Mayumi Miyata, Chiyoda-ku (JP); Tsutomu Agatsuma, Machida (JP); Kozue Muramatsu, Sunto-gun (JP); Takeshi Takahashi, Sunto-gun (JP); Shiro Akinaga, Chiyoda-ku (JP); Chikara Murakata, Sunto-gun (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 182 days.

(21) Appl. No.: 10/258,454

(22) PCT Filed: Apr. 24, 2001

(86) PCT No.: PCT/JP01/03505

§ 371 (c)(1),
(2), (4) Date: Oct. 24, 2002

(87) PCT Pub. No.: WO01/81364

PCT Pub. Date: Jan. 11, 2001

(65) Prior Publication Data

US 2003/0216362 A1 Nov. 20, 2003

(30) Foreign Application Priority Data

Apr. 24, 2000 (JP) .................................. 2000-121960

(51) Int. Cl.[7] ........................ A61K 31/56; A61K 31/58; C07J 3/00; C07J 17/00; C07J 43/00
(52) U.S. Cl. ...................... 514/172; 514/176; 514/182; 540/107; 540/108; 540/109; 540/110; 540/114; 552/555; 552/558; 552/611
(58) Field of Search ................... 540/107, 108, 540/109, 110, 114; 552/555, 558, 611; 514/172, 176, 182

(56) References Cited

FOREIGN PATENT DOCUMENTS

| WO | 98/24802 | 6/1998 |
|----|----------|--------|
| WO | 99/27935 | 6/1999 |
| WO | 99/27936 | 6/1999 |
| WO | 99/33859 | 7/1999 |
| WO | 00/43408 | 7/2000 |
| WO | 00/53620 | 9/2000 |
| WO | 01/18028 | 3/2001 |

OTHER PUBLICATIONS

Holt, et al., "Steroidal A Ring Aryl Carboxylic Acids: A New Class of Steroid 5α–Reductase Inhibitors", J. Med. Chem., vol. 33 (1990), pp. 937–942.

Purohit, et al., "In Vivo Inhibition of Oestrone Sulphatase and . . . ", Int. J. Cancer, vol. 63 (1995), pp. 106–111.

Purohit, et al., "In Vivo Activity of 4–Methylcoumarin–7–O–Sulfamate, . . . ", Cancer Research, vol. 56 (1996) pp. 4950–4955.

Duncan, et al., "Inhibition of Estrone Sulfatase Activity by . . . ", Cancer Research, vol. 53 (1993), pp. 298–303.

Howarth, et al., "Phosphonates and Thiophosphonates as Sulfate Surrogates . . . ", Bioorganic & Medicinal Chemistry Letters, vol. 3, No. 2 (1993), pp. 313–318.

Howarth, et al., "Estrone Sulfamates: Potent Inhibitors of Estrone . . . ", J. Med. Chem, vol. 37 (1994), pp. 219–221.

Li, et al., "Synthesis and Biochemical Studies of Estrone Sulfatase Inhibitors", Steroids, vol. 58 (1993), pp. 106–111.

Dibbelt, et al., "Inhibition of Human Placental Sterylsulfatase by . . . ", J. Steroid Biochem. Molec. Biol., vol. 50 (1994), pp. 261–266.

Li, et al., "Estrone Sulfate Analogs as Estrone Sulfatase Inhibitors", Steroids, vol. 60 (1995), pp. 299–306.

Selcer, et al., "Inhibition of Placental Estrone Sulfatase Activity and . . . ", J. Steroid Biochem. Molec. Biol., vol. 59 (1996) pp. 83–91.

Evans, et al., "Lack of Inhibition of Placental Estrone Sulfatase and . . . ", J. Steroid Biochem. Molec. Biol., vol. 48, No. 5/6 (1994), pp. 563–566.

Santner, et al., "Inhibition of Estrone Sulfatase and . . . ", J. Steroid Biochem. Molec Biol., vol. 45, No. 5 (1993), pp. 383–390.

(Continued)

*Primary Examiner*—Barbara P. Badio
(74) *Attorney, Agent, or Firm*—Fitzpatrick, Cella, Harper & Scinto

(57) ABSTRACT

Provided is steroid sulfatase inhibitors comprising, as the active ingredient, an estra-1,3,5(10)-triene derivative which is represented by formula (I):

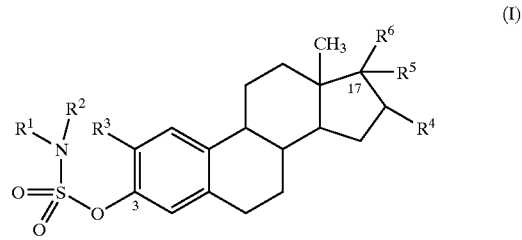

{wherein $R^1$ and $R^2$ are the same or different and represent a hydrogen atom, a lower alkyl group or, etc.; $R^3$ represents a hydrogen atom etc.; $R^4$ represents a hydrogen atom etc.; $R^5$ represents a hydrogen atom etc.; $R^6$ represents a cyano group, an amino group, $COR^{53}$ (wherein $R^{53}$ represents a substituted lower alkyl group etc.), a substituted or unsubstituted aryl group, a substituted or unsubstituted heterocyclic group, etc}, or pharmaceutically acceptable salts thereof.

21 Claims, No Drawings

OTHER PUBLICATIONS

Poirier, et al., "17α–Alkyl– or 17α–substituted Benzyl–17β–Estradiols: A New Family . . . ", Bioorganic & Medicinal Chemistry Letters, vol. 8 (1998), pp. 1891–1896.

Ciobanu, et al., "Potent Inhibition of Steroid Sulfatase . . . ", J. Med. Chem., vol. 42 (1999), pp. 2280–2286.

Römer, et al., "Scavestrogen Sulfamates: Correlation between Estrone . . . ", Can. J. Physiol. Pharmacol., vol. 76 (1998), pp. 99–109.

Li, et al., "Development of Potent Non–Estrogenic Estrone Sulfatase Inhibitors", Steroids, vol. 63 (1998), pp. 425–432.

Holt, et al., "Inhibition of Steroid 5α–Reductase by . . . ", J. Med. Chem., vol. 33 (1990), pp. 943–950.

Anderson, et al., "Estrone Sulfatase: Probing Structural Requirements for . . . ", Biochemistry, vol. 36 (1997), pp. 2586–2594.

Purohit, et al., "The Development of A–ring Modified Analogues . . . ", J. Steroid Biochem. Molec. Biol., vol. 64, No. 5–6 (1998), pp. 269–275.

ESTRA-1,3,5(10)-TRIENE DERIVATIVES

This application is a 371 of PCT/JP01/03505 filed Apr. 24, 2001.

TECHNICAL FIELD

The present invention relates to steroid sulfatase inhibitors comprising, as the active ingredient, an estra-1,3,5(10)-triene derivative or a pharmaceutically acceptable salt thereof. The present invention also relates to estra-1,3,5(10)-triene derivatives or pharmaceutically acceptable salts thereof that have inhibitory activity against steroid sulfatase and are useful for treating or preventing steroid hormone-dependent diseases.

BACKGROUND ART

In postmenopausal women, the estrogen level in breast cancer is at least 10 times higher than that in plasma, and it is considered that the high estrogen level in breast cancer is caused by hydrolysis of estrone sulfate into estrone by steroid sulfatase (estrone sulfatase). Therefore, steroid sulfatase inhibitors are considered to be effective therapeutic agents for treating estrone-dependent breast cancer, and they are also considered to be effective for preventing or treating other estrone-dependent diseases such as endometrial cancer, ovarian cancer, endometriosis and adenomyosis uteri. In addition, steroid sulfatase participates in androgen biosynthesis, and its inhibitors can also be effective for preventing or treating androgen-dependent diseases such as prostate cancer.

Estrone-3-sulfamate (EMATE) was reported to be a typical steroid sulfatase inhibitor [*International Journal of Cancer*, Vol. 63, p. 106 (1995); U.S. Pat. No. 5,616,574]. After that, however, it has been clarified that EMATE has an estrogenic effect, and it has been shown that EMATE is not useful for treatment of estrone-dependent diseases [*Cancer Research*, Vol. 56, p. 4950 (1996)]. Compounds with no estrogenic effect are desired as steroid sulfatase inhibitors.

As other steroid sulfatase inhibitors of steroid type, the following are known: estrone-3-methylthiophosphonate, estrone-3-methylphosphonate, estrone-3-phenylphosphonothioate, estrone-3-phenylphosphonate [*Cancer Research*, Vol. 53, p. 298 (1993); *Bioorganic & Medicinal Chemistry Letters*, Vol. 3, p. 313 (1993); U.S. Pat. No. 5,604,215]; estrone-3-sulfamate derivatives [*Journal of Medicinal Chemistry*, Vol. 37, p. 219 (1994)]; 3-desoxyestrone-3-sulfonate derivatives [*Steroids*, Vol. 58, p. 106 (1993); *The Journal of Steroid Biochemistry and Molecular Biology*, Vol. 50, p. 261 (1994)]; 3-desoxyestrone-3-methylsulfonate derivatives [*Steroids*, Vol. 60, p. 299 (1995)]; estrone-3-amino derivatives [*The Journal of Steroid Biochemistry and Molecular Biology*, Vol. 59, p. 83 (1996); U.S. Pat. No. 5,571,933, U.S. Pat. No. 5,866,603]; vitamin $D_3$ derivatives [*The Journal of Steroid Biochemistry and Molecular Biology*, Vol. 48, p. 563 (1994)]; dehydroepiandrosterone derivatives [*The Journal of Steroid Biochemistry and Molecular Biology*, Vol. 45, p. 383 (1993); *Biochemistry*, Vol. 36, p. 2586 (1997)]; A-ring modified derivatives of estrone-3-sulfamate [*The Journal of Steroid Biochemistry and Molecular Biology*, Vol. 64, p. 269 (1998); WO98/24802, WO98/32763]; 17-alkylestradiol derivatives [*Bioorganic & Medicinal Chemistry Letters*, Vol. 8, p. 1891 (1998); *Journal of Medicinal Chemistry*, Vol. 42, p. 2280 (1999)]; 3-substituted-D-homo-1,3,5,(10)-estratriene derivatives (WO98/11124, WO99/27935); D-ring modified derivatives of estrone (WO98/42729, WO99/27936); BCD-ring(s) modified derivatives of estrone [*Canadian Journal of Physiology and Pharmacology*, Vol. 76, p. 99 (1998)]; and 17β-(N-alkylcarbamoyl)-estra-1,3,5 (10)-triene-3-sulfamates and 17β-(N-alkanoylamino)-estra-1,3,5(10)-triene-3-sulfamates [*Steroids*, Vol. 63, p. 425 (1998); WO99/03876]. Recently, in addition, it has been reported that various estrone derivatives modified at 17-position have inhibitory activity against steroid sulfatase (WO99/33858).

On the other hand, as steroid sulfatase inhibitors of non-steroid type, the following are known: tetrahydronaphthol derivatives [*Journal of Medicinal Chemistry*, Vol. 37, p. 219 (1994)]; 4-methylcoumarin-7-sulfamate [*Cancer Research*, Vol. 56, p. 4950 (1996); WO97/30041]; tyramine derivatives and phenol derivatives [*Cancer Research*, Vol. 57, p. 702 (1997); *Biochemistry*, Vol. 36, p. 2586 (1997); *The Journal of Steroid Biochemistry and Molecular Biology*, Vol. 68, p. 31 (1999); U.S. Pat. No. 5,567,831]; flavonoids [*The Journal of Steroid Biochemistry and Molecular Biology*, Vol. 63, p. 9 (1997); WO97/32872]; 4-hydroxytamoxifen derivatives [*The Journal of Steroid Biochemistry and Molecular Biology*, Vol. 45, p. 383 (1993); *Bioorganic & Medicinal Chemistry Letters*, Vol. 9, p. 141 (1999)]; isoflavon derivatives [*The Journal of Steroid Biochemistry and Molecular Biology*, Vol. 69, p. 227 (1999)]; chromane derivatives (WO99/52890); etc.

It is also known that steroid sulfamates and tyramine derivatives have the effect of memory enhancement (U.S. Pat. No. 5,556,847, U.S. Pat. No. 5,763,492).

17-Amido derivatives (Compound A1) disclosed in WO99/03876 are limited to alkylcarbamoyl derivatives wherein an alkyl moiety has at least 4 carbon atoms and to alkanoylamino derivatives wherein an alkanoyl moiety has at least 5 carbon atoms, and it is believed that the long-chain alkyl group contained therein is important for their inhibitory activity against steroid sulfatase.

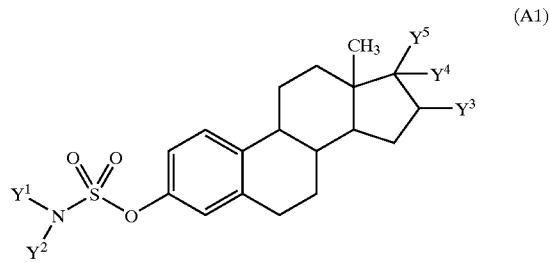

(A1)

[wherein $Y^1$ and $Y^2$ represent a hydrogen atom or a lower alkyl group; $Y^3$ represents a hydrogen atom, or forms a bond together with $Y^4$; $Y^4$ represents a hydrogen atom, or forms a bond together with $Y^3$; $Y^5$ represents $CONHY^6$ (wherein $Y^6$ represents a straight chain alkyl group having 4 to 14 carbon atoms), or $NHCOY^7$ (wherein $Y^7$ represents a straight chain alkyl group having 4 to 14 carbon atoms)].

Compound A2, as 20-ester derivatives, is disclosed in WO99/33858.

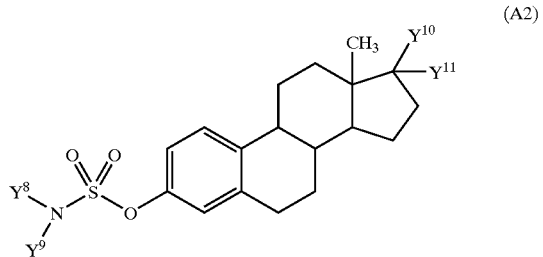

(A2)

{wherein $Y^8$ and $Y^9$ represent a hydrogen atom or a lower alkyl group, or $Y^8$ and $Y^9$ form a nitrogen-containing heterocyclic group together with N adjacent thereto; $Y^{10}$ represents a hydrogen atom, or forms $=CY^{12}Y^{13}$ [wherein $Y^{12}$ and $Y^{13}$ are the same or different and represent a hydrogen atom, a lower alkyl group, $CO_2Y^{14}$ (wherein $Y^{14}$ represents a hydrogen atom, a substituted or unsubstituted lower alkyl group, etc.), etc.] together with $Y^{11}$; and $Y^{11}$ represents a lower alkenyl group, a lower alkanoyl group, etc., or forms $=CY^{12}Y^3$ (wherein $Y^{12}$ and $Y^{13}$ have the same meanings as defined above, respectively) together with $Y^{10}$}.

As antiestrogens, Compound A3 and Compound A4 are disclosed in WO99/33859, however, it has not been known that these compounds will show inhibitory activity against steroid sulfatase.

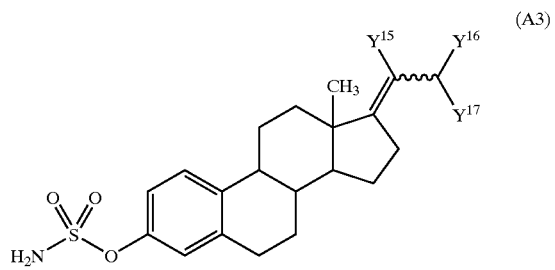

(A3)

{wherein $Y^{15}$ represents a hydrogen atom or an alkyl group; $Y^{16}$ represents a hydrocarbyl group having at least one oxygen atom (—O—), sulfur atom (—S—) or nitrogen atom [—$NY^{18}$— (wherein $Y^{18}$ represents a hydrogen atom or an alkyl group)]; and $Y^{17}$ represents a hydrogen atom, or a hydrocarbyl group having at least one oxygen atom (—O—), sulfur atom (—S—) or nitrogen atom [—$NY^{18}$— (wherein $Y^{18}$ has the same meaning as defined above)]; or $Y^{16}$ and $Y^{17}$ may form a heterocyclic group together with the carbon atom adjacent thereto}.

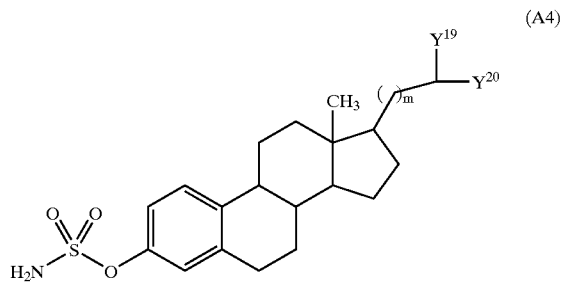

(A4)

{wherein (1) when m indicates an integer of 0 to 6, $Y^{19}$ has the same meaning as defined for $Y^{16}$ above, and $Y^{20}$ represents a hydrogen atom or an alkyl group; and (2) when m is 0, $Y^{19}$ and $Y^{20}$ may form a substituted or unsubstituted, 5-membered or 6-membered ring together with the carbon atom adjacent thereto}.

On the other hand, as reported in WO99/33858, it is considered that compounds having not only inhibitory activity against steroid sulfatase but also an antiestrogenic activity (activity of inhibition of estrogen effect or estrogen biosynthesis) are useful for treating or preventing steroid hormone-dependent diseases, and it is also considered to be useful for treating or preventing such diseases that phenol derivatives (desulfamoylated compounds) produced through hydrolysis of a sulfamate in vivo have an antiestrogenic activity.

DISCLOSURE OF THE INVENTION

One object of the present invention is to provide steroid sulfatase inhibitors comprising, as the active ingredient, an estra-1,3,5(10)-triene derivative or a pharmaceutically acceptable salt thereof. Another object of the present invention is to provide estra-1,3,5(10)-triene derivatives or pharmaceutically acceptable salts thereof that have inhibitory activity against steroid sulfatase and are useful for treating or preventing steroid hormone-dependent diseases.

The invention relates to the following (1) to (28).

(1) Steroid sulfatase inhibitors comprising, as the active ingredient, an estra-1,3,5(10)-triene derivative which is represented by formula (I):

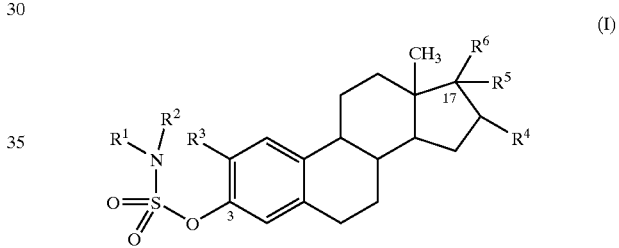

(I)

<wherein $R^1$ and $R^2$ are the same or different and represent a hydrogen atom or a lower alkyl group, or $R^1$ and $R^2$ are combined with N adjacent thereto to form a nitrogen-containing heterocyclic group, or $R^1$ and $R^2$ are combined with N—$SO_2O$—C=C—$R^3$ adjacent thereto to form an oxathiazine dioxide ring or a dihydrooxathiazine dioxide ring;

$R^3$ represents a hydrogen atom, or is combined with $R^1$ and $R^2$ to form an oxathiazine dioxide ring or a dihydrooxathiazine dioxide ring;

$R^4$ represents a hydrogen atom, or is combined with $R^5$ to form a bond;

$R^5$ represents a hydrogen atom, or is combined with $R^4$ to form a bond, or is combined with $R^6$ to form $=CR^7R^8$ <wherein $R^7$ represents a hydrogen atom or a substituted or unsubstituted lower alkyl group; $R^8$ represents $COR^9$ {wherein $R^9$ represents a hydrogen atom, a substituted or unsubstituted lower alkyl group, a substituted or unsubstituted lower cycloalkyl group, a substituted or unsubstituted aryl group, a substituted or unsubstituted heterocyclic group, or $OR^{10}$ (wherein $R^{10}$ represents a substituted or unsubstituted aryl group, or a substituted or unsubstituted heterocyclic group)}, $X^1NR^{11}R^{12}$ <wherein $R^{11}$ and $R^{12}$ are the same or different and represent a hydrogen atom, a substituted or unsubstituted lower alkyl group, a substituted or unsubstituted lower cycloalkyl group, a substituted or unsubstituted aryl group, a substituted or unsubstituted heterocyclic group, OR$^{13}$ (wherein R$^{13}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group), or NR14R$^{15}$ {wherein R$^{14}$ and R$^{15}$ are the same or different and represent a hydrogen atom, a substituted or unsubstituted lower alkyl group, a substituted or unsubstituted lower cycloalkyl group, a substituted or unsubstituted aryl group, a substituted or unsubstituted heterocyclic group, COR$^{16}$ (wherein R$^{16}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group), or SO$_2$R$^{17}$ (wherein R$^{17}$ represents a substituted or unsubstituted lower alkyl group, a substituted or unsubstituted lower cycloalkyl group, a substituted or unsubstituted aryl group, or a substituted or unsubstituted heterocyclic group)}, and X$^1$ represents C=O or C=S>, CSR$^{18}$ (wherein R$^{18}$ represents a substituted or unsubstituted heterocyclic group), a substituted or unsubstituted aryl group, a substituted or unsubstituted heterocyclic group, CR$^{19}$R$^{20}$(OH) (wherein R$^{19}$ and R$^{20}$ are the same or different and represent a hydrogen atom, a substituted or unsubstituted lower alkyl group, a substituted or unsubstituted lower cycloalkyl group, a substituted or unsubstituted aryl group, or a substituted or unsubstituted heterocyclic group), or CHR$^{21}$R$^{22}$ <wherein R$^{21}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group, R$^{22}$ represents a substituted or unsubstituted aryl group, a substituted or unsubstituted heterocyclic group, or NR$^{23}$R$^{24}$ {wherein R$^{23}$ and R$^{24}$ are the same or different and represent a hydrogen atom, a substituted or unsubstituted lower alkyl group, a substituted or unsubstituted lower cycloalkyl group, a substituted or unsubstituted aryl group, a substituted or unsubstituted heterocyclic group, X$^2$R$^{25}$ (wherein R$^{25}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group, and X$^2$ represents C=O or C=S), CO$_2$R$^{26}$ (wherein R$^{26}$ represents a substituted or unsubstituted lower alkyl group, a substituted or unsubstituted lower cycloalkyl group, a substituted or unsubstituted aryl group, or a substituted or unsubstituted heterocyclic group), X$^3$NR$^{27}$R$^2$ (wherein R$^{27}$ and R$^{28}$ are the same or different and represent a hydrogen atom, a substituted or unsubstituted lower alkyl group, a substituted or unsubstituted lower cycloalkyl group, a substituted or unsubstituted aryl group, or a substituted or unsubstituted heterocyclic group, and X$^3$ represents C=O or C=S), or SO$_2$R$^{29}$ (wherein R$^{29}$ represents an amino group, a mono or di(lower alkyl)amino group, a substituted or unsubstituted lower alkyl group, a substituted or unsubstituted lower cycloalkyl group, a substituted or unsubstituted aryl group, or a substituted or unsubstituted heterocyclic group)}>>;

R$^6$ represents
1) a cyano group,
2) an amino group,
3) CHR$^{30}$R$^{31}$ <wherein R$^{30}$ represents a hydrogen atom, or a substituted or unsubstituted lower alkyl group, R$^{31}$ represents COR$^{32}$ {wherein R$^{32}$ represents a hydrogen atom, a substituted or unsubstituted lower alkyl group, a substituted or unsubstituted lower cycloalkyl group, a substituted or unsubstituted aryl group, a substituted or unsubstituted heterocyclic group, or OR$^{33}$ (wherein R$^{33}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group)}, X$^4$NR$^{34}$R$^{35}$ <wherein R$^{34}$ and R$^{35}$ are the same or different and represent a hydrogen atom, a substituted or unsubstituted lower alkyl group, a substituted or unsubstituted lower cycloalkyl group, a substituted or unsubstituted aryl group, a substituted or unsubstituted heterocyclic group, OR$^{36}$ (wherein R$^{36}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group), or NR$^{37}$R$^{38}$ {wherein R$^{37}$ and R$^{38}$ are the same or different and represent a hydrogen atom, a substituted or unsubstituted lower alkyl group, a substituted or unsubstituted lower cycloalkyl group, a substituted or unsubstituted aryl group, a substituted or unsubstituted heterocyclic group, COR$^{39}$ (wherein R$^{39}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group), or SO$_2$R$^{40}$ (wherein R$^{40}$ represents a substituted or unsubstituted lower alkyl group, a substituted or unsubstituted lower cycloalkyl group, a substituted or unsubstituted aryl group, or a substituted or unsubstituted heterocyclic group)}, and X$^4$ represents C=O or C=S>, CSR$^{41}$ (wherein R$^{41}$ represents a substituted or unsubstituted heterocyclic group), CR$^{42}$R$^{43}$ (OH) (wherein R$^{42}$ and R$^{43}$ have the same meanings as defined for R$^{19}$ and R$^{20}$ above, respectively), or CHR$^{44}$R$^{45}$ (wherein R$^{44}$ and R$^{45}$ have the same meanings as defined for R$^{21}$ and R$^{22}$ above, respectively)>, 4) COR$^{53}$ <wherein R$^{53}$ represents a substituted lower alkyl group, a substituted lower cycloalkyl group, a substituted or unsubstituted aryl group, a substituted or unsubstituted heterocyclic group, OR$^{54}$ (wherein R$^{54}$ represents a substituted lower alkyl group, a substituted or unsubstituted lower cycloalkyl group, a substituted or unsubstituted aryl group, or a substituted or unsubstituted heterocyclic group), or NR$^{55}$R$^{56}$ <wherein R$^{55}$ represents a hydrogen atom, a substituted or unsubstituted lower alkyl group, a substituted or unsubstituted lower cycloalkyl group, a substituted or unsubstituted aryl group, a substituted or unsubstituted heterocyclic group, or OR$^{57}$ (wherein R$^{57}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group), and R$^{56}$ represents a substituted lower alkyl group, a substituted or unsubstituted lower cycloalkyl group, a substituted or unsubstituted aryl group, a substituted or unsubstituted heterocyclic group, OR$^{58}$ (wherein R$^{58}$ represents a substituted lower alkyl group, a substituted or unsubstituted lower cycloalkyl group, a substituted or unsubstituted aryl group, or a substituted or unsubstituted heterocyclic group), or NR$^{59}$R$^{60}$ {wherein R$^{59}$ and R$^{60}$ are the same or different and represent a hydrogen atom, a substituted or unsubstituted lower alkyl group, a substituted or unsubstituted lower cycloalkyl group, a substituted or unsubstituted aryl group, a substituted or unsubstituted heterocyclic group, COR$^{61}$ (wherein $R^{61}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group), or $SO_2R^{62}$ (wherein $R^{62}$ represents a substituted or unsubstituted lower alkyl group, a substituted or unsubstituted lower cycloalkyl group, a substituted or unsubstituted aryl group, or a substituted or unsubstituted heterocyclic group)}>>, 5) $CSR^{63}$ {wherein $R^{63}$ represents a substituted or unsubstituted heterocyclic group, or $NR^{64}R^{65}$ (wherein $R^{64}$ and $R^{65}$ have the same meanings as defined for $R^{34}$ and $R^{35}$ above, respectively)},
6) a substituted or unsubstituted aryl group,
7) a substituted or unsubstituted heterocyclic group,
8) $CR^{71}R^{72}(OH)$ (wherein $R^{71}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group, and $R^{72}$ represents a substituted or unsubstituted lower alkyl group, a substituted or unsubstituted lower cycloalkyl group, a substituted or unsubstituted aryl group, or a substituted or unsubstituted heterocyclic group),
9) $CHR^{73}R^{74}$ (wherein $R^{73}$ and $R^{74}$ have the same meanings as defined for $R^{21}$ and $R^{22}$ above, respectively),
10) $NR^{82}R^{83}$ {wherein $R^{82}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group, and $R^{83}$ represents a substituted or unsubstituted lower alkyl group, a substituted or unsubstituted lower cycloalkyl group, a substituted or unsubstituted aryl group, a substituted or unsubstituted heterocyclic group, $COR^{84}$ (wherein $R^{84}$ represents a substituted lower alkyl group, a substituted or unsubstituted lower cycloalkyl group, a substituted or unsubstituted aryl group, or a substituted or unsubstituted heterocyclic group), $CSR^{85}$ (wherein $R^{85}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group), $CO_2R^{86}$ (wherein $R^{86}$ represents a substituted or unsubstituted lower alkyl group, a substituted or unsubstituted lower cycloalkyl group, a substituted or unsubstituted aryl group, or a substituted or unsubstituted heterocyclic group), $X^9NR^{87}R^{88}$ (wherein $R^{87}$ and $R^{88}$ are the same or different and represent a hydrogen atom, a substituted or unsubstituted lower alkyl group, a substituted or unsubstituted lower cycloalkyl group, a substituted or unsubstituted aryl group, or a substituted or unsubstituted heterocyclic group, and $X^9$ represents C=O or C=S), or $SO_2R^{89}$ (wherein $R^{89}$ represents an amino group, a mono or di(lower alkyl)amino group, a substituted or unsubstituted lower alkyl group, a substituted or unsubstituted lower cycloalkyl group, a substituted or unsubstituted aryl group, or a substituted or unsubstituted heterocyclic group)}, or
11) $NR^{90}COR^{91}$ (wherein $R^{90}$ represents a substituted lower alkyl group, a substituted or unsubstituted lower cycloalkyl group, a substituted or unsubstituted aryl group, or a substituted or unsubstituted heterocyclic group, and $R^{91}$ represents a hydrogen atom or a lower alkyl group), or
12) $R^6$ is combined with $R^5$ to form $=CR^7R^8$ (wherein $R^7$ and $R^8$ have the same meanings as defined above, respectively)>, or a pharmaceutically acceptable salt thereof.

(2) Estra-1,3,5(10)-triene derivatives which are represented by formula (IA):

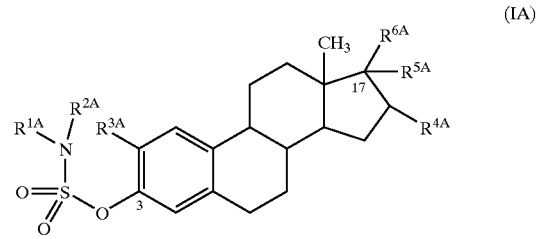

(IA)

<wherein $R^{1A}$, $R^{2A}$ and $R^{3A}$ have the same meanings as defined for $R^1$, $R^2$ and $R^3$ above, respectively;

(1) when $R^{4A}$ is a hydrogen atom, $R^{5A}$ is a hydrogen atom, or is combined with $R^{6A}$ to form $=CR^{7A1}R^{8A1}$ {wherein $R^{7A1}$ has the same meaning as defined for $R^7$ above, $R^{8A1}$ represents $COR^{9A1}$ (wherein $R^{9A1}$ has the same meaning as defined for $R^9$ above), $X^{1A1}NR^{11A1}R^{12A1}$ (wherein $R^{11A1}$, $R^{12A1}$ and $X^{1A1}$ have the same meanings as defined for $R^{11}$, $R^{12}$ and $X^1$ above, respectively), $CSR^{18A1}$ (wherein $R^{18A1}$ has the same meaning as defined for $R^{18}$ above), $CR^{19A1}R^{20A1}(OH)$ (wherein $R^{19A1}$ and $R^{20A1}$ have the same meanings as defined for $R^{19}$ and $R^{20}$ above, respectively), or $CHR^{21A1}R^{22A1}$ (wherein $R^{21A1}$ and $R^{22A1}$ have the same meanings as defined for $R^{21}$ and $R^{22}$ above, respectively)};
$R^{6A}$ represents a cyano group, an amino group, $CHR^{30A1}R^{31A1}$ <wherein $R^{30A1}$ has the same meaning as defined for $R^{30}$ above, $R^{31A1}$ represents $COR^{32A1}$ (wherein $R^{32A1}$ has the same meaning as defined for $R^{32}$ above), $X^{4A1}NR^{34A1}R^{35A1}$ (wherein $R^{34A1}$, $R^{35A1}$ and $X^{4A1}$ have the same meanings as defined for $R^{11}$, $R^{12}$ and $X^4$ above, respectively), $CSR^{41A1}$ (wherein $R^{41A1}$ has the same meaning as defined for $R^{41}$ above), or $CHR^{44A1}R^{45A1}$ <wherein $R^{44A1}$ has the same meaning as defined for $R^{44}$ above, $R^{45A1}$ represents $NR^{46A1}R^{47A1}$ {wherein $R^{46A1}$ has the same meaning as defined for $R^{23}$ above, $R^{47A1}$ represents $CSR^{48A1}$ (wherein $R^{48A1}$ has the same meaning as defined for $R^{25}$ above), $CO_2R^{49A1}$ (wherein $R^{49A1}$ has the same meaning as defined for $R^{26}$ above), $X^{6A1}NR^{50A1}R^{51A1}$ (wherein $R^{50A1}$, $R^{51A1}$ and $X^{6A1}$ have the same meanings as defined for $R^{27}$, $R^{28}$ and $X^3$ above, respectively), or $SO_2R^{52A1}$ (wherein $R^{52A1}$ has the same meaning as defined for $R^{29}$ above)}>>, $COR^{53A1}$ (wherein $R^{53A1}$ has the same meaning as defined for $R^{53}$ above), $CSR^{63A1}$ (wherein $R^{63A1}$ has the same meaning as defined for $R^{63}$ above), $CR^{71A1}R^{72A1}(OH)$ (wherein $R^{71A1}$ and $R^{72A1}$ have the same meanings as defined for $R^{71}$ and $R^{72}$ above, respectively), $CHR^{73A1}NR^{75A1}R^{76A1}$ (wherein $R^{73A1}$, $R^{75A1}$ and $R^{76A1}$ have the same meanings as defined for $R^{21}$, $R^{23}$ and $R^{24}$ above, respectively), $NR^{82A1}R^{83A1}$ (wherein $R^{82A1}$ and $R^{83A1}$ have the same meanings as defined for $R^{82}$ and $R^{83}$ above, respectively), or $NR^{90A1}COR^{91A1}$ (wherein $R^{90A1}$ and $R^{91A1}$ have the same meanings as defined for $R^{90}$ and $R^{91}$ above, respectively), or $R^{6A}$ is combined with $R^{5A}$ to form $=CR^{7A1}R^{8A1}$ (wherein $R^{7A1}$ and $R^{8A1}$ have the same meanings as defined above, respectively), or a pharmaceutically acceptable salt thereof;

(2) when $R^{4A}$ and $R^{5A}$ are combined to form a bond, $R^{6A}$ represents a cyano group, $CHR^{30A2}R^{31A2}$ (wherein $R^{30A2}$ and $R^{31A2}$ have the same meanings as defined for $R^{30}$ and $R^{31}$ above, respectively), $COR^{53A2}$ (wherein $R^{53A2}$ has the same meaning as defined for $R^{53}$ above), $CSR^{63A2}$ (wherein $R^{63A2}$ has the same meaning as defined for $R^{63}$ above), a substituted or unsubstituted aryl group, a substituted or unsubstituted heterocyclic group, $CR^{71A2}R^{72A2}(OH)$ (wherein $R^{71A2}$ and $R^{72A2}$ have the same meanings as defined for $R^{71}$ and $R^{72}$ above, respectively), $CHR^{73A2}R^{74A2}$ (wherein $R^{73A2}$ and $R^{74A2}$ have the same meanings as defined for $R^{73}$ and $R^{74}$ above, respectively), $NR^{82A2}R^{83A2}$ (wherein $R^{82A2}$ and $R^{83A2}$ have the same meanings as defined for $R^{82}$ and $R^{83}$ above, respectively), or $NR^{90A2}COR^{91A2}$ (wherein $R^{90A2}$ and $R^{91A2}$ have the same meanings as defined for $R^{90}$ and $R^{91}$ above, respectively)>, or pharmaceutically acceptable salts thereof.

(3) The estra-1,3,5(10)-triene derivatives or the pharmaceutically acceptable salts thereof according to above (2), wherein $R^{4A}$ is a hydrogen atom, and $R^{5A}$ and $R^{6A}$ are combined to form $=CR^{7A1}R^{8A1}$ (wherein $R^{7A1}$ and $R^{8A1}$ have the same meanings as defined above, respectively).

(4) The estra-1,3,5(10)-triene derivatives or the pharmaceutically acceptable salts thereof according to above (3), wherein $R^{8A1}$ is $COR^{9A3}$ (wherein $R^{9A3}$ is a substituted or unsubstituted heterocyclic group), $X^{1A1}NR^{11A1}R^{12A1}$ (wherein $R^{11A1}$, $R^{12A1}$ and $X^{1A1}$ have the same meanings as defined above, respectively), or $CSR^{18A1}$ (wherein $R^{18A1}$ has the same meaning as defined above).

(5) The estra-1,3,5(10)-triene derivatives or the pharmaceutically acceptable salts thereof according to above (2), wherein $R^{4A}$ and $R^{5A}$ are hydrogen atoms.

(6) The estra-1,3,5(10)-triene derivatives or the pharmaceutically acceptable salts thereof according to above (5), wherein $R^{6A}$ is $CHR^{30A1}R^{31A3}$ {wherein $R^{30A1}$ has the same meaning as defined above, $R^{31A3}$ represents $X^{4A1}NR^{34A1}R^{35A1}$ (wherein $R^{34A1}$, $R^{35A1}$ and $X^{4A1}$ have the same meanings as defined above, respectively) or $CSR^{41A1}$ (wherein $R^{41A1}$ has the same meaning as defined above)}, $COR^{53A1}$ (wherein $R^{53A1}$ has the same meaning as defined above), $CSR^{63A1}$ (wherein $R^{63A1}$ has the same meaning as defined above), $NR^{82A1}R^{83A1}$ (wherein $R^{82A1}$ and $R^{83A1}$ have the same meanings as defined above, respectively) or $NR^{90A1}COR^{91A1}$ (wherein $R^{90A1}$ and $R^{91A1}$ have the same meanings as defined above, respectively).

(7) The estra-1,3,5(10)-triene derivatives or the pharmaceutically acceptable salts thereof according to above (2), wherein $R^{4A}$ and $R^{5A}$ are combined to form a bond, and $R^{6A}$ is a cyano group, $CHR^{30A2}R^{31A2}$ (wherein $R^{30A2}$ and $R^{31A2}$ have the same meanings as defined above), $COR^{53A2}$ (wherein $R^{53A2}$ has the same meaning as defined above), $CSR^{63A2}$ (wherein $R^{63A2}$ has the same meaning as defined above), a substituted or unsubstituted aryl group, a substituted or unsubstituted heterocyclic group, $CR^{71A2}R^{72A2}(OH)$ (wherein $R^{71A2}$ and $R^{72A2}$ have the same meanings as defined above), $CHR^{73A2}R^{74A2}$ (wherein $R^{73A2}$ and $R^{74A2}$ have the same meanings as above), $NR^{82A2}R^{83A2}$ (wherein $R^{82A2}$ and $R^{83A2}$ have the same meanings as defined above), or $NR^{90A2}COR^{91A2}$ (wherein $R^{90A2}$ and $R^{91A2}$ have the same meanings as defined above).

(8) The estra-1,3,5(10)-triene derivatives or the pharmaceutically acceptable salts thereof according to above (7), wherein $R^{6A}$ is $COR^{53A3}$ {wherein $R^{53A3}$ is a substituted or unsubstituted aryl group, a substituted or unsubstituted heterocyclic group, $OR^{54A1}$ (wherein $R^{54A1}$ has the same meaning as defined for $R^{54}$ above) or $NR^{55A1}R^{56A1}$ (wherein $R^{55A1}$ and $R^{56A1}$ have the same meanings as defined for $R^{55}$ and $R^{56}$ above, respectively)}, $CSR^{63A2}$ (wherein $R^{63A2}$ has the same meaning as defined above), a substituted or unsubstituted aryl group, a substituted or unsubstituted heterocyclic group, or $CR^{71A2}R^{72A2}(OH)$ (wherein $R^{71A2}$ and $R^{72A2}$ have the same meanings as defined above, respectively).

(9) The estra-1,3,5(10)-triene derivatives which are represented by formula (IB):

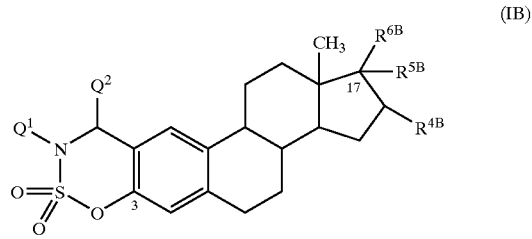

(IB)

(wherein $Q^1$ and $Q^2$ are hydrogen atoms, or $Q^1$ and $Q^2$ are combined to form a bond; and $R^{4B}$, $R^{5B}$ and $R^{6B}$ have the same meanings as defined for $R^{4A}$ $R^{5A}$ and $R^{6A}$ above, respectively) according to above (2), or pharmaceutically acceptable salts thereof.

(10) The estra-1,3,5(10)-triene derivatives or the pharmaceutically acceptable salts thereof according to any one of above (2) to (8), wherein $R^{3A}$ is a hydrogen atom.

(11) The estra-1,3,5(10)-triene derivatives or the pharmaceutically acceptable salts thereof according to any one of above (2) to (8), wherein $R^{1A}$, $R^{2A}$ and $R^{3A}$ are hydrogen atoms.

(12) Agents for treating or preventing steroid sulfatase-related diseases, comprising at least one of the estra-1,3,5 (10)-triene derivatives or the pharmaceutically acceptable salts thereof according to above (1).

(13) Steroid sulfatase inhibitors comprising at least one of the estra-1,3,5(10)-triene derivatives or the pharmaceutically acceptable salts thereof according to any one of above (2) to (11).

(14) Agents for treating or preventing breast cancer, endometrial cancer, ovarian cancer or prostate cancer, comprising at least one of the estra-1,3,5(10)-triene derivatives or the pharmaceutically acceptable salts thereof according to any one of above (2) to (11).

(15) Antitumor agents comprising at least one of the estra-1,3,5(10)-triene derivatives or the pharmaceutically acceptable salts thereof according to any one of above (2) to (11).

(16) Agents for treating or preventing steroid sulfatase-related diseases, comprising at least one of the estra-1,3,5 (10)-triene derivatives or the pharmaceutically acceptable salts thereof according to any one of above (2) to (11).

(17) Agents for treating or preventing steroid hormone-dependent diseases, comprising at least one of the estra-1, 3,5(10)-triene derivatives or the pharmaceutically acceptable salts thereof according to any one of above (2) to (11).

(18) Agents for treating or preventing steroid hormone-dependent diseases, comprising at least one of the estra-1, 3,5(10)-triene derivatives or the pharmaceutically acceptable salts thereof according to any one of above (2) to (11) which further have an antiestrogen activity.

(19) Agents for treating or preventing steroid hormone-dependent diseases, comprising at least one of the estra-1, 3,5(10)-triene derivatives or the pharmaceutically acceptable salts thereof according to any one of above (2) to (11) which produce a phenol derivative having an antiestrogen activity through hydrolysis of a sulfamate in vivo.

(20) Pharmaceutical compositions comprising at least one of the estra-1,3,5(10)-triene derivatives or the pharmaceutically acceptable salts thereof according to any one of above (2) to (11).

(21) A method for treating malignant tumors, comprising the step of administering a therapeutically effective-amount of at least one of the estra-1,3,5(10)-triene derivatives or the pharmaceutically acceptable salts thereof according to any one of above (2) to (11).

(22) A method for treating breast cancer, endometrial cancer, ovarian cancer or prostate cancer, comprising the step of administering a therapeutically effective amount of at least one of the estra-1,3,5(10)-triene derivatives or the pharmaceutically acceptable salts thereof according to any one of above (2) to (11).

(23) A method for treating androgen-dependent diseases, comprising the step of administering a therapeutically effective amount of at least one of the estra-1,3,5(10)-triene derivatives or the pharmaceutically acceptable salts thereof according to above (1).

(24) A method for treating steroid hormone-dependent diseases, comprising the step of administering a therapeutically effective amount of at least one of the estra-1,3,5 (10)-triene derivatives or the pharmaceutically acceptable salts thereof according to any one of above (2) to (11).

(25) Use of the estra-1,3,5(10)-triene derivative or the pharmaceutically acceptable salt thereof according to any one of above (2) to (11) for the manufacture of an antitumor composition.

(26) Use of the estra-1,3,5(10)-triene derivative or the pharmaceutically acceptable salt thereof according to any one of above (2) to (11) for the manufacture of an agent for treating breast cancer, endometrial cancer, ovarian cancer or prostate cancer.

(27) Use of the estra-1,3,5(10)-triene derivative or the pharmaceutically acceptable salt thereof according to above (1) for the manufacture of an agent for treating androgen-dependent diseases.

(28) Use of the estra-1,3,5(10)-triene derivative or the pharmaceutically acceptable salt thereof according to any one of above (2) to (11) for the manufacture of an agent for treating steroid hormone-dependent diseases.

Hereinafter, the compound represented by formula (I) is also referred to as Compound (I). The compounds of other formula numbers are also referred to in the same manner.

The lower alkyl group includes straight chain or branched alkyl groups having 1 to 8 carbon atoms, such as methyl, ethyl, propyl, isopropyl, butyl, isobutyl, sec-butyl, tert-butyl, pentyl, isopentyl, neopentyl, hexyl, heptyl, octyl and isooctyl.

The lower cycloalkyl group includes cycloalkyl groups having 3 to 8 carbon atoms, such as cyclopropyl, cyclobutyl, cyclopentyl, cyclohexyl and cyclooctyl.

The aryl group includes aryl groups having 6 to 14 carbon atoms, such as phenyl, naphthyl and anthranyl.

The heterocyclic group includes an alicyclic heterocyclic group and an aromatic heterocyclic group.

The alicyclic heterocyclic group includes, for example, tetrahydropyranyl, tetrahydrofuranyl, pyrrolidinyl, piperidino, piperidinyl, perhydroazepinyl, perhydroazocinyl, morpholino, morpholinyl, thiomorpholino, thiomorpholinyl, piperazinyl, homopiperazinyl, dioxolanyl, imidazolidinyl, imidazolinyl, pyrazolidinyl, indolinyl, isoindolinyl, 2-pyrrolinyl, 2-pyrrolidonyl, 3-pyrrolidonyl, 2-piperidonyl, 3-piperidonyl, 4-piperidonyl, perhydro-2-azepinonyl, perhydro-3-azepinonyl, perhydro-4-azepinonyl, 2-thiazolidonyl, 4-thiazolidonyl, 2-oxazolidonyl, 4-oxazolidonyl, succinimido, phthalimido, glutarimido, maleimido, hydantoinyl, thiazolidinedionyl, oxazolidinedionyl, etc.

The aromatic heterocyclic group includes, for example, furyl, thienyl, pyrrolyl, imidazolyl, pyrazolyl, triazolyl, tetrazolyl, oxazolyl, isoxazolyl, thiazolyl, isothiazolyl, 1,2,3-oxadiazolyl, 1,2,4-oxadiazolyl, 1,3,4-oxadiazolyl, 1,2,3-thiadiazolyl, 1,2,4-thiadiazolyl, 1,3,4-thiadiazolyl, furazanyl, pyridyl, pyrimidinyl, pyrazinyl, pyridazinyl, quinolyl, isoquinolyl, quinazolinyl, phthalazinyl, purinyl, indolyl, isoindolyl, 2-pyridonyl, 4-pyridonyl, uracilyl, etc.

The nitrogen-containing heterocyclic group that is formed together with the adjacent N (this may further contain O, S or any other N) includes, for example, pyrrolidinyl, piperidino, perhydroazepinyl, perhydroazocinyl, morpholino, thiomorpholino, piperazinyl, homopiperazinyl, 2-pyrrolinyl, imidazolidinyl, imidazolinyl, pyrazolidinyl, indolinyl, isoindolinyl, indolyl, isoindolyl, etc.

The lower alkyl moiety in the mono(lower alkyl)amino and di(lower alkyl)amino groups has the same meaning as that of the lower alkyl group defined above.

The substituents in the substituted lower alkyl group include 1 to 3 substituents which are the same or different, for example, a hydroxyl group, a lower cycloalkyl group, a lower alkenyl group, a lower alkadienyl group, a lower alkatrienyl group, a lower alkynyl group, a lower alkoxy group, a tri(lower alkyl)silyloxy group, a lower alkoxy-lower alkoxy group, a lower alkanoyloxy group, an azido group, a cyano group, a halogen atom, a lower alkanoyl group, a substituted or unsubstituted aryl group, a substituted or unsubstituted heterocyclic group, $CONR^{1C}R^{2C}$ {wherein $R^{1C}$ and $R^{2C}$ are the same or different and represent a hydrogen atom, a lower alkyl group, a lower cycloalkyl group, a substituted or unsubstituted aryl group, a substituted or unsubstituted heterocyclic group, $OR^{3C}$ (wherein $R^{3C}$ represents a hydrogen atom, a lower alkyl group, a lower cycloalkyl group, a substituted or unsubstituted aryl group, or a substituted or unsubstituted heterocyclic group), or $NR^{4C}R^{5C}$ [wherein $R^{4C}$ and $R^{5C}$ are the same or different and represent a hydrogen atom, a lower alkyl group, a lower cycloalkyl group, a substituted or unsubstituted aryl group, a substituted or unsubstituted heterocyclic group, $COR^{6C}$ (wherein $R^{6C}$ represents a hydrogen atom, a lower alkyl group, a lower cycloalkyl group, a substituted or unsubstituted aryl group, or a substituted or unsubstituted heterocyclic group), or $SO_2R^{7C}$ (wherein $R^{7C}$ represents a lower alkyl group, a lower cycloalkyl group, a substituted or unsubstituted aryl group, or a substituted or unsubstituted heterocyclic group)]}, $CO_2R^{8C}$ (wherein $R^{8C}$ represents a hydrogen atom, a lower alkyl group, a lower cycloalkyl group, a substituted or unsubstituted aryl group, or a substituted or unsubstituted heterocyclic group), $(OCH_2CH_2)_n$ $OCH_3$ (wherein n indicates an integer of from 1 to 10), $NR^{9C}R^{10C}$ {wherein $R^{9C}$ and $R^{10C}$ are the same or different and represent a hydrogen atom, a lower alkyl group, a lower cycloalkyl group, a substituted or unsubstituted aryl group, a substituted or unsubstituted heterocyclic group, $X^{1C}R^{11C}$ [wherein $R^{11C}$ represents a hydrogen atom, a lower alkyl group, a lower cycloalkyl group, a substituted or unsubstituted aryl group, a substituted or unsubstituted heterocyclic group, or $NR^{12C}R^{13C}$ (wherein $R^{12C}$ and $R^{13C}$ are the same or different and represent a hydrogen atom, a lower alkyl group, a lower cycloalkyl group, a substituted or unsubstituted aryl group, or a substituted or unsubstituted heterocyclic group), $X^{1C}$ represents C=O or C=S], or $SO_2R^{14C}$ (wherein $R^{14C}$ represents a lower alkyl group, a lower cycloalkyl group, a substituted or unsubstituted aryl group, or a substituted or unsubstituted heterocyclic group)}, $SO_2R^{15C}$ [wherein $R^{15C}$ represents a lower alkyl group or $NR^{16C}R^{17C}$ (wherein $R^{16C}$ and $R^{17C}$ are the same or different and represent a hydrogen atom or a lower alkyl group)], etc.

The substituents in the substituted lower cycloalkyl group, the substituted aryl group and the substituted heterocyclic group include 1 to 3 substituents which are the same or different, for example, a hydroxyl group, a lower alkyl group, a lower alkenyl group, a lower alkadienyl group, a lower alkatrienyl group, a lower alkynyl group, a lower cycloalkyl group, a lower alkoxy group, a tri(lower alkyl) silyloxy group, a lower alkoxy-lower alkoxy group, a lower alkanoyloxy group, an azido group, a nitro group, a cyano group, a halogen atom, a lower alkanoyl group, an aryl group, a heterocyclic group, $CONR^{18C}R^{19C}$ {wherein $R^{18C}$ and $R^{19C}$ are the same or different and represent a hydrogen atom, a lower alkyl group, a lower cycloalkyl group, an aryl group, a heterocyclic group, $OR^{20C}$ (wherein $R^{20C}$ represents a hydrogen atom, a lower alkyl group, a lower cycloalkyl group, an aryl group, or a heterocyclic group), or $NR^{21C}R^{22C}$ [wherein $R^{21C}$ and $R^{22C}$ are the same or different and represent a hydrogen atom, a lower alkyl group, a lower cycloalkyl group, an aryl group, a heterocyclic group, $COR^{23C}$ (wherein $R^{23C}$ represents a hydrogen atom, a lower alkyl group, a lower cycloalkyl group, an aryl group, or a heterocyclic group), or $SO_2R^{24C}$ (wherein $R^{24C}$ represents a lower alkyl group, a lower cycloalkyl group, an aryl group, or a heterocyclic group)]}, $CO_2R^{25C}$ (wherein $R^{25C}$ represents a hydrogen atom, a lower alkyl group, a lower cycloalkyl group, an aryl group, or a heterocyclic group), $(OCH_2CH_2)_{na}OCH_3$ (wherein na indicates an integer of from 1 to 10), $NR^{26C}R^{27C}$ {wherein $R^{26C}$ and $R^{27C}$ are the same or different and represent a hydrogen atom, a lower alkyl group, a lower cycloalkyl group, an aryl group, a heterocyclic group, $X^{2C}R^{28C}$ [wherein $R^{28C}$ represents a hydrogen atom, a lower alkyl group, a lower cycloalkyl group, an aryl group, a heterocyclic group, or $NR^{29C}R^{30C}$ (wherein $R^{29C}$ and $R^{30C}$ are the same or different and represent a hydrogen atom, a lower alkyl group, a lower cycloalkyl group, an aryl group, or a heterocyclic group), and $X^{2C}$ has the same meaning as defined for $X^{1C}$ above], or $SO_2R^{31C}$ (wherein $R^{31C}$ represents a lower alkyl group, a lower cycloalkyl group, an aryl group, or a heterocyclic group)}, $SO_2R^{32C}$ (wherein $R^{32C}$ has the same meaning as defined for $R^{15C}$ above), etc.

In the definitions of the substituents in the substituted lower alkyl group, the substituted lower cycloalkyl group, the substituted aryl group and the substituted heterocyclic group, the lower alkyl group, the lower cycloalkyl group, the aryl group and the heterocyclic group have the same meanings as defined above, respectively. The lower alkyl moiety in the lower alkoxy group, the lower alkoxy-lower alkoxy group and the tri(lower alkyl)silyloxy group has the same meaning as defined for the lower alkyl group above.

The lower alkanoyl group and the lower alkanoyl moiety in the lower alkanoyloxy group include straight chain or branched alkanoyl groups having 1 to 8 carbon atoms, such as formyl, acetyl, propanoyl, isopropanoyl, butanoyl and caproyl.

The lower alkenyl group includes alkenyl groups having 2 to 8 carbon atoms, such as vinyl, allyl, 1-propenyl, 2-butenyl, 1-pentenyl and 2-hexenyl. The lower alkadienyl group includes alkadienyl groups having 4 to 8 carbon atoms, such as 1,3-pentadienyl, 1,3-hexadienyl and 2,4-hexadienyl. The lower alkatrienyl group includes alkatrienyl groups having 6 to 8 carbon atoms, such as 1,3,5-hexatrienyl. The lower alkynyl group includes having alkynyl groups having 2 to 8 carbon atoms, such as ethynyl, 1-propynyl, 1-hexynyl and 1-octynyl.

The halogen atom includes fluorine, chlorine, bromine and iodine atoms.

The pharmaceutically acceptable salts of Compound (I), Compound (IA) and Compound (IB) include salts such as acid addition salts, metal salts, ammonium salts, organic amine addition salts and amino acid addition salts thereof. The acid addition salts include, for example, inorganic acid salts such as hydrochlorides, hydrobromides, sulfates and phosphates; and organic acid salts such as formates, acetates, oxalates, benzoates, methanesulfonates, p-toluenesulfonates, maleates, fumarates, tartrates, citrates, succinates and lactates. The metal salts include, for example, alkali metal salts such as lithium salts, sodium salts and potassium salts; alkaline earth metal salts such as magnesium salts and calcium salts; aluminium salts; zinc salts, etc. The ammonium salts include, for example, ammonium, tetramethylammonium, etc. The organic amine addition salts include, for example, addition salts of morpholine, piperidine, etc.; and amino acid addition salts include, for example, addition salts of glycine, phenylalanine, aspartic acid, glutamic acid, lysine, etc.

In the steroid sulfatase inhibitors of the present invention, the estra-1,3,5(10)-triene derivatives or the pharmaceutically acceptable salts thereof as the active ingredient can be generally produced from estrone or various estra-1,3,5(10)-triene derivatives as the starting compound. The estra-1,3,5(10)-triene derivatives or the pharmaceutically acceptable salts thereof as the active ingredient may exist in the form of various stereoisomers, geometrical isomers, regioisomers, tautomers, etc. The estra-1,3,5(10)-triene derivatives or the pharmaceutically acceptable salts thereof used in the present invention include all such possible isomers and the mixtures thereof, and the mixture thereof in any ratio can be used.

Methods for production of Compound (I) are described below.

The process for production of Compound (I) essentially comprises each step described below, and any of these steps may be suitably combined to give the intended products. In Production Methods described below, if the defined groups vary under the process condition or are unsuitable to the process condition, they may be optionally protected and deprotected in any method generally employed in the art of synthetic organic chemistry, to give the intended compounds (for example, refer to *Protective Groups in Organic Synthesis* written by T. W. Greene and published by John Wiley & Sons Inc. in 1981). Also if desired, the order of the reaction steps may be changed. Protective groups of the phenolic hydroxyl group at 3-position in the steroids to be used in the process for obtaining the intended compounds are not limited only to those described in the production methods described below, and any protective group generally used in synthetic organic chemistry (for example, the protective group usable herein includes methoxymethyl, methoxyethoxymethyl, allyl, tetrahydropyranyl, phenacyl, p-methoxybenzyl, tert-butyldimethylsilyl, pivaloyl, methoxycarbonyl, vinyloxycarbonyl, benzyl, benzoyl, p-toluenesulfonyl, trifluoromethanesulfonyl, etc.) can be used. For deprotection of the protective groups, employable is any method generally employed in the art of synthetic organic chemistry (for example, refer to *Protective Groups in Organic Synthesis* written by T. W. Greene and published by John Wiley & Sons Inc. in 1981).

Production Method 1

Compound (Ia) can be obtained from Compound (C), which is obtained from estrone in a method similar to a known method [e.g., *Tetrahedron Letters*, Vol. 26, p. 1109 (1985); *Tetrahedron Letters*, Vol. 33, p. 3939 (1992); *The Journal of Organic Chemistry*, Vol. 59, p. 6683 (1994);

*Helvetica Chimica Acta*, Vol. 81, p. 2264 (1998)], according to the reaction process described below.

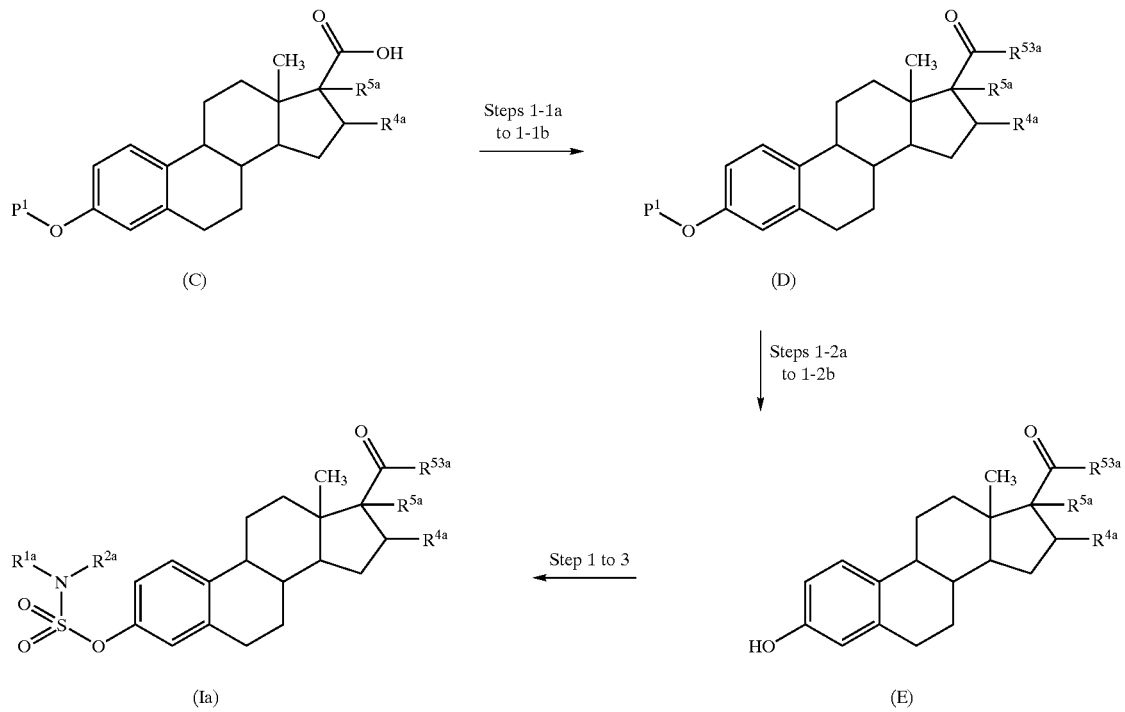

[wherein $R^{1a}$ and $R^{2a}$ are the same or different and represent a hydrogen atom or a lower alkyl group, or $R^{1a}$ and $R^{2a}$ are combined with N adjacent thereto to form a nitrogen-containing heterocyclic group; $R^{4a}$ represents a hydrogen atom, or is combined with $R^{5a}$ to form a bond; $R^{5a}$ represents a hydrogen atom, or is combined with $R^{4a}$ to form a bond; $R^{53a}$ represents $OR^{54}$ (wherein $R^{54}$ has the same meaning as defined above), a substituted or unsubstituted heterocyclic group bonding to the adjacent carbonyl group via its N, or $NR^{55}R^{56}$ (wherein $R^{55}$ and $R^{56}$ have the same meanings as defined above, respectively); and $P^1$ represents a methyl or acetyl group].

Step 1-1a:

Compound (D) can be obtained by reacting Compound (C) with Compound (II) represented by $HOR^{54}$ (wherein $R^{54}$ has the same meaning as defined above), a corresponding substituted or unsubstituted heterocyclic compound, or Compound (III) represented by $HNR^{55}R^{56}$ (wherein $R^{55}$ and $R^{56}$ have the same meanings as defined above, respectively) or an acid addition salt of Compound (III) in the presence of a condensing agent.

Examples of the solvent include tetrahydrofuran (THF), toluene, dichloromethane, dimethylformamide (DMF), etc., which may be used alone or as a mixture thereof.

Examples of the condensing agent include 1-(3-dimethylaminopropyl)-3-ethylcarbodiimide, 1-(3-dimethylaminopropyl)-3-ethylcarbodiimide hydrochloride, N,N-dicyclohexylcarbodiimide, 1,1'-carbonyldiimidazole, etc. Further, an additive, such as N-hydroxysuccinimide, 4-(dimethylamino)pyridine (DMAP) or 1-hydroxybenzotrizole hydrate, may be added to the reaction system in an amount of 0.1 to 10 equivalents based on Compound (C), for promoting the reaction.

In the case where an acid addition salt of Compound (III) is used, the reaction with Compound (C) can be carried out in the presence of a base in an amount of 0.1 equivalents or more, preferably 1 to 20 equivalents, for example, an amine such as pyridine, triethylamine, diisopropylethylamine or N,N-diethylaniline. Preferably, triethylamine is used in the reaction. Compound (II), the corresponding substituted or unsubstituted heterocyclic compound, or Compound (III) or the acid addition salt of Compound (III), and the condensing agent may be used in an amount of 0.1 equivalents or more, preferably 1 to 10 equivalents based on Compound (C), respectively. The reaction is generally carried out at a temperature between −20° C. and 80° C., preferably between 0° C. and 60° C. for 5 minutes to 48 hours.

Step 1-1b:

Compound (D) can also be obtained by reacting an acid halide, which is obtained by reacting Compound (C) with a halogenating agent, with Compound (II), a corresponding substituted or unsubstituted heterocyclic compound, or Compound (III) or an acid addition salt of Compound (III), in the presence or absence of a base.

Examples of the halogenating agent to be used for halogenating Compound (C) include thionyl chloride, thionyl bromide, oxalyl chloride, phosphorus trichloride, phosphorus pentachloride, etc. Examples of the solvent in the reaction of Compound (C) with the halogenating agent include THF, toluene, dichloromethane, chloroform, etc., which may be used alone or as a mixture thereof. The halogenating agent may be used in an amount of 0.1 equivalents or more, preferably 1 to 20 equivalents based on Compound (C), or can also be used as the solvent when the halogenating agent is liquid. The reaction of Compound (C) with the halogenating agent is generally carried out at a temperature between −20° C. and 120° C., preferably between 0° C. and 100° C. for 5 minutes to 48 hours.

Examples of the solvent in the reaction of the acid halide of Compound (C) with Compound (II), the corresponding substituted or unsubstituted heterocyclic compound, or Compound (III) or the acid addition salt of Compound (III)

include THF, acetone, toluene, dichloromethane, water, methanol, DMF, etc., which may be used alone or as a mixture thereof. Examples of the base include potassium carbonate, sodium carbonate, sodium hydrogencarbonate, sodium hydroxide, potassium hydroxide, pyridine, triethylamine, diisopropylethylamine, N,N-diethylaniline, DMAP, etc., and may be used in an amount of 0.1 equivalents or more, preferably 1 to 20 equivalents, or can also be used as the solvent when the base is liquid. Compound (II), the corresponding substituted or unsubstituted heterocyclic compound, or Compound (III) or the acid addition salt of Compound (III) may be used in an amount of 0.1 equivalents or more, preferably 1 to 50 equivalents based on Compound (C), respectively. The reaction is generally carried out at a temperature between −20° C. and 180° C., preferably between −20° C. and 100° C. for in 30 minutes to 48 hours.

Compound (C), in which the protecting group ($P^1$) at 3-position is an acetyl group, can be converted into Compound (E) in one step by amidation or esterification as described above wherein the acetyl group of Compound (C) can be removed.

Step 1-2a:

Compound (E) can be obtained by treating Compound (D), in which $P^1$ is methyl, with a deprotecting agent.

Examples of the solvent include dichloromethane, chloroform, 1,2-dichloroethane, DMF, etc., which may be used alone or as a mixture thereof, or no solvent may be used when the deprotecting agent is liquid.

Examples of the deprotecting agent include boron tribromide, iodotrimethylsilane, sodium ethanethiolate, hydrobromic acid in acetic acid, etc.

The deprotecting agent may be used in an amount of 0.1 equivalents or more, preferably 1 to 20 equivalents based on Compound (D). The reaction is generally carried out at a temperature between −78° C. and 180° C., preferably between −20° C. and 120° C. for 10 minutes to 48 hours.

Step 1-2b:

Compound (E) can also be obtained by treating Compound (D), in which $P^1$ is an acetyl group, with an acid or a base.

Examples of the solvent include THF, methanol, ethanol, water, acetone, DMF, toluene, dichloromethane, chloroform, etc., which may be used alone or as a mixture thereof.

Examples of the acid include hydrochloric acid, hydrobromic acid, etc.; and examples of the base include potassium carbonate, sodium carbonate, sodium hydrogencarbonate, sodium hydroxide, potassium hydroxide, sodium ethoxide, aqueous ammonia, diethylamine, pyrrolidine, n-propylamine, etc.

The acid or the base may be used in an amount of 0.1 equivalents or more, preferably 1 to 20 equivalents based on Compound (D), or can also be used as the solvent. The reaction is generally carried out at a temperature between −20° C. and 180° C., preferably between 0° C. and 120° C. for 5 minutes to 48 hours.

Further, the order of Step 1-1a or 1-1b and Step 1-2a or 1-2b may be reversed to give Compound (E) from Compound (C). Concretely, the 3-position of Compound (C) is deprotected in a manner similar to that in Step 1-2a or 1-2b, and thereafter the carboxyl group at 17-position of the thus-deprotected compound is esterified or amidated in a manner similar to that in Step 1-1a or 1-1b to give Compound (E).

Step 1-3:

Compound (Ia) can be obtained by reacting Compound (E) with Compound (IV) represented by $R^{1a}R^{2a}NSO_2Cl$ (wherein $R^{1a}$ and $R^{2a}$ have the same meanings as defined above, respectively) in the presence or absence of a base.

Examples of the solvent include THF, DMF, N,N-dimethylacetamide (DMAC), 1,3-dimethyl-2-imidazolidinone, toluene, dichloromethane, chloroform, 1,2-dichloroethane, 1-methyl-2-piperidone, etc., which may be used alone or as a mixture thereof.

Examples of the base include sodium hydride, potassium carbonate, sodium carbonate, sodium hydrogencarbonate, cesium carbonate, lithium hydroxide, potassium tert-butoxide, 2,6-di-tert-butyl-4-methylpyridine, pyridine, 2,6-di-tert-butylpyridine, 2,6-lutidine, triethylamine, diisopropylethylamine, 4-(dimethylamino)pyridine, etc. Preferred is sodium hydride or 2,6-di-tert-butyl-4-methylpyridine. In case where the base is liquid, it may also be used as the solvent.

The base and Compound (IV) may be used in an amount of 0.1 equivalents or more, preferably 1 to 20 equivalents based on Compound (E), respectively. The reaction is generally carried out at a temperature between −78° C. and 120° C., preferably between −20° C. and 60° C. for 5 minutes to 72 hours.

Production Method 2

Compound (Ib) can be obtained from Compound (F), which is obtained from estrone in a method similar to a known method [e.g., *Chemische Berichte*, Vol. 111, p. 3094 (1978); WO99/33858], according to the reaction process described below.

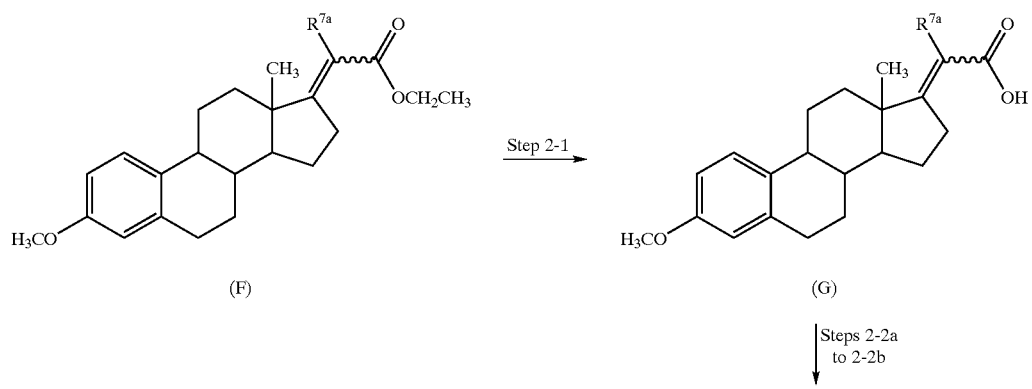

-continued

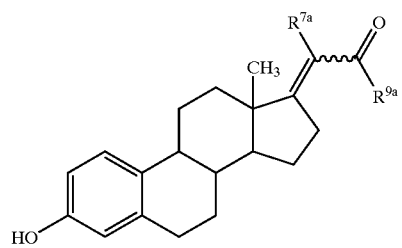

(J)

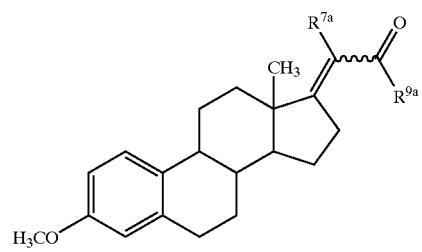

(H)

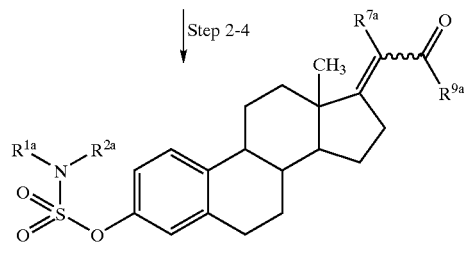

(Ib)

[Wherein $R^{1a}$ and $R^{2a}$ have the same meanings as defined above, respectively; $R^{7a}$ has the same meaning as defined for $R^7$ above; $R^{9a}$ represents $OR^{10}$ (wherein $R^{10}$ has the same meaning as defined above), a substituted or unsubstituted heterocyclic group bonding to the adjacent carbonyl group via its N, or $NR^{11}R^{12}$ (wherein $R^{11}$ and $R^{12}$ have the same meanings as defined above, respectively].

Step 2-1:

Compound (G) can be obtained by treating Compound (F) with an acid or a base.

Examples of the solvent include THF, methanol, ethanol, water, acetone DMF, toluene, dichlorometh,ane, chloroform, etc., which may be used alone or as a mixture thereof.

Examples of the acid include hydrochloric acid, hydrobromic acid, etc.; and examples of the base include lithium hydroxide, sodium hydroxide, potassium hydroxide, sodium ethoxide, etc.

The acid or the base may be used in an amount of 0.1 equivalents or more, preferably 1 to 50 equivalents based on Compound (F), or can also be used as the solvent when the acid or the base are liquid. The reaction is generally carried out at a temperature between −20° C. and 180° C., preferably between 0° C. and 1200C for 5 minutes to 48 hours.

Step 2-2a:

Compound (H) can be obtained by reacting Compound (G) with Compound (V) represented by $HOR^{10}$ (wherein $R^{10}$ has the same meaning as defined above), a corresponding substituted or unsubstituted heterocyclic compound, or Compound (VI) represented by $HNR^{11}R^{12}$ (wherein $R^{11}$ and $R^{12}$ have the same meanings as defined above, respectively) or an acid addition salt of Compound (VI) in the presence of a condensing agent in a manner similar to that in Step 1-1a of Production Method 1.

Step 2-2b:

Compound (H) can also be obtained by reacting an acid halide which is obtained by reacting Compound (G) with a halogenating agent, with Compound (V), a corresponding substituted or unsubstituted heterocyclic compound, or Compound (VI) or an acid addition salt of Compound (VI) in the presence or absence of a base in a manner similar to that in Step 1-1b of Production Method 1.

Step 2-3:

Compound (J) can be obtained by treating Compound (H) with a deprotecting agent in a manner similar to that in Step 1-2a of Production Method 1.

Step 2-4:

Compound (Ib) can be obtained by reacting Compound (J) with Compound (IV) in the presence or absence of a base in a manner similar to that in Step 1-3 of Production Method 1.

Production Method 3

Compound (Ic) can be obtained from Compound (F) according to the reaction process described below.

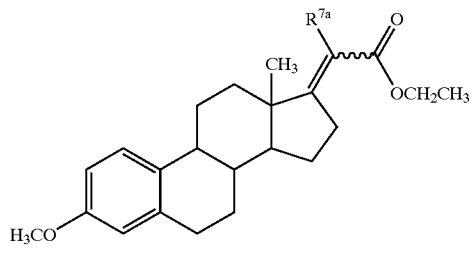

(F)

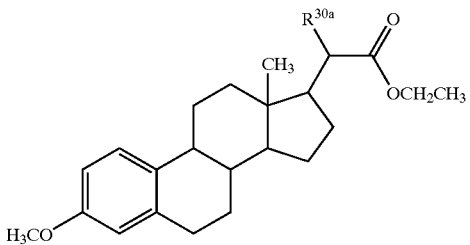

(K)

Step 3-1

Step 3-2

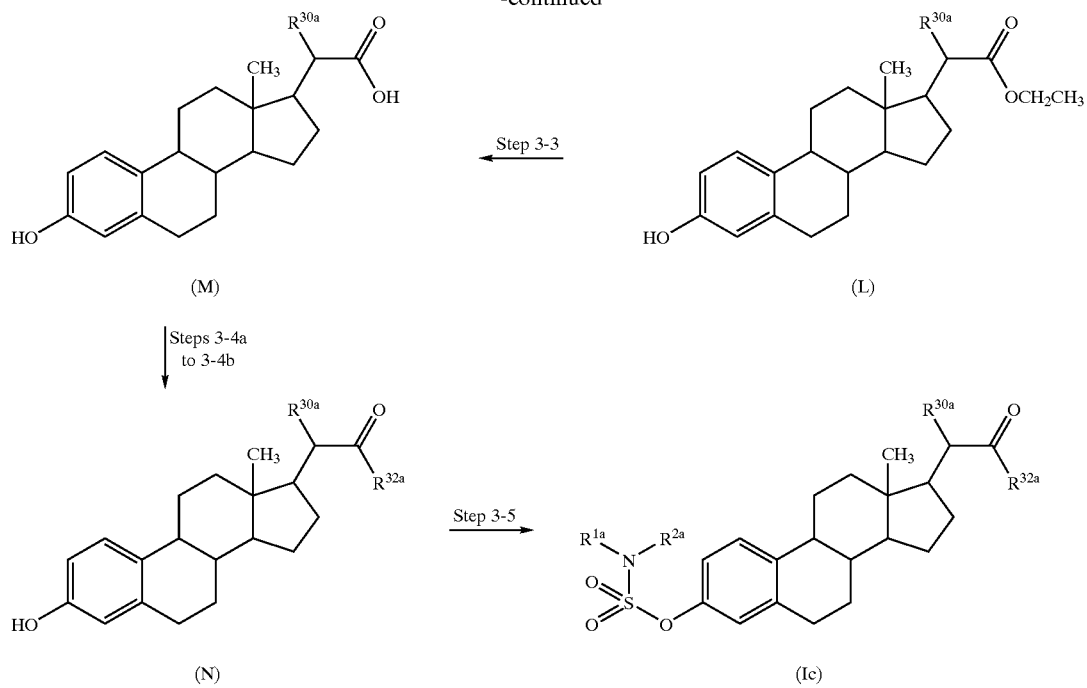

[wherein $R^{1a}$, $R^{2a}$ and $R^{7a}$ have the same meanings as defined above, respectively; $R^{30a}$ has the same meaning as defined for $R^{30}$ above; $R^{32a}$ represents $OR^{33a}$ (wherein $R^{33a}$ represents a substituted or unsubstituted alkyl group, a substituted or unsubstituted lower cycloalkyl group, a substituted or unsubstituted aryl group, or a substituted or unsubstituted heterocyclic group), a substituted or unsubstituted heterocyclic group bonding to the adjacent carbonyl group via its N, or $NR^{34}R^{35}$ (wherein $R^{34}$ and $R^{35}$ have the same meanings as defined above, respectively)].

Step 3-1:

Compound (K) can be obtained by catalytic reduction of Compound (F).

Examples of the solvent include ethyl acetate, methanol, ethanol, water, DMF, acetic acid, etc., which may be used alone or as a mixture thereof.

Examples of a reducing catalyst include 10% palladium on carbon, platinum dioxide, Raney nickel, etc. The reaction is carried out in hydrogen under atmospheric pressure to a few atmospheric pressure, or in the presence of a hydrogen source such as ammonium formate or hydrazine in an amount of 0.1 equivalents or more, preferably 1 to 20 equivalents.

The reducing catalyst may be used in an amount of 0.5 to 200% based on Compound (F). The reaction is generally carried out at a temperature between −20° C. and 180° C., preferably between 0° C. and 80° C. for 10 minutes to 48 hours.

Step 3-2:

Compound (L) can be obtained by treating Compound (K) with a deprotecting agent in a manner similar to that in Step 1-2a of Production Method 1.

Step 3-3:

Compound (M) can be obtained by treating Compound (L) with an acid or a base in a manner similar to that in Step 2-1 of Production Method 2.

Step 3-4a:

Compound (N) can be obtained by reacting Compound (M) with Compound (VII) represented by $HOR^{33a}$ (wherein $R^{33a}$ has the same meaning as defined above, respectively), a corresponding substituted or unsubstituted heterocyclic compound, or Compound (VIII) represented by $HNR^{34}R^{35}$ (wherein $R^{34}$ and $R^{35}$ have the meanings as defined above, respectively) or an acid addition salt of Compound (VIII) in the presence of a condensing agent in a manner similar to that in Step 1-1a of Production Method 1.

Step 3-4b:

Compound (N) can also be obtained by reacting an acid halide, which is obtained by reacting Compound (M) with a halogenating agent, with Compound (VII), a corresponding substituted or unsubstituted heterocyclic compound, or Compound (VIII) or an acid addition salt of Compound (VIII) in the presence or absence of a base in a manner similar to that in Step 1-1b of Production Method 1.

Step 3-5:

Compound (Ic) can be obtained by reacting Compound (N) with Compound (IV) in the presence or absence of a base in a manner similar to that in Step 1-3 of Production Method 1.

Production Method 4

Compound (Id) can be obtained from Compound (O) or Compound (L), which is obtained in a method similar to a known method (e.g., WO99/33858) or through demethylation at 3-position of Compound (F), according to the reaction process described below.

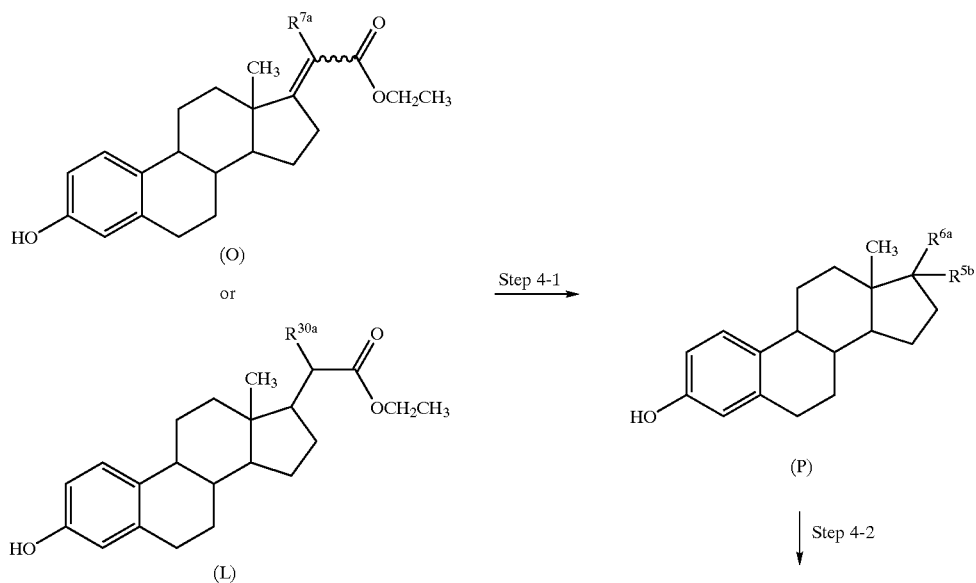

[wherein $R^{1a}$, $R^{2a}$, $R^{7a}$ and $R^{30a}$ have the same meanings as defined above, respectively; $R^{5b}$ represents a hydrogen atom, or is combined with $R^{6a}$ to form $=CR^{7a}R^{8a}$ (wherein $R^{7a}$ has the same meaning as defined above, and $R^{8a}$ represents CHO or CH$_2$OH); and $R^{6a}$ represents CHR$^{30a}$R$^{31a}$ (wherein $R^{30a}$ has the same meaning as defined above, and $R^{31a}$ represents CHO or CH$_2$OH), or is combined with $R^{5b}$ to form $=CR^{7a}R^{8a}$ (wherein $R^{7a}$ and $R^{8a}$ have the same meanings as defined above, respectively)].

Step 4-1:

Compound (P) can be obtained by reacting Compound (O) or Compound (L) with a metal hydride.

Examples of the solvent include THF, ether, toluene, etc., which may be used alone or as a mixture thereof. Examples of the metal hydride include diisobutylaluminum hydride, sodium bis(2-methoxyethoxy)aluminum hydride, lithium aluminum hydride, sodium triethoxyaluminum hydride, lithium triethoxyaluminum hydride, sodium diethoxyaluminum hydride, etc.

The metal hydride may be used in an amount of 0.1 equivalents or more, preferably 0.3 to 5 equivalents based on Compound (O) or Compound (L). The reaction is generally carried out at a temperature between −78° C. and 100° C., preferably between −78° C. and 40° C. for 5 minutes to 72 hours.

Step 4-2:

Compound (Id) can be obtained by reacting Compound (P) with Compound (IV) in the presence or absence of a base in a manner similar to that in Step 1-3 of Production Method 1.

Production Method 5

Compound (Ie) can be obtained from Compound (Q), which is obtained from Compound (C), Compound (L) or Compound (O) in a manner similar to those in Production Methods 1 to 4, according to the reaction process described below.

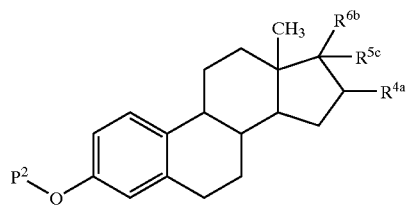 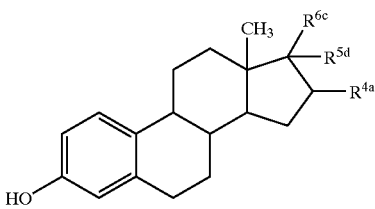

(Q)    (R)

Step 5-1

Step 5-2

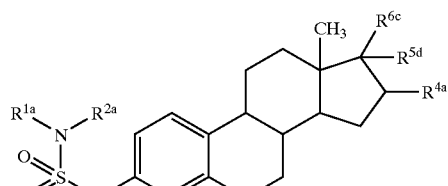

(Ie)

{wherein $R^{1a}$, $R^{2a}$ and $R^{4a}$ have the same meanings as defined above, respectively; $R^{5C}$ represents a hydrogen atom, or is combined with $R^{4a}$ to form a bond, or is combined with $R^{6b}$ to form $=CR^{7a}COR^{9b}$ (wherein $R^{7a}$ has the same meaning as defined above, and $R^{9b}$ represents a hydrogen atom, a hydroxyl group or an ethoxy group); $R^{6b}$ represents $CHR^{30a}COR^{32b}$ (wherein $R^{30a}$ has the same meaning as defined above, and $R^{32b}$ has the same meaning as defined for $R^{9b}$ above), or $COR^{53b}$ (wherein $R^{53b}$ has the same meaning as defined for $R^{9b}$ above), or is combined with $R^{5c}$ to form $=CR^{7a}COR^{9b}$ (wherein $R^{7a}$ and $R^{9b}$ have the same meanings as defined above, respectively); $R^{5d}$ represents a hydrogen atom, or is combined with $R^{4a}$ to form a bond, or is combined with $R^{6c}$ to form $=CR^{7a}R^{8b}$ [wherein $R^{7a}$ has the same meaning as defined above, and $R^{8b}$ represents $COR^{9c}$ (wherein $R^{9c}$ represents a substituted or unsubstituted lower alkyl group, a substituted or unsubstituted lower cycloalkyl group, a substituted or unsubstituted aryl group, or a substituted or unsubstituted heterocyclic group), or $CR^{19a}R^{20a}(OH)$ (wherein $R^{19a}$ and $R^{20a}$ have the same meanings as defined for $R^{19}$ and $R^{20}$ above, respectively)]; $R^{6c}$ represents $CHR^{30a}R^{31b}$ [wherein $R^{30a}$ has the same meaning as defined above, and $R^{31b}$ represents $COR^{32c}$ (wherein $R^{32c}$ represents a substituted or unsubstituted lower alkyl group, a substituted or unsubstituted lower cycloalkyl group, a substituted or unsubstituted aryl group, or a substituted or unsubstituted heterocyclic group), or $CR^{42a}R^{43a}(OH)$ (wherein $R^{42a}$ and $R^{43a}$ have the same meanings as defined for $R^{42}$ and $R^{43}$ above, respectively)], $COR^{53c}$ (wherein $R^{53c}$ represents a substituted lower alkyl group, a substituted lower cycloalkyl group, a substituted or unsubstituted aryl group, or a substituted or unsubstituted heterocyclic group), or $CR^{71a}R^{72a}(OH)$ (wherein $R^{71a}$ and $R^{72a}$ have the same meanings as defined for $R^{71}$ and $R^{72}$ above, respectively), or is combined with $R^{5d}$ to form $=CR^{7a}R^{8b}$ (wherein $R^{7a}$ and $R^{8b}$ have the same meanings as defined above, respectively); and $P^2$ represents a hydrogen atom or an acetyl group}

Step 5-1:

Compound (R) can be obtained by reacting Compound (Q) with an organometallic reagent such as an organic Grignard reagent or an organolithium reagent having the intended functional group.

Examples of the solvent include THF, ether, toluene, dichloromethane, etc., which may be used alone or as a mixture thereof.

The organometallic reagent may be used in an amount of 0.1 equivalents or more, preferably 1 to 10 equivalents based on Compound (Q). The reaction is generally carried out at a temperature between −78° C. and 120° C., preferably between −78° C. and 60° C. for 10 minutes to 72 hours.

When Compound (Q) wherein $P^2$ is an acetyl group could not be deacetylated under the above reaction condition, Compound (Q) can be converted into Compound (R) in a manner similar to that in Step 1-2b of Production Method 1.

Step 5-2:

Compound (Ie) can be obtained by reacting Compound (R) with Compound (IV) in the presence or absence of a base in a manner similar to that in Step 1-3 of Production Method 1.

Production Method 6

Compound (If) can be obtained from Compound (S), which is obtained in a manner similar to a known method [e.g., *The Journal of Organic Chemistry*, Vol. 59, p. 6683 (1994)], Compound (W) or estrone, according to the reaction process described below. Compound (W) can be produced in a manner similar to a method for producing Compound (P) or Compound (R).

27

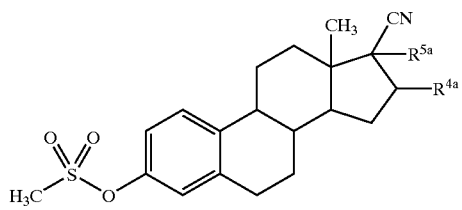

(S)

Step 6-1 →

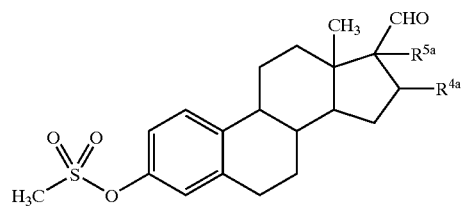

(T)

Step 6-2 ↓

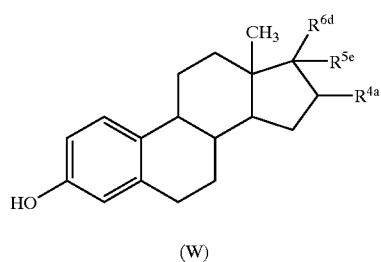

(W)

Estrone

Step 6-5 ↘    Step 6-4 ↓    Step 6-3 ↙

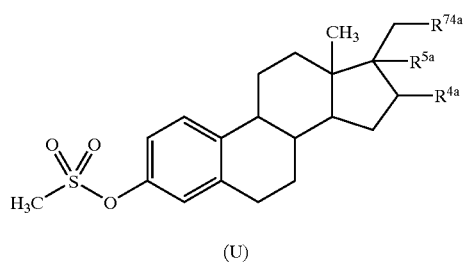

(U)

28

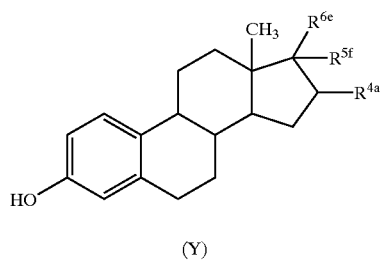

(Y)

Step 6-6 →

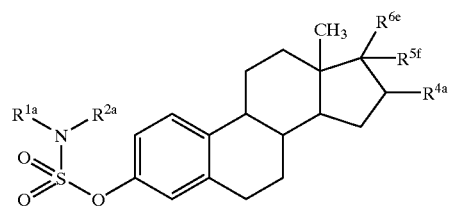

(If)

{wherein $R^{1a}$, $R^2a$, $R^{4a}$ and $R^{5a}$ have the same meanings as defined above, respectively; $R^{5e}$ represents a hydrogen atom, or is combined with $R^{4a}$ to form a bond, or is combined with $R^{6d}$ to form $=CR^{7a}COR^{9d}$ (wherein $R^{7a}$ has the same meaning as defined above, and $R^{9d}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group); $R^{6d}$ represents $CHR^{30a}COR^{32d}$ (wherein $R^{30a}$ has the same meaning as defined above, and $R^{32d}$ has the same meaning as defined for $R^{9d}$ above) or $COR^{53d}$ (wherein $R^{53d}$ represents a substituted lower alkyl group, a substituted lower cycloalkyl group, a substituted or unsubstituted aryl group, or a substituted or unsubstituted heterocyclic group), or is combined with $R^{5e}$ to form $=CR^{7a}COR^{9d}$ (wherein $R^{7a}$ and $R^{9d}$ have the same meanings as defined above, respectively); $R^{5f}$ represents a hydrogen atom, or is combined with $R^{4a}$ to form a bond, or is combined with $R^{6e}$ to form $=CR^{7a}CHR^{21a}R^{22a}$ [wherein $R^{7a}$ has the same meaning as defined above, $R^{21a}$ has the same meaning as defined for $R^{9d}$ above, and $R^{22a}$ represents $NR^{23a}R^{24a}$ (wherein $R^{23a}$ and $R^{24a}$ are the same or different and represent a hydrogen atom, a substituted or unsubstituted lower alkyl group, a substituted or unsubstituted lower cycloalkyl group, a substituted or unsubstituted aryl group, or a substituted or unsubstituted heterocyclic group, or $R^{23a}$ and $R^{24a}$ are combined with N adjacent thereto to form a nitrogen-containing heterocyclic group)]; $R^{6e}$ represents $CHR^{30a}CHR^{44a}R^{45a}$ (wherein $R^{30a}$ has the same meaning as defined above, $R^{44a}$ has the same meaning as defined for $R^{9d}$ above, and $R^{45a}$ has the same meaning as defined for $R^{22a}$ above), $CHR^{73a}R^{74b}$ (wherein $R^{73a}$ represents a hydrogen atom, a substituted lower alkyl group, a substituted lower cycloalkyl group, a substituted or unsubstituted aryl group, or a substituted or unsubstituted heterocyclic group, and $R^{74b}$ has the same meaning as defined for $R^{22a}$ above), or $NR^{82a}R^{83a}$ (wherein $R^{82a}$ and $R^{83a}$ are the same or different and represent a hydrogen atom, a substituted or unsubstituted lower alkyl group, a substituted or unsubstituted lower cycloalkyl group, a substituted or unsubstituted aryl group, or a substituted or unsubstituted heterocyclic group, or $R^{82a}$ and $R^{83a}$ are combined with N adjacent thereto to form a nitrogen-containing heterocyclic group), or $R^{6e}$ is combined with $R^{5f}$ to form =$CR^{7a}CHR^{21a}R^{22a}$ (wherein $R^{7a}$, $R^{21a}$ and $R^{22a}$ have the same meanings as defined above, respectively); and $R^{74a}$ has the same meaning as defined for $R^{22a}$ above}.

Step 6-1:

Compound (T) can be obtained by reacting Compound (S) with a metal hydride in a manner similar to that in Step 4-1 of Production Method 4.

Step 6-2:

Compound (U) can be obtained by reacting Compound (T) with Compound (IX) represented by $HNR^{23a}R^{24a}$ (wherein $R^{23a}$ and $R^{24a}$ have the same meanings as defined above, respectively) in a solvent in the presence of a reducing agent.

Examples of the solvent include methanol, ethanol, dichloromethane, 1,2-dichloroethane, THF, ether, toluene, water, etc., which may be used alone or as a mixture thereof.

Examples of the reducing agent include sodium cyanoborohydride, sodium triacetoxyborohydride, lithium aluminum hydride, sodium borohydride, diborane, etc. The reaction can also be carried out in the presence of an acid such as acetic acid or hydrochloric acid in an amount of 0.1 equivalents or more, preferably 0.1 to 20 equivalents based on Compound (T).

The reducing agent and Compound (IX) may be used in an amount of 0.1 equivalents or more, preferably 1 to 20 equivalents based on Compound (T), respectively. The reaction is generally carried out at a temperature between −78° C. and 120° C., preferably between 0° C. and 60° C. for 5 minutes to 72 hours.

Step 6-3:

Compound (Y) wherein $R^{5f}$ has the same meaning as defined for $R^{5a}$ above, and $R^{6e}$ is $CH_2R^{74a}$ (wherein $R^{74a}$ has the same meaning as defined above) can be obtained by treating Compound (U) with a base.

Examples of the solvent include THF, methanol, ethanol, water, acetone, DMF, toluene, dichloromethane, chloroform, etc., which may be used alone or as a mixture thereof.

Examples of the base include potassium carbonate, sodium hydroxide, potassium hydroxide, sodium ethoxide, etc. The base may be used in an amount of 0.1 equivalents or more, preferably 1 to 50 equivalents based on Compound (U). The reaction is generally carried out at a temperature between −20° C. and 180° C., preferably between 0° C. and 120° C. for 5 minutes to 48 hours.

Step 6-4:

Compound (Y) wherein $R^{6e}$ is $CHR^{30a}CHR^{44a}R^{45a}$ (wherein $R^{30a}$, $R^{44a}$ and $R^{45a}$ have the same meanings as defined above, respectively) or $CHR^{73a}R^{74b}$ (wherein $R^{73a}$ and $R^{74b}$ have the same meanings as defined above, respectively), or is combined with $R^{5f}$ to form =$CR^{7a}CHR^{21a}R^{22a}$ (wherein $R^{7a}$, $R^{21a}$ and $R^{22a}$ have the same meanings as defined above, respectively), can be obtained by reacting Compound (W) with Compound (IX) in the presence of a reducing agent in a manner similar to that in Step 6-2 of Production Method 6.

Step 6-5:

Compound (Y) wherein $R^{4a}$ and $R^{5f}$ are both hydrogen atoms, and $R^6$ is $NR^{82a}R^{83a}$ (wherein $R^{82a}$ and $R^{83a}$ have the same meanings as defined above, respectively) can be obtained by reacting estrone with Compound (X) represented by $HNR^{82a}R^{83a}$ (wherein $R^{82a}$ and $R^{83a}$ have the same meanings as defined above, respectively) in the presence of a reducing agent in a manner similar to that in Step 6-2 of Production Method 6.

Step 6-6:

Compound (If) can be obtained by reacting Compound (Y) with Compound (IV) in the presence or absence of a base in a manner similar to that in Step 1-3 of Production Method 1.

Production Method 7

Compound (Ig) can be obtained from Compound (Z), which is obtained from estrone 3-acetate in a manner similar to a known method [e.g., *Tetrahedron Letters*, Vol. 26, p. 1109 (1985); *Tetrahedron Letters*, Vol. 33, p. 3939 (1992)], according to the reaction process described below.

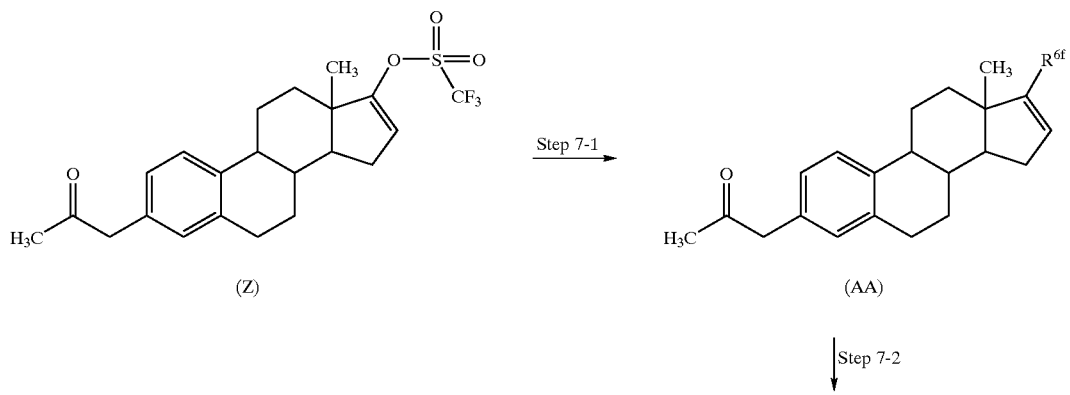

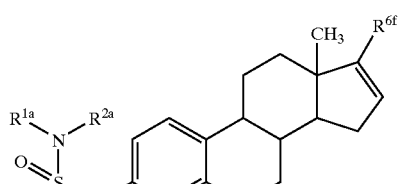

(Ig)

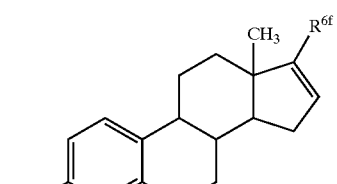

(BB)

(wherein $R^{1a}$ and $R^{2a}$ have the same meanings as defined above, respectively; and $R^{6f}$ represents a substituted or unsubstituted aryl group, or a substituted or unsubstituted heterocyclic group)

Step 7-1:

Compound (AA) can be obtained by reacting Compound (Z) with a boron compound or a tin compound having the intended functional group in the presence of a palladium catalyst.

Examples of the solvent include 1,4-dioxane, THF, DMF, ether, dimethyl sulfoxide (DMSO), toluene, water, methanol, dimethoxyethane, etc., which may be used alone or as a mixture thereof.

Examples of the palladium catalyst include dichlorobis(triphenylphosphine)palladium(II) [$PdCl_2(PPh_3)_2$], tetrakis(triphenylphosphine)palladium(0) [$Pd(PPh_3)_4$], dichlorobis[1,1-bis(diphenylphosphanyl)ferrocene]palladium(II) [$PdCl_2(dppf)$], palladium acetate(II) [$Pd(OAc)_2$], etc. And also, the reaction can be carried out in the presence of a base in an amount of 0.1 equivalents or more, preferably 0.5 to 5 equivalents. Examples of the base include sodium hydroxide, sodium carbonate, potassium carbonate, cesium carbonate, barium hydroxide, sodium ethoxide, triethylamine, etc.

The palladium catalyst may be used in an amount of 0.001 equivalents or more, preferably 0.005 to 1 equivalent based on Compound (Z); and the boron compound or the tin compound may be used in an amount of 0.1 equivalents or more, preferably 1 to 5 equivalents based on Compound (Z). The reaction is generally carried out at a temperature between −78° C. and 180° C., preferably between 0° C. and 120° C. for 10 minutes to 72 hours.

Through the coupling reaction as described above, Compound (Z) can also be converted into Compound (BB) in one step.

Step 7-2:

Compound (BB) can be obtained bytreating Compound (AA) with an acid or a base in a manner similar to that in Step 1-2b of Production Method 1.

Step 7-3:

Compound (Ig) can be obtained by reacting Compound (BB) with Compound (IV) in the presence or absence of a base in a manner similar to that in Step 1-3 of Production Method 1.

Production Method 8

Compound (Ih) can be obtained from Compound (CC), which is obtained by amidation of Compound (C), Compound (M) or Compound (G) which are deprotected at 3-position, in a manner similar to that in Step 1-1a or 1-1b of Production Method 1, according to the reaction process described below.

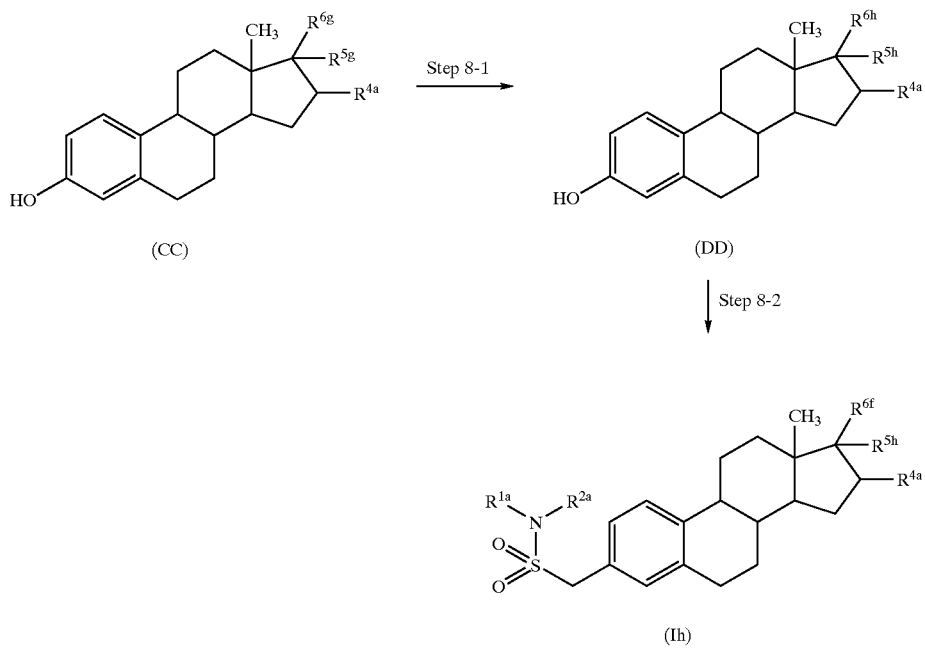

[wherein $R^{1a}$, $R^{2a}$ and $R^{4a}$ have the same meanings as defined above, respectively; $R^{5g}$ represents a hydrogen atom, or is combined with $R^{4a}$ to form a bond, or is combined with $R^{6g}$ to form $=CR^{7a}CONH_2$ (wherein $R^{7a}$ has the same meaning as defined above); $R^{6g}$ represents $CONH_2$ or $CHR^{30a}CONH_2$ (wherein $R^{30a}$ has the same meaning as defined above), or is combined with $R^{5g}$ to form $=CR^{7a}CONH_2$ (wherein $R^{7a}$ has the same meaning as defined above); $R^{5h}$ represents a hydrogen atom, or is combined with $R^{4a}$ to form a bond, or is combined with $R^{6h}$ to form $=CR^{7a}R^{8c}$ (wherein $R^{7a}$ has the same meaning as defined above, and $R^{8c}$ represents a substituted or unsubstituted 2-oxazolyl group); and $R^{6h}$ represents a substituted or unsubstituted 2-oxazolyl group or $CHR^{30a}R^{31c}$ (wherein $R^{30a}$ has the same meaning as defined above, and $R^{31c}$ represents a substituted or unsubstituted 2-oxazolyl group), or is combined with $R^{5h}$ to form $=CR^{7a}R^{8c}$ (wherein $R^{7a}$ and $R^{8c}$ have the same meanings as defined above, respectively)].

Step 8-1:

Compound (DD) can be obtained by reacting Compound (CC) with an α-haloketone or an α-haloaldehyde having the intended functional group (the halogen is an iodine atom, a bromine atom or a chlorine atom).

Examples of the solvent include THF, methanol, ethanol, water, acetone, DMF, toluene, dichloromethane, chloroform, DMSO, etc., which may be used alone or as a mixture thereof.

The α-haloketone or the α-haloaldehyde may be used in an amount of 0.1 equivalents or more, preferably 1 to 20 equivalents based on Compound (CC). The reaction is generally carried out at a temperature between −20° C. and 180° C., preferably between 40° C. and 120° C. for 5 minutes to 48 hours.

Step 8-2:

Compound (Ih) can be obtained by reacting Compound (DD) with Compound (IV) in the presence or absence of a base in a manner similar to that in Step 1-3 of Production Method 1.

Production Method 9

Compound (Ii) can be obtained by sulfamoylating of Compound (EE).

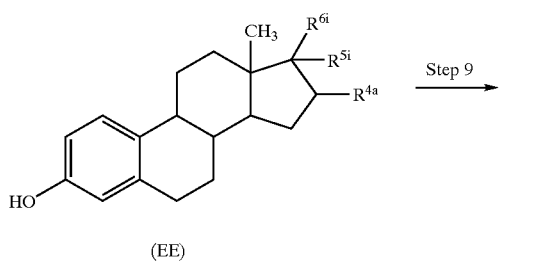

(EE)

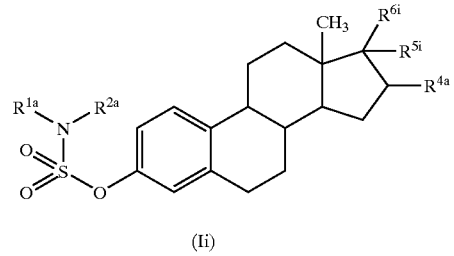

(Ii)

(wherein $R^{1a}$, $R^{2a}$ and $R^{4a}$ have the same meanings as defined above, respectively; and $R^{5i}$ and $R^{6i}$ have the same meanings as defined for $R^5$ and $R^6$ above, respectively)

Step 9:

Compound (Ii) can be obtained by reacting Compound (EE) with Compound (IV) in the presence or absence of a base in a manner similar to that in Step 1-3 of Production Method 1.

Production Method 10

Compound (Ik) can be obtained by catalytic reduction of Compound (Ij).

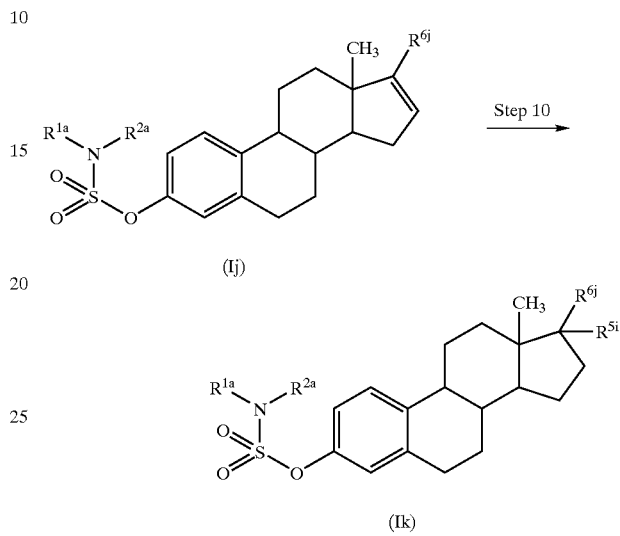

(Ij)

(Ik)

[wherein $R^{1a}$ and $R^{2a}$ have the same meanings as defined above, respectively; and $R^{6j}$ represents a cyano group, $CHR^{30a}R^{31d}$ (wherein $R^{30a}$ has the same meaning as defined above, and $R^{31d}$ has the same meaning as defined for $R^{31}$ above), $COR^{53e}$ (wherein $R^{53e}$ has the same meaning as defined for $R^{53}$ above), $CSR^{63a}$ (wherein $R^{63a}$ has the same meaning as defined for $R^{63}$ above), a substituted or unsubstituted aryl group, a substituted or unsubstituted heterocyclic group, $CR^{71a}R^{72a}(OH)$ (wherein $R^{71a}$ and $R^{72a}$ have the same meanings as defined above, respectively), or $CHR^{73a}R^{74c}$ (wherein $R^{73a}$ has the same meaning as defined above, and $R^{74c}$ has the same meaning as defined for $R^{74}$ above)].

Step 10:

Compound (Ik) can be obtained by catalytic reduction of Compound (Ij) in a manner similar to that in Step 3-1 of Production Method 3.

In Compound (Im) wherein $R^1$, $R^2$ and $R^3$ are combined to form an oxathiazine dioxide ring or a dihydroxathiazine dioxide ring, the oxathiazine dioxide ring or the dihydroxathiazine dioxide ring can be formulated in a manner similar to a known method (e.g., WO98/32763).

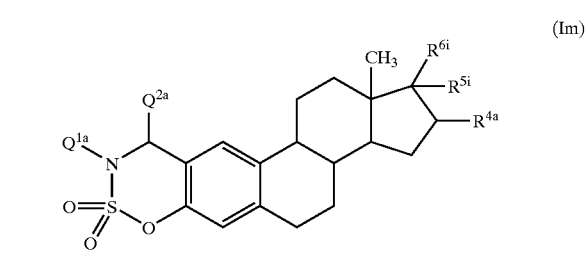

(Im)

(wherein $R^{4a}$, $R^{5i}$ and $R^{6i}$ have the same meanings as defined above, respectively; and $Q^{1a}$ and $Q^{2a}$ have the same meanings as defined for $Q^1$ and $Q^2$ above, respectively).

In production of Compound (I), the conversion of the functional groups in $R^1$, $R^2$, $R^3$, $R^4$, $R^5$ and $R^6$ may also be carried out in any other known methods [e.g., *Comprehensive Organic Transformations* written by R. C. Larock (1989)] than those described above.

The intermediates and intended products in the above-described production methods can be isolated or purified by a suitable combination of techniques used in ordinary organic synthesis, such as filtration, extraction, washing, drying, concentration, crystallization, and various kinds of chromatography. Further, the intermediates can also be subjected to the subsequent reaction without purification.

In the case where a salt of Compound (I) is desired, when Compound (I) is obtained in the form of the salt, it may be directly purified, while when Compound (I) is obtained in its free form, it may be dissolved or suspended in a suitable solvent, and converted into the salt by addition of an acid or a base thereto.

Compound (I) or pharmaceutically acceptable salts thereof as the active ingredient of the present invention may exist in the form of adducts with water or various solvents, and these adducts also fall under the scope of the present invention.

Examples of Compound (I) are shown in Tables 1 to 5.

TABLE 1-(1)

Examples of Compound (I)

| Compound No. | $R^{53}$ |
|---|---|
| 1 |  |
| 2 |  |
| 3 | 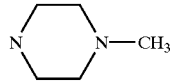 |
| 4 | 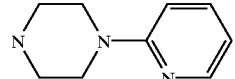 |
| 5 | 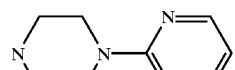 |
| 6 | 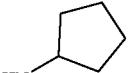 |

TABLE 1-(1)-continued

Examples of Compound (I)

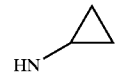

| Compound No. | $R^{53}$ |
|---|---|
| 7 | 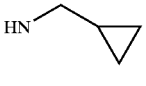 |
| 8 | 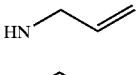 |
| 9 | 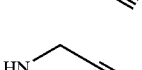 |
| 10 |  |
| 11 | 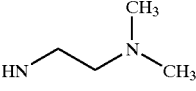 |
| 12 | 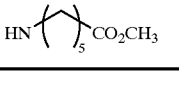 |
| 13 | 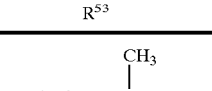 |
| 14 |  |

TABLE 1-(2)

Examples of Compound (I)

| Compound No. | $R^{53}$ |
|---|---|
| 15 |  |

TABLE 1-(2)-continued

Examples of Compound (I)

[Steroid structure with sulfamate group at position 3 and C(=O)-R⁵³ at position 17, with C16-C17 double bond]

| Compound No. | R⁵³ |
|---|---|
| 16 | HN-(CH₂)₅-C(=O)-NH-CH₃ |
| 17 | HN-CH₂CH₂-NH-C(=O)-CH₃ |
| 18 | HN-CH₂CH₂-OCH₃ |
| 19 | HN-CH₂CH₂-O-Si(CH₃)₂-C(CH₃)₃ |
| 20 | HN-CH₂CH₂-OH |
| 21 | HN-(CH₂)₄-O-Si(CH₃)₂-C(CH₃)₃ |
| 22 | HN-(CH₂)₄-OH |
| 23 | HN-C(CH₃)₂-CH₂OH |
| 24 | HN-CH₂-C(CH₃)₂-OH |
| 25 | HN-CH₂-CO₂H |
| 26 | HN-CH₂-CO₂CH₃ |
| 27 | HN-CH(CH₃)-CO₂H |
| 28 | HN-CH(CH(CH₃)₂... |

TABLE 1-(2)-continued

Examples of Compound (I)

[Same steroid structure]

| Compound No. | R⁵³ |
|---|---|
| 29 | HN-CH(CH(CH₃)₂)-CO₂CH₃ |
| 30 | HN-C(CH₃)₂-CO₂H |

TABLE 1-(3)

Examples of Compound (I)

[Same steroid structure]

| Compound No. | R⁵³ |
|---|---|
| 31 | HN-CH(Ph)-CO₂H |
| 32 | pyrrolidine-2-CO₂H (via NH) |
| 33 | pyrrolidine-2-CO₂CH₃ (via N) |
| 34 | HN-Ph |

TABLE 1-(3)-continued

Examples of Compound (I)

| Compound No. | R^53 |
|---|---|
| 35 | 3-(HN)-C6H4-CO2H |
| 36 | HN-CH2-C6H5 |
| 37 | 4-(HN-CH2)-C6H4-CO2H |
| 38 | 2-(HN)-pyridine |
| 39 | 5-(HN)-2-(OCH3)-pyridine |
| 40 | 2-(HN)-pyrazine |
| 41 | 2-(HN)-pyrimidine |
| 42 | 2-(HN-CH2)-pyridine |
| 43 | 3-(HN-CH2)-pyridine |
| 44 | 4-(HN-CH2)-pyridine |

TABLE 1-(4)

Examples of Compound (I)

| Compound No. | R^53 |
|---|---|
| 45 | 2-(HN-CH2)-5-CH3-pyridine |
| 46 | 2-(HN-CH2)-4-CH3-pyridine |
| 47 | 2-(HN-CH2)-4-(OCH3)-pyridine |
| 48 | 2-(HN-CH2)-pyrazine |
| 49 | 2-(HN-CH2)-5-CH3-pyrazine |
| 50 | 2-(HN-CH2CH2)-pyridine |
| 51 | 3-(HN-CH2CH2)-pyridine |
| 52 | 4-(HN-CH2CH2)-pyridine |
| 53 | 2-(HN-CH2CH2CH2)-pyridine |

TABLE 1-(4)-continued

Examples of Compound (I)

[Structure: steroid with CH₃, C(=O)R⁵³ at C17, double bond, and H₂N-S(=O)₂-O- at aromatic ring]

| Compound No. | R⁵³ |
|---|---|
| 54 | HN-CH₂CH₂CH₂-(pyridin-3-yl) |
| 55 | HN-CH₂CH₂CH₂-(pyridin-4-yl) |
| 56 | HN-CH₂CH₂CH₂-(pyrazin-2-yl) |
| 57 | HN-(thiazol-2-yl) |
| 58 | HN-(isoxazol-3-yl) |

TABLE 1-(5)

Examples of Compound (I)

[Same steroid structure with CH₃, C(=O)R⁵³, and H₂N-S(=O)₂-O-]

| Compound No. | R⁵³ |
|---|---|
| 59 | HN-(5-methylisoxazol-3-yl) |
| 60 | HN-(3,4-dimethylisoxazol-5-yl) |

TABLE 1-(5)-continued

Examples of Compound (I)

[Same steroid structure]

| Compound No. | R⁵³ |
|---|---|
| 61 | HN-(1,3,4-thiadiazol-2-yl) |
| 62 | HN-(1-ethyl-pyrazol-5-yl) |
| 63 | HN-(2H-tetrazol-5-yl) |
| 64 | HN-CH₂-(1,2,4-oxadiazol-3-yl) |
| 65 | HN-CH₂CH₂-(1-methyl-pyrrol-2-yl) |
| 66 | HN-CH₂CH₂CH₂-(imidazol-1-yl) |
| 67 | HN-CH₂CH₂CH₂-(2-oxopyrrolidin-1-yl) |
| 68 | HN-O-CH₂-(pyridin-2-yl) |
| 69 | HN-NH-(pyridin-2-yl) |
| 70 | O-CH₂CH₂-SO₂CH₃ |
| 71 | O-CH₂CH₂-O-CH₂CH₂-OCH₃ |
| 72 | (tetrahydro-2H-pyran-4-yl)-O- |

TABLE 2
Examples of Compound (I)
| Compound No. | R⁵³ |
|---|---|
| 73 | 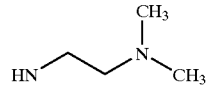 |
| 74 | 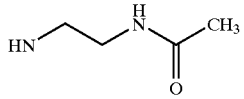 |
| 75 | 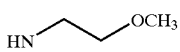 |
| 76 | 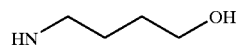 |
| 77 | 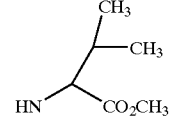 |
| 78 | 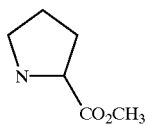 |
| 79 | 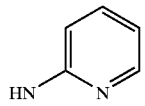 |
| 80 | 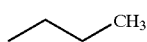 |
TABLE 3
Example of Compound (I)
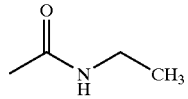
| Compound No. | R¹¹ |
|---|---|
| 81 | 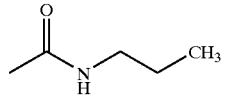 |
TABLE 4
Examples of Compound (I)
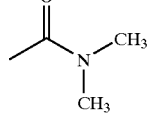
| Compound No. | R³¹ |
|---|---|
| 82 | CO₂H |
| 83 | CO₂CH₂CH₃ |
| 84 | 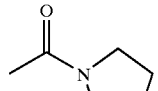 |
| 85 | 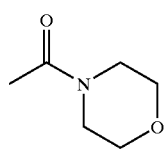 |
| 86 | 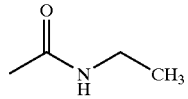 |
| 87 | 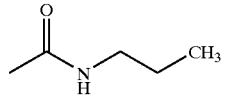 |
| 88 | 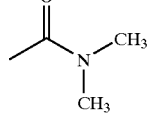 |

TABLE 5

Examples of Compound (I)

[Structure of estra-1,3,5(10)-triene sulfamate with R6 substituent at position 17, with H2N-S(=O)(=O)-O- group]

| Compound No. | R6 |
|---|---|
| 89 | -CH2CH2-N(morpholine) |
| 90 | -(3-pyridyl) |
| 91 | -C(CH3)2-OH |
| 92 | -(2-methyl-oxazol-4-yl with CH3) |
| 93 | -O-CH2-O-CH3 / -CH(CH3)-CON(H)-CH(CH3)2 |
| 94 | -CH(OH)-CH3 / -CON(H)-CH(CH3)2 with CH3 |
| 95 | -C(CO2H)(CH3)-CON(H)-CH(CH3)2 |

The pharmacological activity of some typical examples of Compound (I) is described with reference to the following Test Examples.

TEST EXAMPLE 1

Estrone Sulfatase (Steroid Sulfatase) Inhibition Test (Method A)

[6,7-$^3$H]-Estrone sulfate (final concentration 6.67 μmol/L; 0.025 μCi/tube), recombinant human estrone sulfatase (33 ng/tube) and an estra-1,3,5(10)-triene derivative of each test concentration (the estra-1,3,5(10)-triene derivative was dissolved in 0.003 mL of DMSO) were added to a phosphate buffer (pH 7.5, final volume 0.15 mL) containing 0.25 mol/L of sucrose and 0.04 mol/L of nicotinamide, and the mixture was subjected to enzymatic reaction at 37° C. for 30 minutes. The recombinant human estrone sulfatase used herein was prepared from CHO (Chinese hamster ovary) cells, which were transfected with a human estrone sulfatase gene, after partial purification. After the enzymatic reaction, toluene (0.5 mL) was added to the reaction mixture followed by stirring, and the mixture was centrifuged at 9000 rpm for 5 minutes. The toluene extract layer was taken out, and the radioactivity of the [$^3$H]-estrone formed therein was measured with a liquid scintillation counter. The measurement was carried out at one time by duplication, and the assay fluctuation was 10% or less. The enzymatic reaction in the absence of the test compound was also carried out simultaneously. The inhibitory activity against estrone sulfatase of the test compound of each concentration was calculated according to the equation shown below.

Inhibitory Activity against Estrone Sulfatase $(\%)=100-\{100\times[(A-C)/(B-C)]\}$ wherein;
A: the amount of [$^3$H]-estrone formed in the presence of the test compound
B: the amount of [$^3$H]-estrone formed in the absence of the test compound
C: the amount of [$^3$H]-estrone formed in the absence of both of the recombinant human estrone sulfatase and the test compound.

The inhibitory activity against estrone sulfatase of the estra-1,3,5(10)-triene derivative tested can be designated by the concentration ($IC_{50}$) of the derivative that reduces the estrone sulfatase activity to a half of that in the control system not containing the test compound.

TEST EXAMPLE 2

Estrone Sulfatase (Steroid Sulfatase) Inhibition Test (Method B)

4-Methylumbelliferyl sulfate (final concentration 0.3 mmol/L), recombinant human estrone sulfatase (7.8 ng/well) and an estra-1,3,5(10)-triene derivative of each test concentration (the estra-1,3,5(10)-triene derivative was dissolved in 0.001 mL of DMSO) were added to a phosphate buffer (pH 7.5, final volume 0.1 mL) containing 0.28 mol/L of sucrose and 0.04 mol/L of nicotinamide, and the mixture was subjected to enzymatic reaction at 37° C. for 1 hour. The recombinant human estrone sulfatase used herein was prepared from CHO (Chinese hamster ovary) cells, which were transfected with a human estrone sulfatase gene, after partial purification. After the enzymatic reaction, an aqueous solution of 2 mol/L glycine-sodium hydroxide (pH 10.3, 0.13 mL) was added thereto followed by stirring. Using a fluorescent plate reader (Cyto Fluor II), the fluorescent intensity of 4-methylumbelliferone formed in the system was measured. The measurement was carried out at one time by duplication, and the assay fluctuation was 10% or less. The enzymatic reaction in the absence of the test compound was also carried out simultaneously. The inhibitory activity against estrone sulfatase of the test compound of each concentration was calculated according to the equation shown below.

Inhibitory Activity against Estrone Sulfatase $(\%)=100-[100\times(A/B)]$ wherein;
A: the amount of 4-methylumbelliferone formed in the presence of the test compound,
B: the amount of 4-methylumbelliferone formed in the absence of the test compound.

The inhibitory activity against estrone sulfatase of the estra-1,3,5(10)-triene derivative tested can be designated by the concentration ($IC_{50}$) of the derivative that reduces the estrone sulfatase activity to a half of that in the control system not containing the test compound.

The results obtained in Test Example 1 (method A) and Test Example 2 (method B) are shown in Table 6.

TABLE 6

Inhibitory Activity against Steroid Sulfatase

| Compound No. | $IC_{50}$(nmol/L) | Test Method |
|---|---|---|
| 1 | 4.4 | A |
| 5 | 3.7 | B |
| 7 | 1.0 | A |
| 9 | 3.6 | A |
| 10 | 5.6 | A |
| 14 | 10.0 | A |
| 18 | 2.8 | A |
| 22 | 9.8 | A |
| 23 | 26.0 | B |
| 29 | 4.5 | A |
| 33 | 5.1 | A |
| 34 | 10.0 | A |
| 37 | 6.0 | B |
| 39 | 3.7 | B |
| 40 | 9.4 | A |
| 47 | 5.0 | B |
| 49 | 24.2 | B |
| 55 | 4.5 | B |
| 58 | 11.0 | B |
| 62 | 8.9 | B |
| 69 | 6.0 | B |
| 71 | 17.0 | B |
| 73 | 6.0 | A |
| 76 | 15.5 | A |
| 81 | 6.2 | A |
| 83 | 12.0 | B |
| 85 | 10.3 | B |
| 88 | 11.0 | B |
| 90 | 12.0 | B |
| 91 | 13.0 | B |
| 92 | 21.0 | B |

As shown in Table 6, Compound (I) shows inhibitory activity against steroid sulfatase and is useful for the treatment or the prevention of steroid hormone-dependent diseases.

Compound (I) or pharmaceutically acceptable salts thereof may be administered orally or parenterally as such or in the form of various pharmaceutical compositions. Examples of the form of these pharmaceutical compositions include tablets, powders, granules, injections, etc.

For formulating the forms as described above, generally known methods are employable. For example, the obtained preparations may contain any of various excipients, lubricants, binders, disintegrators, suspending agents, isotonicating agents, emulsifiers, absorption promoters, etc.

Examples of the carrier for the pharmaceutical compositions include water, distilled water for injection, physiological saline, glucose, fructose, white sugar, mannitol, lactose, starch, corn starch, cellulose, methyl cellulose, carboxymethyl cellulose, hydroxypropyl cellulose, alginic acid, talc, sodium citrate, calcium carbonate, calcium hydrogenphosphate, magnesium stearate, urea, silicone resin, sorbitan fatty acid esters, glycerin fatty acid esters, etc. These carriers are suitably selected depending on the type of the preparations.

The dosage and the frequency of administration of Compound (I) to be used for the purpose described above vary depending on the intended therapeutic or preventive effect, the administration method, the period of treatment, and also the age and the body weight of the patients to be treated, but it may be used by oral administration or parenteral administration (for example, through injection etc.) generally in a range of 0.01 to 20 mg/kg per day per adult, once a day or divided into several portions.

The structures of Compounds B1 to B23 used in Examples are shown in Table 7, Table 8, Table 9 and Table 10.

TABLE 7

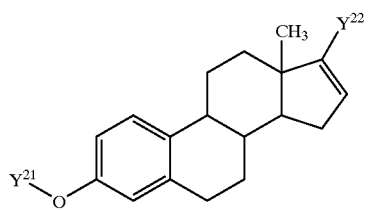

| Compound No. | $Y^{21}$ | $Y^{22}$ |
|---|---|---|
| B1 | $CH_3$ | $CO_2H$ |
| B2 | $COCH_3$ | $OSO_2CF_3$ |
| B3 | $COCH_3$ | $CO_2H$ |
| B4 | $CH_3$ | $CONH(CH_2)_5CO_2H$ |
| B5 | H | $CONH(CH_2)_5CO_2H$ |
| B6 | $COCH_3$ | 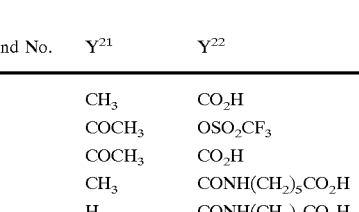 |
| B7 | $COCH_3$ | 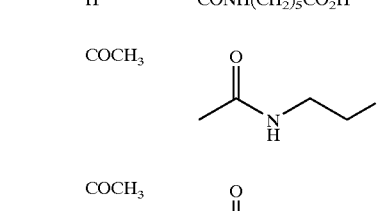 |
| B8 | $CH_3$ | 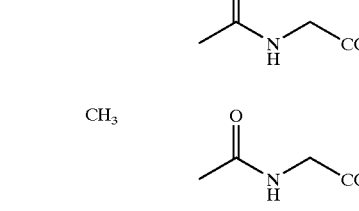 |
| B9 | $CH_3$ | 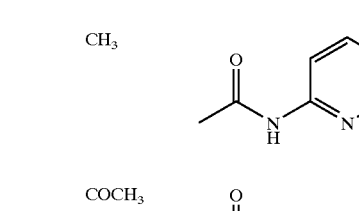 |
| B10 | $COCH_3$ | 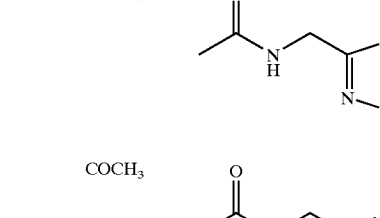 |
| B11 | $COCH_3$ |  |

TABLE 8

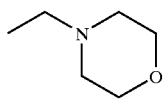

| Compound No. | $Y^{23}$ | $Y^{24}$ |
|---|---|---|
| B12 | $CH_3$ | $OCH_2CH_3$ |
| B13 | $CH_3$ | OH |
| B14 | $CH_3$ | $NH(CH_2)_2CH_3$ |

TABLE 9

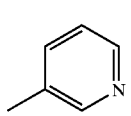

| Compound No. | $Y^{25}$ | $Y^{26}$ |
|---|---|---|
| B15 | $CH_3$ | $OCH_2CH_3$ |
| B16 | H | $OCH_2CH_3$ |
| B17 | H | OH |

TABLE 10

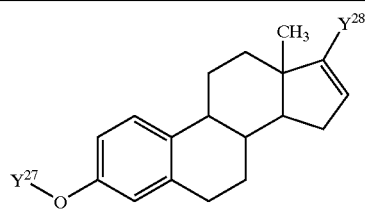

| Compound No. | $Y^{27}$ | $Y^{28}$ |
|---|---|---|
| B18 | $SO_2CH_3$ | CN |
| B19 | $SO_2CH_3$ | CHO |
| B20 | $SO_2CH_3$ | ![morpholinoethyl] |
| B21 | $COCH_3$ | ![pyridyl methyl] |
| B22 | H | $CONH_2$ |

TABLE 10-continued

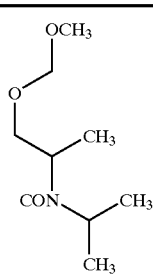

| Compound No. | $Y^{27}$ | $Y^{28}$ |
|---|---|---|
| B23 | $COCH_3$ | ![methoxymethoxy isopropyl amide group] |

BEST MODES FOR CARRYING OUT THE INVENTION

Examples of the invention are described below. In the following examples, the data of $^1$H-NMR were measured at 270 MHz. In the parentheses that follow the δ value of each signal, the measured multiplicity, the coupling constant (unit, Hz) and the number of proton(s) are shown in that order.

EXAMPLE 1

Compound 1

Step 1-1:

3-Methoxyestra-1,3,5(10),16-tetraene-17-carboxylic acid (Compound B1, 400 mg, 1.28 mmol), which was obtained according to the method described in Tetrahedron Letters, Vol. 26, p. 1109 (1985), was suspended in dichloromethane (8 mL), oxalyl chloride (0.437 mL, 5.12 mmol) was added thereto under ice-cooling, and the mixture was stirred at the same temperature for 1 hour. After the reaction mixture was concentrated, the acid chloride of Compound B1 thus obtained was dissolved in dichloromethane (8 mL) followed by addition of pyrrolidine (0.428 mL, 5.15 mmol), and then the mixture was stirred at room temperature for 12 hours. Hydrochloric acid (1 mol/L) was added to the resulting reaction mixture, and then the mixture was extracted with chloroform. The organic layer was washed with a saturated saline solution and dried over anhydrous sodium sulfate, and the solvent was evaporated under reduced pressure. The resulting amide was dissolved in dichloromethane (10 mL) followed by addition of boron tribromide (2.6 mL, 2.6 mmol, a 1.0 mol/L dichloromethane solution) under ice-cooling, and then the mixture was stirred at the same temperature for 2 hours. Then, the reaction mixture was warmed up to room temperature, and further stirred for 1 hour. Methanol (10 mL) was added to the reaction mixture, and then the mixture was stirred at room temperature for 12 hours. Water was added thereto, and then the mixture was extracted with a mixed solvent of chloroform and methanol. The organic layer was washed with a saturated saline solution, and dried over anhydrous sodium sulfate, and the solvent was evaporated under reduced pressure to give a crude product of desulfamoylated Compound 1 (728 mg).

ESI-MS m/z: 352 [M+H]$^+$; $^1$H-NMR (DMSO-d$_6$) δ(ppm): 0.97 (s, 3H), 1.20–1.60 (m, 6H), 1.66–2.36 (m, 9H), 2.68–2.80 (m, 2H), 3.20–3.50 (m, 4H), 6.01–6.07 (m, 1H), 6.43 (d, J=2.6 Hz, 1H), 6.49 (dd, J=2.6, 8.3 Hz, 1H), 7.01 (d, J=8.3 Hz, 1H), 8.98 (s, 1H).

Step 1-2:

The desulfamoylated Compound 1 (582 mg), which was obtained in Step 1-1, was dissolved in dichloromethane (8 mL) followed by addition of 2,6-di-tert-butyl-4-methylpyridine (430 mg, 2.09 mmol) and sulfamoyl chloride (518 mg, 4.48 mmol), and then the mixture was stirred at room temperature for 2 hours. Water was added to the reaction mixture, and then the mixture was extracted with chloroform. The organic layer was washed with a saturated saline solution, and dried over anhydrous sodium sulfate, and the solvent was evaporated under reduced pressure. The resulting residue was purified by silica gel column chromatography (chloroform/methanol=50/1), and then recrystallized from a mixed solvent of ethanol and n-hexane to give Compound 1 (188 mg; yield in three steps 43%).

ESI-MS m/z: 431 [M+H]$^+$; $^1$H-NMR (DMSO-d$_6$) δ(ppm): 0.98 (s, 3H), 1.30–1.65 (m, 6H), 1.65–2.12 (m, 8H), 2.20–2.40 (m, 2H), 2.80–2.90 (m, 3H), 3.20–3.52 (m, 2H), 6.06 (dd, J=1.3, 3.0 Hz, 1H), 6.96 (d, J=2.3 Hz, 1H), 7.00 (dd, J=2.3, 8.6 Hz, 1H), 7.31 (d, J=8.6 Hz, 1H), 7.80 (br s, 2H).

EXAMPLE 2

Compound 2

In a manner similar to that in Step 1-1 in Example 1, the acid chloride of Compound B1 was reacted with piperidine, and then the 3-position of the reaction product was deprotected with boron tribromide (a 1.0 mol/L dichloromethane solution) to give desulfamoylated Compound 2. Next, in a manner similar to that in Step 1-2 in Example 1, the desulfamoylated Compound 2 was sulfamoylated with sulfamoyl chloride in the presence of 2,6-di-tert-butyl-4-methylpyridine to give Compound 2.

ESI-MS m/z: 445 [M+H]$^+$; $^1$H-NMR (DMSO-d$_6$) δ(ppm): 0.98 (s, 3H), 1.36–1.70 (m, 11H), 1.74–2.14 (m, 3H), 2.20–2.38 (m, 3H), 2.80–2.92 (m, 2H), 3.40–3.52 (m, 4H), 5.72–5.78 (m, 1H), 6.96 (d, J=2.3 Hz, 1H), 7.00 (dd, J=2.3, 8.6 Hz, 1H), 7.31 (d, J=8.6 Hz, 1H), 7.84 (br s, 2H).

EXAMPLE 3

Compound 3

In a manner similar to that in Step 1-1 in Example 1, the acid chloride of Compound B1 was reacted with morpholine, and then the 3-position of the reaction product was deprotected with boron tribromide (a 1.0 mol/L dichloromethane solution) to give desulfamoylated Compound 3. Next, in a manner similar to that in Step 1-2 in Example 1, the desulfamoylated Compound 3 was sulfamoylated with sulfamoyl chloride in the presence of 2,6-di-tert-butyl-4-methylpyridine to give Compound 3.

ESI-MS m/z: 447 [M+H]$^+$; $^1$H-NMR (DMSO-d$_6$) δ(ppm): 0.98 (s, 3H), 1.30–1.70 (m, 5H), 1.72–2.16 (m, 3H), 2.20–2.40 (m, 3H), 2.80–2.90 (m, 2H), 3.42–3.60 (m, 8H), 5.78–5.83 (m, 1H), 6.96 (d, J=2.3 Hz, 1H), 7.00 (dd, J=2.3, 8.6 Hz, 1H), 7.31 (d, J=8.6 Hz, 1H), 7.83 (br s, 2H).

EXAMPLE 4

Compound 4

Step 4-1:

Estrone acetate (23.0 g, 73.7 mmol) was dissolved in dichloromethane (70 mL) followed by addition of 2,6-di-tert-butyl-4-methylpyridine (16.6 g, 81.0 mmol) and trifluoromethanesulfonic acid anhydride (12.7 mL, 77.4 mmol), and the mixture was stirred at room temperature for 11 hours. An aqueous saturated sodium hydrogencarbonate solution and water were added to the reaction mixture, and then the mixture was extracted with chloroform. The organic layer was washed with an aqueous saturated sodium hydrogencarbonate solution and a saturated saline solution in that order, and then dried over anhydrous sodium sulfate, and the solvent was evaporated under reduced pressure. The resulting residue was purified by silica gel column chromatography (hexane/ethyl acetate=20/1) to give Compound B2 (28.2 g; yield 86%).

$^1$H-NMR (CDCl$_3$) δ(ppm): 1.00 (s, 3H), 1.36–1.70 (m, 5H), 1.75–1.98 (m, 3H), 2.05–2.20 (m, 1H), 2.28 (s, 3H), 2.26–2.42 (m, 2H), 2.84–2.96 (m, 2H), 5.62 (dd, J=1.3, 3.0 Hz, 1H), 6.80 (d, J=2.3 Hz, 1H), 6.85 (dd, J=2.3, 8.2 Hz, 1H), 7.25 (d, J=8.2 Hz, 1H).

Step 4-2:

Compound B2 (23.0 g, 73.7 mmol) was dissolved in DMF (100 mL) followed by addition of triphenyl phosphine (989 mg, 3.77 mmol), triethylamine (35.0 mL, 252 mmol), formic acid (7.13 mL, 189 mmol) and palladium(II) acetate (423 mg, 1.89 mmol), and then the mixture was stirred in a carbon monoxide atmosphere at room temperature for 1 hour. Hydrochloric acid (1 mol/L) and water were added to the reaction mixture. The resulting precipitate was collected by filtration, and dissolved in chloroform, followed by drying over anhydrous sodium sulfate. The solvent was evaporated under reduced pressure, and the resulting residue was recrystallized from a mixed solvent of chloroform and hexane to give Compound B3 (15.3 g; yield 72%).

ESI-MS m/z: 341 [M+H]$^+$; $^1$H-NMR (CDCl$_3$) δ(ppm): 0.96 (s, 3H), 1.35–1.80 (m, 5H), 1.86–2.22 (m, 2H), 2.24–2.50 (m, 4H), 2.28 (s, 3H), 2.80–2.98 (m, 2H), 6.80 (br s, 1H), 6.84 (br d, J=8.6 Hz, 1H), 6.97 (br s, 1H), 7.28 (d, J=8.6 Hz, 1H).

Step 4-3:

Compound B3 (250 mg, 0.734 mmol) was dissolved in dichloromethane (10 mL) followed by addition of oxalyl chloride (0.263 mL, 3.01 mmol) under ice-cooling, and then the mixture was stirred at the same temperature for 2 hours. After the reaction mixture was concentrated, the acid chloride of Compound B3 thus obtained was dissolved in dichloromethane (5.0 mL) followed by addition of 1-methylpiperazine (0.245 mL, 2.21 mmol) under ice-cooling. The mixture was stirred at room temperature for 3 hours. Hydrochloric acid (1 mol/L) was added to the resulting reaction mixture, and then the mixture was extracted with chloroform. The organic layer was washed with a saturated saline solution and dried over anhydrous sodium sulfate, and the solvent was evaporated under reduced pressure. The resulting amide was dissolved in methanol (3.0 mL) followed by addition of sodium methoxide (0.300 mL, a 28% methanol solution), and then the mixture was stirred at room temperature for 30 minutes. Hydrochloric acid (1 mol/L) was added to the reaction mixture, and then the mixture was extracted with chloroform. The organic layer was washed with a saturated saline solution and dried over anhydrous sodium sulfate, and the solvent was evaporated under reduced pressure. The resulting residue was recrystallized from acetonitrile to give desulfamoylated Compound 4 (159 mg; yield 57%).

ESI-MS m/z: 381 [M+H]+; $^1$H-NMR (DMSO-d$_6$): 0.98 (s, 3H), 1.32–1.68 (m, 5H), 1.82 (m, 2H), 2.02–2.39 (m, 4H), 2.47 (s, 3H), 2.61–2.87 (m, 6H), 3.64 (m, 4H), 5.85 (s, 1H), 6.46 (s, 1H), 6.51 (d, J=8.6 Hz, 1H), 7.02 (d, J=8.6 Hz, 1H), 9.04 (s, 1H).

Step 4-4:

In a manner similar to that in Step 1-2 in Example 1, the desulfamoylated Compound 4 was sulfamoylated with sulfamoyl chloride to give Compound 4.

ESI-MS m/z: 460 [M+H]+; $^1$H-NMR (DMSO-d$_6$) δ(ppm): 0.99 (s, 3H), 1.32–1.68 (m, 5H), 1.80–2.00 (m, 2H), 2.04–2.38 (m, 11H), 2.86 (m, 2H), 3.49 (m, 4H), 5.78 (s, 1H), 6.98 (s, 1H), 7.01 (d, J=8.9 Hz, 1H), 7.32 (d, J=8.6 Hz, 1H), 7.88 (br, 2H).

EXAMPLE 5

Compound 5

Step 5-1:

In a manner similar to that in Step 4-3 in Example 4, the acid chloride of Compound B3 was reacted with 1-(2-pyridyl)piperazine, and then the 3-position of the reaction product was deprotected with sodium methoxide (a 28% methanol solution) to give desulfamoylated Compound 5.

Step 5-2:

The desulfamoylated Compound 5 (163 mg, 0.378 mmol) was dissolved in anhydrous DMF (2.0 mL) followed by addition of sodium hydride (45 mg, 1.1 mmol, 60% dispersion in oil) under ice-cooling, and then the mixture was stirred at the same temperature for 30 minutes. Sulfamoyl chloride (175 mg, 1.51 mmol) was added to the reaction mixture, and the mixture was further stirred at room temperature for 4 hours. Water was added to the reaction mixture, and the mixture was neutralized with an 1 mol/L aqueous sodium hydroxide solution. The resulting precipitate was collected by filtration, washed with water, and dissolved in methanol, and the solvent was evaporated under reduced pressure. The resulting residue was purified by silica gel column chromatography (chloroform/methanol= 15/1) to give Compound 5 (42 mg; yield 22%).

ESI-MS m/z: 523 [M+H]+; $^1$H-NMR (DMSO-d$_6$) δ(ppm): 1.02 (s, 3H), 1.36–1.74 (m, 5H), 1.89 (m, 2H), 2.12 (m, 1H), 2.23–2.42 (m, 3H), 2.88 (m, 2H), 3.47–3.60 (m, 4H), 3.61–3.72 (m, 4H), 5.91 (s, 1H), 6.68 (dd, J=5.0, 6.9 Hz, 1H), 6.84 (d, J=8.9 Hz, 1H), 6.99 (s, 1H), 7.01 (d, J=8.3 Hz, 1H), 7.34 (d, J=8.6 Hz, 1H), 7.57 (m, 1H), 7.93 (br, 2H), 8.13 (m, 1H).

EXAMPLE 6

Compound 6

Step 6-1:

The acid chloride of Compound B3, which was obtained in Step 4-3 in Example 4, was dissolved in dichloromethane (5.0 mL) followed by addition of 1-(2-pyrimidinyl) piperazine dihydrochloride (524 mg, 2.21 mmol) and triethylamine (0.616 mL, 4.42 mmol) under ice-cooling, and then the mixture was stirred at room temperature for 3 hours. Hydrochloric acid (1 mol/L) was added to the reaction mixture, and then the mixture was extracted with chloroform. The organic layer was washed with a saturated saline solution and dried over anhydrous sodium sulfate. The solvent was evaporated under reduced pressure. The resulting amide was dissolved in methanol (5.0 mL) followed by addition of sodium methoxide (a 28% methanol solution) (0.500 mL) at room temperature, and then the mixture was stirred for 30 minutes. The mixture was post-treated in a manner similar to that in Step 4-3 in Example 4, to give desulfamoylated Compound 6 (349 mg, quantitative).

Step 6-2:

In a manner similar to that in Step 1-2 in Example 1, the desulfamoylated Compound 6 was sulfamoylated with sulfamoyl chloride to give Compound 6.

ESI-MS m/z: 524 [M+H]+; $^1$H-NMR (DMSO-d$_6$) δ(ppm): 1.01 (s, 3H), 1.40–1.75 (m, 5H), 1.88 (m, 2H), 2.12 (m, 1H), 2.27–2.40 (m, 3H), 2.86 (m, 2H), 3.64 (m, 4H), 3.73 (m, 4H), 5.89 (s, 1H), 6.67 (t, J=5.0 Hz, 1H), 6.98 (s, 1H), 7.01 (d, J=8.9 Hz, 1H), 7.32 (d, J=8.6 Hz, 1H), 7.88 (br, 2H), 8.38 (d, J=5.0 Hz, 2H).

EXAMPLE 7

Compound 7

In a manner similar to that in Step 1-1 in Example 1, the acid chloride of Compound B1 was reacted with cyclopentylamine, and then the 3-position of the reaction product was deprotected with boron tribromide (a 1.0 mol/L dichloromethane solution) to give desulfamoylated Compound 7. Next, in a manner similar to that in Step 5-2 in Example 5, the desulfamoylated Compound 7 was sulfamoylated with sulfamoyl chloride in the presence of sodium hydride to give Compound 7.

FAB-MS m/z: 445 [M+H]+; $^1$H-NMR (DMSO-d$_6$) δ(ppm): 0.91 (s, 3H), 1.30–1.72 (m, 11H), 1.72–1.94 (m, 3H), 2.04 (m, 1H), 2.15–2.42 (m, 4H), 2.85 (m, 2H), 4.06 (m, 1H), 6.36 (s, 1H), 6.97 (s, 1H), 7.01 (d, J=8.4 Hz, 1H), 7.33 (d, J=8.4 Hz, 1H), 7.60 (d, J=7.6 Hz, 1H), 7.88 (s, 2H).

EXAMPLE 8

Compound 8

In a manner similar to that in Step 1-1 in Example 1, the acid chloride of Compound B1 was reacted with cyclopropylamine, and then the 3-position of the reaction product was deprotected with boron tribromide (a 1.0 mol/L dichloromethane solution) to give desulfamoylated Compound 8. Next, in a manner similar to that in Step 5-2 in Example 5, the desulfamoylated Compound 8 was sulfamoylated with sulfamoyl chloride in the presence of sodium hydride to give Compound 8.

FAB-MS m/z: 417 [M+H]+; $^1$H-NMR (DMSO-d$_6$) δ(ppm): 0.45 (m, 2H), 0.61 (m, 2H), 0.91 (s, 3H), 1.30–1.61 (m, 5H), 1.88 (m, 1H), 2.04 (m, 1H), 2.15–2.42 (m, 4H), 2.67 (m, 1H), 2.85 (m, 2H), 6.34 (s, 1H), 6.97 (d, J=2.5 Hz, 1H), 7.01 (dd, J=2.5, 8.6 Hz, 1H), 7.33 (d, J=8.6 Hz, 1H), 7.78 (d, J=4.3 Hz, 1H), 7.88 (s, 2H).

EXAMPLE 9

Compound 9

In a manner similar to that in Step 1-1 in Example 1, the acid chloride of Compound B1 was reacted with cyclopropanemethylamine, and then the 3-position of the reaction product was deprotected with boron tribromide (a 1.0 mol/L dichloromethane solution) to give desulfamoylated Compound 9. Next, in a manner similar to that in Step 5-2 in Example 5, the desulfamoylated Compound 9 was sulfamoylated with sulfamoyl chloride in the presence of sodium hydride to give Compound 9.

FAB-MS m/z: 431 [M+H]+; $^1$H-NMR (DMSO-d$_6$) δ(ppm): 0.16 (m, 2H), 0.38 (m, 2H), 0.92 (s, 3H), 0.93 (s, 1H), 1.32–1.63 (m, 5H), 1.88 (m, 1H), 2.05 (m, 1H), 2.18–2.40 (m, 4H), 2.86 (m, 2H), 2.99 (t, J=6.2 Hz, 2H), 6.38 (s, 1H), 6.97 (d, J=2.3 Hz, 1H), 7.02 (dd, J=2.3, 8.6 Hz, 1H), 7.33 (d, J=8.6 Hz, 1H), 7.81 (d, J=5.8 Hz, 1H), 7.88 (s, 2H).

EXAMPLE 10

Compound 10

In a manner similar to that in Step 1-1 in Example 1, the acid chloride of Compound B1 was reacted with allylamine, and then the 3-position of the reaction product was deprotected with boron tribromide (a 1.0 mol/L dichloromethane solution) to give desulfamoylated Compound 10. Next, in a manner similar to that in Step 5-2 in Example 5, the desulfamoylated Compound 10 was sulfamoylated with sulfamoyl chloride in the presence of sodium hydride to give Compound 10.

FAB-MS m/z: 417 [M+H]$^+$; $^1$H-NMR (DMSO-d$_6$) δ(ppm): 0.92 (s, 3H), 1.31–1.64 (m, 5H), 1.88 (m, 1H), 2.06 (m, 1H), 2.17–2.43 (m, 4H), 2.86 (m, 2H), 3.73 (m, 2H), 5.00–5.16 (m, 2H), 5.82 (m, 1H), 6.43 (s, 1H), 6.97 (d, J=2.7 Hz, 1H), 7.01 (dd, J=2.7, 8.6 Hz, 1H), 7.33 (d, J=8.6 Hz, 1H), 7.88 (s, 2H), 7.94 (t, J=5.8 Hz, 1H).

EXAMPLE 11

Compound 11

In a manner similar to that in Step 1-1 in Example 1, the acid chloride of Compound B1 was reacted with propargylamine, and then the 3-position of the reaction product was deprotected with boron tribromide (a 1.0 mol/L dichloromethane solution) to give desulfamoylated Compound 11. Next, in a manner similar to that in Step 1-2 in Example 1, the desulfamoylated Compound 11 was sulfamoylated with sulfamoyl chloride in the presence of 2,6-di-tert-butyl-4-methylpyridine to give Compound 11.

FAB-MS m/z: 415 [M+H]$^+$; $^1$H-NMR (DMSO-d$_6$) δ(ppm): 0.91 (s, 3H), 1.32–1.63 (m, 5H), 1.88 (m, 1H), 2.06 (m, 1H), 2.18–2.43 (m, 5H), 2.86 (m, 2H), 3.89 (dd, J=2.5, 5.8 Hz, 2H), 6.45 (s, 1H), 6.97 (d, J=2.6 Hz, 1H), 7.02 (dd, J=2.6, 8.6 Hz, 1H), 7.33 (d, J=8.6 Hz, 1H), 7.88 (s, 2H), 8.21 (t, J=5.6 Hz, 1H).

EXAMPLE 12

Compound 12

In a manner similar to that in Step 6-1 in Example 6, the acid chloride of Compound B3, which was obtained in Step 4-3 in Example 4, was reacted with aminoacetonitrile sulfate in the presence of triethylamine, and then the 3-position of the reaction product was deprotected with sodium methoxide (a 28% methanol solution) to give desulfamoylated Compound 12. Next, in a manner similar to that in Step 5-2 in Example 5, the desulfamoylated Compound 12 was sulfamoylated with sulfamoyl chloride in the presence of sodium hydride to give Compound 12.

ESI-MS m/z: 416 [M+H]$^+$; $^1$H-NMR (CD$_3$OD) δ(ppm): 0.92 (s, 3H), 1.33–1.60 (m, 5H), 1.87 (m, 1H), 2.06 (m, 1H), 2.24–2.34 (m, 4H), 2.81 (m, 2H), 4.06 (s, 2H), 6.40 (dd, J=2.6, 8.3 Hz, 1H), 6.92 (s, 1H), 6.96 (dd, J=2.6, 8.6 Hz, 1H), 7.22 (d, J=8.6 Hz, 1H).

EXAMPLE 13

Compound 13

In a manner similar to that in Step 1-1 in Example 1, the acid chloride of Compound B1 was reacted with N,N-dimethylethylenediamine, and then the 3-position of the reaction product was deprotected with boron tribromide (a 1.0 mol/L dichloromethane solution) to give desulfamoylated Compound 13. Next, in a manner similar to that in Step 5-2 in Example 5, the desulfamoylated Compound 13 was sulfamoylated with sulfamoyl chloride in the presence of sodium hydride to give Compound 13.

FAB-MS m/z: 448 [M+H]$^+$; $^1$H-NMR (CD$_3$OD) δ(ppm): 0.91 (s, 3H), 1.37–1.56 (m, 5H), 1.89 (m, 1H), 2.04 (m, 1H), 2.16 (s, 6H), 2.17–2.38 (m, 6H), 2.85 (m, 2H), 3.19 (q, J=6.6 Hz, 2H), 6.36 (s, 1H), 6.97 (d, J=2.4 Hz, 1H), 7.02 (dd, J=2.3, 8.6 Hz, 1H), 7.33 (d, J=8.6 Hz, 1H), 7.64 (t, J=6.6 Hz, 1H), 7.89 (br, 2H).

EXAMPLE 14

Compound 14

Step 14-1:

In a manner similar to that in Step 1-1 in Example 1, the acid chloride of Compound B1 (206 mg, 0.660 mmol) was reacted with 6-aminocaproic acid (0.077 mL, 0.88 mmol) to give Compound B4 (159 mg; yield 52%). Next, the resulting Compound B4 (159 mg) was dissolved in dichloromethane (5 mL) followed by addition of boron tribromide (2.0 mL, 2.0 mmol, a 1.0 mol/L dichloromethane solution) under ice-cooling, and then the mixture was stirred at the same temperature for 2 hours. The mixture was further stirred at room temperature for 1 hour followed by addition of methanol (10 mL), and then the mixture was stirred at the same temperature for 1 hour. Water was added to the reaction mixture, and then the mixture was extracted with chloroform. The organic layer was washed with a saturated saline solution, and then dried over anhydrous sodium sulfate. The solvent was evaporated under reduced pressure, and the resulting residue was purified by silica gel column chromatography (chloroform/methanol=from 100/1 to 20/1 to 4/1) to give desulfamoylated Compound 14 (159 mg; yield 57%).

Step 14-2:

In a manner similar to that, in Step 1-2 in Example 1, the desulfamoylated Compound 14 was sulfamoylated with sulfamoyl chloride in the presence of 2,6-di-tert-butyl-4-methylpyridine to give Compound 14.

ESI-MS m/z: 505 [M+H]$^+$; $^1$H-NMR (DMSO-d$_6$) δ(ppm): 0.90 (s, 3H), 1.16–1.60 (m, 12H), 1.80–2.10 (m, 2H), 2.28 (t, J=7.6 Hz, 2H), 2.12–2.40 (m, 3H), 2.80–2.90 (m, 2H), 3.06 (dt, J=5.6, 6.3 Hz, 2H), 3.57 (s, 3H), 6.30–6.36 (m, 1H), 6.96 (d, J=2.6 Hz, 1H), 7.00 (dd, J=2.6, 8.6 Hz, 1H), 7.32 (d, J=8.6 Hz, 1H), 7.72 (br t, J=5.6 Hz, 1H), 7.84 (br s, 2H).

EXAMPLE 15

Compound 15

Step 15-1:

Compound B4 (564 mg, 1.33 mmol) was dissolved in dichloromethane (15 mL) followed by addition of boron tribromide (2.9 mL, 2.9 mmol, a 1.0 mol/L dichloromethane solution) under ice-cooling, and then the mixture was stirred at room temperature for 2 hours. Water and an aqueous saturated sodium hydrogencarbonate solution were added -to the reaction mixture in that order, and then the mixture was extracted with a mixed solvent of chloroform and methanol. The organic layer was washed with a saturated saline solution and dried over anhydrous sodium sulfate, and the solvent was evaporated under reduced pressure. The resulting residue was purified by silica gel column chromatography (chloroform/methanol=15/1) to give Compound B5 (325 mg; yield 59%).

Step 15-2:

Compound B5 (160 mg, 0.389 mmol), 1-hydroxybenzotriazole hydrate (HOBt) (56 mg, 0.39 mmol) and dimethylamine hydrochloride (48 mg, 0.58 mmol) were dissolved in DMF (5.0 mL) followed by addition of 1-(3-dimethylaminopropyl)-3-ethylcarbodiimide (0.091 mL, 0.58 mmol) under ice-cooling, and then the mixture was stirred at room temperature for 6 hours. Hydrochloric acid (1 mol/L) was added to the reaction mixture, and then the mixture was extracted with chloroform. The organic layer was washed with a saturated saline solution and dried over anhydrous sodium sulfate, and the solvent was evaporated under reduced pressure. The resulting residue was purified by silica gel column chromatography (chloroform/methanol=20/1) to give desulfamoylated Compound 15 (167 mg; yield 98%)

Step 15-3:

In a manner similar to that in Step 5-2 in Example 5, the desulfamoylated Compound 15 was sulfamoylated with sulfamoyl chloride in the presence of sodium hydride to give Compound 15.

ESI-MS m/z: 518 [M+H]$^+$; $^1$H-NMR (CDCl$_3$) δ(ppm): 0.98 (s, 3H), 1.37–1.42 (m, 3H), 1.52–1.69 (m, 8H), 1.90 (m, 1H), 2.08 (m, 1H), 2.28–2.36 (m, 6H), 2.89–3.00 (m, 8H), 3.32 (m, 2H), 5.60 (br, 1H), 5.81 (br, 1H), 5.98 (br, 1H), 6.33 (s, 1H), 7.05 (s, 1H), 7.10 (d, J=8.6 Hz, 1H), 7.28 (m, 2H).

EXAMPLE 16

Compound 16

In a manner similar to that in Step 15-2 in Example 15, Compound B5 was reacted with methylamine hydrochloride in the presence of HOBt and 1-(3-dimethylaminopropyl)-3-ethylcarbodiimide to give desulfamoylated Compound 16. Next, in a manner similar to that in Step 5-2 in Example 5, the desulfamoylated Compound 16 was sulfamoylated with sulfamoyl chloride in the presence of sodium hydride to give Compound 16.

ESI-MS m/z: 504 [M+H]$^+$; $^1$H-NMR (DMSO-d$_6$) δ(ppm): 0.91 (s, 3H), 1.23 (m, 2H), 1.42–1.51 (m, 9H), 1.91 (m, 1H), 2.01–2.06 (m, 3H), 2.29–2.38 (m, 4H), 2.55 (d, J=4.3 Hz, 3H), 2.86 (m, 2H), 3.07 (m, 2H), 6.34 (s, 1H), 6.97 (s, 1H), 7.01 (d, J=8.6 Hz, 1H), 7.33 (d, J=8.6 Hz, 1H), 7.60–7.81 (br, 2H), 7.88 (s, 2H).

EXAMPLE 17

Compound 17

In a manner similar to that in Step 1-1 in Example 1, the acid chloride of Compound B1 was reacted with N-acetylethylenediamine, and then the 3-position of the reaction product was deprotected with boron tribromide (a 1.0 mol/L dichloromethane solution) to give desulfamoylated Compound 17. Next, in a manner similar to that in Step 5-2 in Example 5, the desulfamoylated Compound 17 was sulfamoylated with sulfamoyl chloride in the presence of sodium hydride to give Compound 17.

FAB-MS m/z: 462 [M+H]$^+$; $^1$H-NMR (DMSO-d$_6$) δ(ppm): 0.92 (s, 3H), 1.41–1.57 (m, 5H), 1.80 (s, 3H), 1.89 (m, 1H), 2.06 (m, 1H), 2.24–2.36 (m, 4H), 2.87 (m, 2H), 3.08–3.17 (m, 4H), 6.38 (s, 1H), 6.97 (d, J=2.6 Hz, 1H), 7.02 (dd, J=2.6, 8.3 Hz, 1H), 7.33 (d, J=8.6 Hz, 1H), 7.79 (br, 1H), 7.88 (br, 2H).

EXAMPLE 18

Compound 18

Step 18-1:

Compound B3 (300 mg, 0.881 mmol) was dissolved in THF (4.5 mL) followed by addition of 1-(3-dimethylaminopropyl)-3-ethylcarbodiimide hydrochloride (EDCI) (338 mg, 1.76 mmol), HOBt (12 mg, 0.088 mmol) and 2-methoxyethylamine (0.153 mL, 1.76 mmol), and then the mixture was stirred for 4.2 hours under ice-cooling. Water was added to the reaction mixture, and then the mixture was extracted with ethyl acetate. The organic layer was washed with a saturated saline solution and then dried over anhydrous sodium sulfate. The solvent was evaporated under reduced pressure, and the resulting residue was purified by preparative thin-layer chromatography (chloroform/methanol=30/1) to give Compound B6 (275 mg; yield 79%).

Step 18-2:

Compound B6 (275 mg, 0.692 mmol) was dissolved in methanol (11 mL) followed by addition of potassium carbonate (287 mg, 2.08 mmol), and then the mixture was stirred at room temperature for 0.8 hours. Water and hydrochloric acid (0.5 mol/L, 6 mL) were added to the reaction mixture in that order, and then the mixture was extracted with ethyl acetate. The organic layer was washed with a saturated saline solution and then dried over anhydrous sodium sulfate. The solvent was evaporated under reduced pressure to give desulfamoylated Compound 18 (266 mg, quantitative).

Step 18-3:

In a manner similar to that in Step 1-2 in Example 1, the desulfamoylated Compound 18 was sulfamoylated with sulfamoyl chloride in the presence of 2,6-di-tert-butyl-4-methylpyridine to give Compound 18.

FAB-MS m/z: 435 [M+H]$^+$; $^1$H-NMR (DMSO-d$_6$) δ(ppm): 0.91 (s, 3H), 1.44–1.56 (m, 5H), 1.95 (m, 1H), 2.07 (m, 1H), 2.30 (m, 4H), 2.86 (m, 2H), 3.24 (s, 3H), 3.36 (m, 4H), 6.39 (br s, 1H), 6.97 (d, J=2.3 Hz, 1H), 7.02 (dd, J=2.6, 8.3 Hz, 1H), 7.33 (d, J=9.1 Hz, 1H), 7.78 (t, J=5.6 Hz, 1H), 7.89 (br s, 2H).

EXAMPLE 19

Compound 19

In a manner similar to that in Step 18-1 in Example 18, Compound B3 was reacted with 2-(tert-butyldimethylsilyloxy)ethylamine, which was obtained in Reference Example 1, in the presence of EDCI and HOBt. Next, in a manner similar to that in Step 18-2 in Example 18, the 3-position of the resulting reaction product was deprotected with potassium carbonate to give desulfamoylated Compound 19. Next, in a manner similar to that in Step 1-2 in Example 1, the desulfamoylated Compound 19 was sulfamoylated with sulfamoyl chloride in the presence of 2,6-di-tert-butyl-4-methylpyridine to give Compound 19.

FAB-MS m/z: 535 [M+H]$^+$; $^1$H-NMR (CDCl$_3$) δ(ppm): 0.08 (s, 6H), 0.91 (s, 9H), 1.01 (s, 3H), 1.46–1.69 (m, 5H), 1.94 (m, 1H), 2.11 (m, 1H), 2.33 (m, 4H), 2.91 (m, 2H), 3.44 (m, 2H), 3.71 (m, 2H), 5.14 (br s, 1H), 6.12 (t, J=5.6 Hz, 1H), 6.37 (m, 1H), 7.05 (d, J=2.6 Hz, 1H), 7.09 (dd, J=2.6, 8.6 Hz, 1H), 7.30 (d, J=8.6 Hz, 1H).

EXAMPLE 20

Compound 20

Compound 19 (251 mg, 0.469 mmol) was dissolved in THF (3.8 mL) followed by addition of acetic acid (1.9 mL) and water (1.9 mL) under ice-cooling, and then the mixture was stirred at the same temperature for 3 hours. Water was added to the reaction mixture, and then the mixture was extracted with ethyl acetate. The organic layer was washed with a saturated saline solution and then dried over anhydrous sodium sulfate. The solvent was evaporated under reduced pressure, and the resulting residue was purified by preparative thin-layer chromatography (chloroform/methanol=12/1) to give Compound 20 (149 mg; yield 75%).

FAB-MS m/z: 421 [M+H]$^+$; $^1$H-NMR (DMSO-d$_6$) δ(ppm): 0.91 (s, 3H), 1.40–1.56 (m, 5H), 1.88 (m, 1H), 2.04 (m, 1H), 2.30 (m, 4H), 2.86 (m, 2H), 3.17 (m, 2H), 3.42 (m, 2H), 4.65 (br, 1H), 6.40 (br s, 1H), 6.97 (d, J=2.3 Hz, 1H), 7.02 (dd, J=2.3, 8.6 Hz, 1H), 7.33 (d, J=8.6 Hz, 1H), 7.69 (t, J=5.6 Hz, 1H), 7.91 (br, 2H).

EXAMPLE 21

Compound 21

In a manner similar to that in Step 18-1 in Example 18, Compound B3 was reacted with 4-(tert-butyldimethylsilyloxy)-1-butylamine, which was obtained in Reference Example 2, in the presence of EDCI and HOBt. Next, in a manner similar to that in Step 18-2 in Example 18, the 3-position of the resulting reaction product was deprotected with potassium carbonate to give desulfamoylated Compound 21. Next, in a manner similar to that in Step 1-2 in Example 1, the desulfamoylated Compound 21 was sulfamoylated with sulfamoyl chloride in the presence of 2,6-di-tert-butyl-4-methylpyridine to give Compound 21.

FAB-MS m/z: 563 [M+H]$^+$; $^1$H-NMR (CDCl$_3$) δ(ppm): 0.05 (s, 6H), 0.89 (s, 9H), 0.98 (s, 3H), 1.42–1.60 (m, 9H), 1.92 (m, 1H), 2.07 (m, 1H), 2.29 (s, 4H), 2.89 (m, 2H), 3.33 (m, 2H), 3.65 (m, 2H), 5.52 (br, 2H), 5.94 (t, J=5.8 Hz, 1H), 6.28 (br s, 1H), 7.04 (d, J=2.3 Hz, 1H), 7.09 (dd, J=2.5, 8.4 Hz, 1H), 7.28 (d, J=8.3 Hz, 1H).

EXAMPLE 22

Compound 22

In a manner similar to that in Example 20, Compound 21 was treated with acetic acid and water to give Compound 22.

FAB-MS m/z: 449 [M+H]$^+$; $^1$H-NMR (DMSO-d$_6$) δ(ppm): 0.91 (s, 3H), 1.44–1.56 (m, 9H), 1.88 (m, 1H), 2.04 (m, 1H), 2.24–2.32 (m, 4H), 2.86 (m, 2H), 3.09 (m, 2H), 3.39 (m, 2H), 4.39 (m, 1H), 6.35 (br s, 1H), 6.97 (br s, 1H), 7.01 (d, J=8.6 Hz, 1H), 7.33 (d, J=8.6 Hz, 1H), 7.74 (t, J=5.6 Hz, 1H), 7.89 (br, 2H).

EXAMPLE 23

Compound 23

In a manner similar to that in Step 4-3 in Example 4, the acid chloride of Compound B3 was amidated with 2-amino-2-methyl-1-propanol, and then the 3-position of the resulting amide was deprotected with potassium carbonate in a manner similar to that in Step 18-2 in Example 18 to give desulfamoylated Compound 23. Next, in a manner similar to that in Step 1-2 in Example 1, the desulfamoylated Compound 23 was sulfamoylated with sulfamoyl chloride in the presence of 2,6-di-tert-butyl-4-methylpyridine to give Compound 23.

FAB-MS m/z: 449 [M+H]$^+$; $^1$H-NMR (DMSO-d$_6$) δ(ppm): 0.92 (s, 3H), 1.23 (s, 6H), 1.29–1.51 (m, 5H), 1.86 (m, 1H), 2.05 (m, 1H), 2.20–2.28 (m, 4H), 2.86 (m, 2H), 3.38 (m, 2H), 4.98 (t, J=5.6 Hz, 1H), 6.32 (br s, 1H), 6.84 (br s, 1H), 6.97 (br s, 1H), 7.01 (br d, J=8.6 Hz, 1H), 7.33 (d, J=8.6 Hz, 1H), 7.89 (s, 2H).

EXAMPLE 24

Compound 24

Step 24-1:

The acid chloride of Compound B3 (1.56 mmol), which was obtained in Step 4-3 in Example 4, was dissolved in THF (40 mL) followed by addition of triethylamine (0.870 mL, 6.25 mmol) and glycine methyl ester hydrochloride (800 mg, 6.37 mmol) dissolved in methanol (10 mL) under ice-cooling, and then the mixture was stirred at room temperature for 5 hours. Next, the mixture was post-treated in a manner similar to that in Step 4-3 in Example 4 to give Compound B7 (690 mg, quantitative).

Step 24-2:

Compound B7 (690 mg, 1.68 mmol) was dissolved in THF (30 mL) followed by addition of methylmagnesium bromide (10 mL, 9.5 mmol, a 0.95 mol/L THF solution) under ice-cooling, and then the mixture was stirred at room temperature for 4 hours. Ethyl acetate and water were added to the reaction mixture, and the organic layer was washed with hydrochloric acid (1 mol/L) and then with a saturated saline solution. The solvent was evaporated under reduced pressure, and the resulting residue was dissolved in methanol (20 mL). Potassium carbonate (1.0 g, 7.2 mmol) was added to the mixture, and the mixture was stirred at room temperature for 4.5 hours. The mixture was post-treated in a manner similar to that in Step 18-2 in Example 18 to give desulfamoylated Compound 24 (305 mg; yield 49%).

Step 24-3:

In a manner similar to that in Step 1-2 in Example 1, the desulfamoylated Compound 24 was sulfamoylated with sulfamoyl chloride in the presence of 2,6-di-tert-butyl-4-methylpyridine to give Compound 24.

FAB-MS m/z: 449 [M+H]$^+$; $^1$H-NMR (DMSO-d$_6$) δ(ppm): 0.93 (s, 3H), 1.06 (s, 6H), 1.41–1.54 (m, 5H), 1.95 (m, 1H), 2.07 (m, 1H), 2.29 (m, 4H), 2.85 (m, 2H), 3.09 (d, J=5.9 Hz, 2H), 4.52 (s, 1H), 6.42 (s, 1H), 6.97 (br s, 1H), 7.01 (br d, J=8.6 Hz, 1H), 7.33 (d, J=8.6 Hz, 1H), 7.46 (t, J=5.9 Hz, 1H), 7.88 (s, 2H).

EXAMPLE 25

Compound 25

Step 25-1:

The acid chloride of Compound B1, which was obtained in Step 1-1 in Example 1, was dissolved in THF (5 mL) followed by addition of glycine (157 mg, 2.09 mmol) dissolved in water (2 mL) under ice-cooling, and then the mixture was stirred at the same temperature for 45 minutes and then at room temperature for 30 minutes. The reaction mixture was post-treated in a manner similar to that in Step 4-3 in Example 4 to give Compound B8 (234 mg; yield 89%).

Step 25-2:

Compound B8 (207 mg, 0.560 mmol) was dissolved in dichloromethane (5 mL) followed by addition of boron tribromide (1.7 mL, 1.7 mmol, a 1.0 mol/L dichloromethane solution) under ice-cooling, and then the mixture was stirred at the same temperature for 2 hours. Water was added to the reaction mixture, and then the mixture was extracted with a mixed solvent of chloroform and methanol. The organic layer was washed with water and then with a saturated saline solution, and thereafter dried over anhydrous sodium sulfate. The solvent was evaporated under reduced pressure, and desulfamoylated Compound 25 (142 mg; yield 72%) was thus obtained.

Step 25-3:

In a manner similar to that in Step 1-2 in Example 1, the desulfamoylated Compound 25 was sulfamoylated with sulfamoyl chloride in the presence of 2,6-di-tert-butyl-4-methylpyridine to give Compound 25.

FAB-MS m/z: 435 [M+H]+; $^1$H-NMR (CDCl$_3$-CD$_3$OD) δ(ppm): 1.01 (s, 3H), 1.19–1.66 (m, 5H), 1.92–2.33 (m, 6H), 2.91 (m, 2H), 4.02 (br s, 2H), 6.50 (br s, 1H), 7.04 (br s, 1H), 7.06 (d, J=8.2 Hz, 1H), 7.28 (d, J=8.2 Hz, 1H).

EXAMPLE 26

Compound 26

Step 26-1:

The desulfamoylated Compound 25 (230 mg, 0.648 mmol) was dissolved in dichloromethane (20 mL) followed by addition of oxalyl chloride (0.300 mL, 3.44 mmol), and then the mixture was stirred at room temperature for 45 minutes. After the reaction mixture was concentrated, the resulting acid chloride was dissolved in dichloromethane (20 mL). The mixture was added to a mixture of methanol (20 mL), triethylamine (1.0 mL, 7.2 mmol) and a dichloromethane solution (30 mL) of 4-(dimethylamino)pyridine (250 mg, 2.05 mmol) under ice-cooling. The mixture was stirred at the same temperature for 15 minutes and then at room temperature for 2 hours. Ethyl acetate was added to the reaction mixture, and the organic layer was washed with hydrochloric acid (1 mol/L) and then with a saturated saline solution, and thereafter dried over anhydrous magnesium sulfate. The solvent was evaporated under reduced pressure, and desulfamoylated Compound 26 (240 mg, quantitative) was thus obtained.

Step 26-2:

In a manner similar to that in Step 5-2 in Example 5, the desulfamoylated Compound 26 was sulfamoylated with sulfamoyl chloride in the presence of sodium hydride to give Compound 26.

FAB-MS m/z: 449 [M+H]+; $^1$H-NMR (DMSO-d$_6$) δ(ppm): 0.91 (s, 3H), 1.42–1.56 (m, 5H), 1.89 (m, 1H), 2.10 (m, 1H), 2.27–2.33 (m, 4H), 2.86 (m, 2H), 3.64 (s, 3H), 3.85 (d, J=5.6 Hz, 2H), 6.48 (br s, 1H), 6.97 (br s, 1H), 7.01 (br d, J=8.6 Hz, 1H), 7.32 (d, J=8.6 Hz, 1H), 7.88 (s, 2H), 8.19 (t, J=5.9 Hz, 1H).

EXAMPLE 27

Compound 27

In a manner similar to that in Step 25-1 in Example 25, the acid chloride of Compound B1 was reacted with L-alanine, and then the 3-position of the reaction product was deprotected with boron tribromide (a 1.0 mol/L dichloromethane solution) in a manner similar to that in Step 25-2 in Example 25 to give desulfamoylated Compound 27. Next, in a manner similar to that in Step 1-2 in Example 1, the desulfamoylated Compound 27 was sulfamoylated with sulfamoyl chloride in the presence of 2,6-di-tert-butyl-4-methylpyridine to give Compound 27.

FAB-MS m/z: 449 [M+H]+; $^1$H-NMR (CDCl$_3$-CD$_3$OD) δ(ppm): 1.00 (s, 3H), 1.41 (d, J=6.6 Hz, 3H), 1.44–2.67 (m, 11H), 2.90 (m, 6H), 4.50 (m, 1H), 6.49 (m, 1H), 7.04 (br s, 1H), 7.07 (d, J=8.2 Hz, 1H), 7.28 (d, J=8.2Hz, 1H).

EXAMPLE 28

Compound 28

In a manner similar to that in Step 25-1 in Example 25, the acid chloride of Compound B1 was reacted with L-valine, and then the 3-position of the reaction product was deprotected with boron tribromide (a 1.0 mol/L dichloromethane solution) in a manner similar to that in Step 25-2 in Example 25 to give desulfamoylated Compound 28. Next, in a manner similar to that in Step 5-2 in Example 5, the desulfamoylated Compound 28 was sulfamoylated with sulfamoyl chloride in the presence of sodium hydride to give Compound 28.

FAB-MS m/z: 477 [M+H]+; $^1$H-NMR (CD$_3$OD) δ(ppm): 0.99 (d, J=6.9 Hz, 3H), 1.00 (d, J=6.9 Hz, 3H), 1.03 (s, 3H), 1.44–1.78 (m, 6H), 2.10–2.43 (m, 6H), 2.92 (m, 2H), 4.38 (d, J=5.6 Hz, 1H), 6.51 (br s, 1H), 7.02 (br s, 1H), 7.05 (dd, J=2.6, 8.3 Hz, 1H), 7.32 (d, J=8.3 Hz, 1H).

EXAMPLE 29

Compound 29

In a manner similar to that in Step 24-1 in Example 24, the acid chloride of Compound B1 was reacted with L-valine methyl ester hydrochloride in the presence of triethylamine, and then the 3-position of the reaction product was deprotected with boron tribromide (a 1.0 mol/L dichloromethane solution) in a manner similar to that in Step 25-2 in Example 25 to give desulfamoylated Compound 29. Next, in a manner similar to that in Step 1-2 in Example 1, the desulfamoylated Compound 29 was sulfamoylated with sulfamoyl chloride in the presence of 2,6-di-tert-butyl-4-methylpyridine to give Compound 29.

FAB-MS m/z: 491 [M+H]+; $^1$H-NMR (CDCl$_3$) δ(ppm): 0.93 (d, J=6.9 Hz, 3H), 0.97 (d, J=6.9 Hz, 3H), 1.03 (s, 3H), 1.43–1.68 (m, 7H), 1.94 (m, 1H), 2.07–2.32 (m, 4H), 2.91 (m, 2H), 3.76 (s, 3H), 4.65 (dd, J=4.6, 8.9 Hz, 1H), 5.01 (s, 2H), 6.19 (d, J=8.9 Hz, 1H), 6.46 (br s, 1H), 7.05 (br s, 1H), 7.08 (br d, J=8.6 Hz, 1H), 7.30 (d, J=8.6 Hz, 1H).

EXAMPLE 30

Compound 30

In a manner similar to that in Step 25-1 in Example 25, the acid chloride of Compound B3, which was obtained in Step 4-3 in Example 4, was reacted with 2-aminoisobutyric acid, and then the 3-position of the reaction product was deprotected with potassium carbonate in a manner similar to that in Step 18-2 in Example 18 to give desulfamoylated Compound 30. Next, in a manner similar to that in Step 1-2 in Example 1, the desulfamoylated Compound 30 was sulfamoylated with sulfamoyl chloride in the presence of 2,6-di-tert-butyl-4-methylpyridine to give Compound 30.

FAB-MS m/z: 463 [M+H]+; $^1$H-NMR (CD$_3$OD) δ(ppm): 1.00 (s, 3H), 1.52 (s, 6H), 1.42–1.70 (m, 5H), 1.90–2.37 (m, 6H), 2.91 (m, 2H), 6.41 (br s 1H), 7.01 (br s, 1H), 7.04 (br d, J=8.2 Hz, 1H), 7.31 (d, J=8.2 Hz, 1H).

EXAMPLE 31

Compound 31

In a manner similar to that in Step 25-1 in Example 25, the acid chloride of Compound B1 was reacted with L-α-phenylglycine, and then the 3-position of the reaction product was deprotected with boron tribromide (a 1.0 mol/L dichloromethane solution) in a manner similar to that in Step 25-2 in Example 25 to give desulfamoylated Compound 31. Next, in a manner similar to that in Step 5-2 in Example 5, the desulfamoylated Compound 31 was sulfamoylated with sulfamoyl chloride in the presence of sodium hydride to give Compound 31.

FAB-MS m/z: 511 [M+H]+; $^1$H-NMR (CD$_3$OD) δ(ppm): 1.04 (s, 3H), 1.47–1.72 (m, 5H), 1.95–2.40 (m, 6H), 2.92 (m, 2H), 5.50 (m, 1H), 6.56 (s, 1H), 7.02 (br s, 1H), 7.04 (d, J=8.5 Hz, 1H), 7.45 (m, 6H).

EXAMPLE 32

Compound 32

In a manner similar to that in Step 25-1 in Example 25, the acid chloride of Compound B3, which was obtained in Step 4-3 in Example 4, was reacted with L-proline, and then the 3-position of the reaction product was deprotected with potassium carbonate in a manner similar to that in Step 18-2 in Example 18 to give desulfamoylated Compound 32. Next, in a manner similar to that in Step 1-2 in Example 1, the desulfamoylated Compound 32 was sulfamoylated with sulfamoyl chloride in the presence of 2,6-di-tert-butyl-4-methylpyridine to give Compound 32.

FAB-MS m/z: 475 [M+H]$^+$; $^1$H-NMR (CD$_3$OD) δ(ppm): 1.24 (s, 3H), 1.49–1.68 (m, 9H), 2.01–2.37 (m, 6H), 2.92 (m, 2H), 3.68–3.82 (m, 2H), 4.43 (d, J=8.6 Hz, 1H), 6.20 (br s, 1H), 7.02 (br s, 1H), 7.64 (dd, J=2.6, 8.6 Hz, 1H), 7.31 (d, J=8.6 Hz, 1H).

EXAMPLE 33

Compound 33

In a manner similar to that in Step 24-1 in Example 24, the acid chloride of Compound B3, which was obtained in Step 4-3 in Example 4, was reacted with L-proline methyl ester hydrochloride in the presence of triethylamine, and then the 3-position of the reaction product was deprotected with potassium carbonate in a manner similar to that in Step 18-2 in Example 18 to give desulfamoylated Compound 33. Next, in a manner similar to that in Step 1-2 in Example 1, the desulfamoylated Compound 33 was sulfamoylated with sulfamoyl chloride in the presence of 2,6-di-tert-butyl-4-methylpyridine to give Compound 33.

FAB-MS m/z: 489 [M+H]$^+$; $^1$H-NMR (CDCl$_3$) δ(ppm): 1.07 (s, 3H), 1.46–1.51 (m, 6H), 1.94–2.41 (m, 9H), 2.92 (m, 2H), 3.65–3.74 (m, 2H), 3.75 (s, 3H), 4.54 (m, 1H), 5.09 (s, 2H), 6.15 (br s, 1H), 7.05 (br s, 1H), 7.08 (br d, J=8.6 Hz, 1H), 7.29 (d, J=8.6 Hz, 1H).

EXAMPLE 34

Compound 34

In a manner similar to that in Step 1-1 in Example 1, the acid chloride of Compound B1 was reacted with aniline, and then the 3-position of the reaction product was deprotected with boron tribromide (a 1.0 mol/L dichloromethane solution) to give desulfamoylated Compound 34. Next, in a manner similar to that in Step 1-2 in Example 1, the desulfamoylated Compound 34 was sulfamoylated with sulfamoyl chloride in the presence of 2,6-di-tert-butyl-4-methylpyridine to give Compound 34.

ESI-MS m/z: 453 [M+H]$^+$; $^1$H-NMR (DMSO-d$_6$) δ(ppm): 0.99 (s, 3H), 1.40–1.64 (m, 5H), 1.80–2.46 (m, 6H), 2.82–2.92 (m, 2H), 6.60–6.68 (m, 1H), 6.92–7.06 (m, 3H), 7.22–7.38 (m, 3H), 7.62–7.70 (m, 2H), 7.87 (br s, 2H), 9.69 (s, 1H).

EXAMPLE 35

Compound 35

In a manner similar to that in Step 4-3 in Example 4, the acid chloride of Compound B3 was reacted with 3-aminobenzoic acid, and then the 3-position of the reaction product was deprotected with sodium methoxide (a 28% methanol solution) to give desulfamoylated Compound 35. Next, in a manner similar to that in Step 1-2 in Example 1, the desulfamoylated Compound 35 was sulfamoylated with sulfamoyl chloride in the presence of 2,6-di-tert-butyl-4-methylpyridine to give Compound 35.

ESI-MS m/z: 497 [M+H]$^+$; $^1$H-NMR (DMSO-d$_6$) δ(ppm): 1.01 (s, 3H), 1.42–1.67 (m, 5H), 1.92 (m, 1H), 2.16 (m, 1H), 2.28–2.44 (m, 4H), 2.89 (m, 2H), 6.72 (s, 1H), 6.99 (s, 1H), 7.03 (m, 1H), 7.32–7.41 (m, 2H), 7.62 (d, J=7.6Hz, 1H), 7.82–7.94 (m, 3H), 8.27 (br, 1H), 8.34 (s, 1H), 9.84 (s, 1H).

EXAMPLE 36

Compound 36

In a manner similar to that in Step 1-1 in Example 1, the acid chloride of Compound B1 was reacted with benzylamine, and then the 3-position of the reaction product was deprotected with boron tribromide (a 1.0 mol/L dichloromethane solution) to give desulfamoylated Compound 36. Next, in a manner similar to that in Step 1-2 in Example 1, the desulfamoylated Compound 36 was sulfamoylated with sulfamoyl chloride in the presence of 2,6-di-tert-butyl-4-methylpyridine to give Compound 36.

FAB-MS m/z: 467 [M+H]$^+$; $^1$H-NMR (DMSO-d$_6$) δ(ppm): 0.94 (s, 3H), 1.32–1.67 (m, 5H), 1.88 (m, 1H), 2.08 (m, 1H), 2.20–2.42 (m, 4H), 2.86 (m, 2H), 4.32 (m, 2H), 6.46 (s, 1H), 6.97 (d, J=2.3 Hz, 1H), 7.02 (dd, J=2.3, 8.6 Hz, 1H), 7.19–7.42. (m, 6H), 7.88 (s, 2H), 8.34 (t, J=6.1 Hz, 1H).

EXAMPLE 37

Compound 37

In a manner similar to that in Step 4-3 in Example 4, the acid chloride of Compound B3 was reacted with 4-(aminomethyl)benzoic acid, and then the 3-position of the reaction product was deprotected with sodium methoxide (a 28% methanol solution) to give desulfamoylated Compound 37. Next, in a manner similar to that in Step 1-2 in Example 1, the desulfamoylated Compound 37 was sulfamoylated with sulfamoyl chloride in the presence of 2,6-di-tert-butyl-4-methylpyridine to give Compound 37.

ESI-MS m/z: 511 [M+H]$^+$; $^1$H-NMR (DMSO-d$_6$) δ(ppm): 0.94 (s, 3H), 1.43–1.62 (m, 5H), 1.91 (m, 1H), 2.08 (m, 1H), 2.29–2.40 (m, 4H), 2.87 (m, 2H), 4.39 (d, J=6.3 Hz, 2H), 6.49 (s, 1H), 6.97 (d, J=2.6 Hz, 1H), 7.02 (dd, J=2.6, 8.3 Hz, 1H), 7.31–7.37 (m, 3H), 7.82–7.91 (m, 4H), 8.40 (br, 1H).

EXAMPLE 38

Compound 38

Step 38-1:

A dichloromethane solution (5.0 mL) of the acid chloride of Compound B1, which was obtained in Step 1-1 in Example 1, was added to a pyridine solution (5 mL) of 2-aminopyridine (266 mg, 2.83 mmol) under ice-cooling, and then the mixture was stirred at room temperature for 16 hours. Hydrochloric acid (1 mol/L) was added to the reaction mixture, and then the mixture was extracted with chloroform. The organic layer was washed with hydrochloric acid (1 mol/L), an aqueous saturated sodium hydrogencarbonate solution and a saturated saline solution in that order, and then dried over anhydrous sodium sulfate. The solvent was evaporated under reduced pressure, and the resulting residue was purified by silica gel column chromatography (chloroform) to give Compound B9 (305 mg; yield 87%).

Step 38-2:

In a manner similar to that in Step 1-1 in Example 1, Compound B9 was treated with boron tribromide (a 1.0 mol/L dichloromethane solution) to give desulfamoylated Compound 38. Next, in a manner similar to that in Step 5-2 in Example 5, the desulfamoylated Compound 38 was sulfamoylated with sulfamoyl chloride in the presence of sodium hydride to give Compound 38.

FAB-MS m/z: 454 [M+H]$^+$; $^1$H-NMR (DMSO-d$_6$) δ(ppm): 0.98 (s, 3H), 1.36–1.70 (m, 5H), 1.91 (m, 1H), 2.13 (m, 1H), 2.22–2.43 (m, 4H), 2.87 (m, 2H), 6.89 (s, 1H), 6.98 (s, 1H), 7.02 (d, J=8.6 Hz, 1H), 7.10 (dd, J=5.0, 7.3 Hz, 1H), 7.34 (d, J=8.6 Hz, 1H), 7.77 (t, J=8.6 Hz, 1H), 7.89 (s, 2H), 8.09 (dd, J=1.0, 8.6 Hz, 1H), 8.33 (m, 1H), 10.10 (s, 1H).

EXAMPLE 39

Compound 39

In a manner similar to that in Step 38-1 in Example 38, the acid chloride of Compound B3, which was obtained in Step 4-3 in Example 4, was reacted with 5-amino-2-methoxypyridine, and then the 3-position of the reaction product was deprotected with sodium methoxide (a 28% methanol solution) in a manner similar to that in Step 4-3 in Example 4 to give desulfamoylated Compound 39. Next, in a manner similar to that in Step 5-2 in Example 5, the desulfamoylated Compound 39 was sulfamoylated with sulfamoyl chloride in the presence of sodium hydride to give Compound 39.

ESI-MS m/z: 484 [M+H]$^+$; $^1$H-NMR (DMSO-d$_6$) δ(ppm): 1.00 (s, 3H), 1.41–1.62 (m, 5H), 1.91 (m, 1H), 2.17 (m, 1H), 2.24–2.42 (m, 4H), 2.89 (m, 2H), 3.83 (s, 3H), 6.67 (s, 1H), 6.80 (d, J 8.9 Hz, 1H), 7.00 (s, 1H), 7.03 (d, J=8.3 Hz, 1H), 7.35 (d, J=7.9 Hz, 1H), 7.88 (br, 2H), 7.96 (dd, J=2.6, 8.9 Hz, 1H), 8.43 (d, J=2.6 Hz, 1H), 9.76 (s, 1H).

EXAMPLE 40

Compound 40

In a manner similar to that in Step 38-1 in Example 38, the acid chloride of Compound B1 was reacted with 2-aminopyrazine, and then the 3-position of the reaction product was deprotected with boron tribromide (a 1.0 mol/L dichloromethane solution) in a manner similar to that in Step 1-1 in Example 1 to give desulfamoylated Compound 40. Next, in a manner similar to that in Step 5-2 in Example 5, the desulfamoylated Compound 40 was sulfamoylated with sulfamoyl chloride in the presence of sodium hydride to give Compound 40.

FAB-MS m/z: 455 [M+H]$^+$; $^1$H-NMR (DMSO-d$_6$) δ(ppm): 0.99 (s, 3H), 1.37–1.70 (m, 5H), 1.92 (m, 1H), 2.08–2.43 (m, 5H), 2.88 (m, 2H), 7.00 (m, 2H), 7.02 (d, J=8.6 Hz, 1H), 7.35 (d, J=8.6 Hz, 1H), 7.88 (s, 2H), 8.35 (d, J=2.3 Hz, 1H), 8.42 (t, J=1.7 Hz, 1H), 9.32 (s, 1H), 10.52 (s, 1H).

EXAMPLE 41

Compound 41

In a manner similar to that in Step 38-1 in Example 38, the acid chloride of Compound B3, which was obtained in Step 4-3 in Example 4, was reacted with 2-aminopyrimidine, and then the 3-position of the reaction product was deprotected with potassium carbonate in a mariner similar to that in Step 18-2 in Example 18 to give desulfamoylated Compound 41. Next, in a manner similar to that in Step 5-2 in Example 5, the desulfamoylated Compound 41 was sulfamoylated with sulfamoyl chloride in the presence of sodium hydride to give Compound 41.

FAB-MS m/z: 455 [M+H]$^+$; $^1$H-NMR (DMSO-d$_6$) δ(ppm): 0.96 (s, 3H), 1.34–1.70 (m, 5H), 1.91 (m, 1H), 2.13 (m, 1H), 2.25–2.48 (m, 4H), 2.88 (m, 2H), 6.85 (s, 1H), 6.98 (s, 1H), 7.02 (d, J=8.6 Hz, 1H), 7.19 (t, J=4.9 Hz, 1H), 7.34 (d, J=8.6 Hz, 1H), 7.89 (s, 2H), 8.66 (d, J=4.9 Hz, 2H), 10.34 (s, 1H).

EXAMPLE 42

Compound 42

In a manner similar to that in Step 1-1 in Example 1, the acid chloride of Compound B1 was reacted with 2-(aminomethyl)pyridine, and then the 3-position of the reaction product was deprotected with boron tribromide (a 1.0 mol/L dichloromethane solution) to give desulfamoylated Compound 42. Next, in a manner similar to that in Step 5-2 in Example 5, the desulfamoylated Compound 42 was sulfamoylated with sulfamoyl chloride in the presence of sodium hydride to give Compound 42.

ESI-MS m/z: 468 [M+H]$^+$; $^1$H-NMR (DMSO-d$_6$) δ(ppm): 0.95 (s, 3H), 1.38–1.61 (m, 5H), 1.90 (m, 1H), 2.10 (m, 1H), 2.21–2.40 (m, 4H), 3.33 (m, 2H), 4.42 (d, J=5.6 Hz, 2H), 6.52 (s, 1H), 6.98 (s, 1H), 7.02 (d, J=8.9 Hz, 1H), 7.24 (d, J=7.9 Hz, 2H), 7.33 (d, J=8.6 Hz, 1H), 7.76 (t, J=7.9 Hz, 1H), 7.88 (br, 2H), 8.39 (br, 1H), 8.49 (d, J=3.3 Hz, 1H).

EXAMPLE 43

Compound 43

In a manner similar to that in Step 1-1 in Example 1, the acid chloride of Compound B1 was reacted with 3-(aminomethyl)pyridine, and then the 3-position of the reaction product was deprotected with boron tribromide (a 1.0 mol/L dichloromethane solution) to give desulfamoylated Compound 43. Next, in a manner similar to that in Step 5-2 in Example 5, the desulfamoylated Compound 43 was sulfamoylated with sulfamoyl chloride in the presence of sodium hydride to give Compound 43.

ESI-MS m/z: 468 [M+H]$^+$; $^1$H-NMR (DMSO-d$_6$) δ(ppm): 0.93 (s, 3H), 1.38–1.62 (m, 5H), 1.90 (m, 1H), 2.12 (m, 1H), 2.22–2.40 (m, 4H), 2.86 (m, 2H), 4.34 (d, J=5.9 Hz, 2H), 6.46 (s, 1H), 6.97 (s, 1H), 7.02 (d, J=8.9 Hz, 1H), 7.32 (d, J=8.6 Hz, 2H), 7.65 (d, J=7.9 Hz, 1H), 7.86 (br, 2H), 8.39–8.48 (m, 3H), 8.99 (br, 1H).

EXAMPLE 44

Compound 44

In a manner similar to that in Step 4-3 in Example 4, the acid chloride of Compound B3 was reacted with 4-(aminomethyl)pyridine, and then the 3-position of the reaction product was deprotected with sodium methoxide (a 28% methanol solution) to give desulfamoylated Compound 44. Next, in a manner similar to that in Step 5-2 in Example 5, the desulfamoylated Compound 44 was sulfamoylated with sulfamoyl chloride in the presence of sodium hydride to give Compound 44.

ESI-MS m/z: 468 [M+H]$^+$; $^1$H-NMR (DMSO-d$_6$) δ(ppm): 0.94 (s, 3H), 1.37–1.60 (m, 5H), 1.90 (m, 1H), 2.11 (m, 1H), 2.20–2.37 (m, 4H), 2.86 (m, 2H), 4.35 (m, 2H), 6.51 (s, 1H), 6.98 (s, 1H), 7.02 (d, J=8.3 Hz, 1H), 7.24 (d, J=5.9 Hz, 2H), 7.33 (d, J=8.9 Hz, 1H), 7.90 (br, 2H), 8.45 (br, 1H), 8.50 (d, J=5.9 Hz, 2H).

EXAMPLE 45

Compound 45

In a manner similar to that in Step 4-3 in Example 4, the acid chloride of Compound B3 was reacted with 2-(aminomethyl)-5-methylpyridine, and then the 3-position of the reaction product was deprotected with sodium methoxide (a 28% methanol solution) to give desulfamoylated Compound 45. Next, in a manner similar to that in Step 5-2 in Example 5, the desulfamoylated Compound 45 was sulfamoylated with sulfamoyl chloride in the presence of sodium hydride to give Compound 45.

ESI-MS m/z: 482 [M+H]$^+$; $^1$H-NMR (DMSO-d$_6$) δ(ppm): 0.94 (s, 3H), 1.37–1.62 (m, 5H), 1.90 (m, 1H), 2.07 (m, 1H), 2.21–2.39 (m, 7H), 2.86 (m, 2H), 4.45 (d, J=5.3 Hz, 2H), 6.49 (s, 1H), 6.98 (s, 1H), 7.02 (d, J=8.6 Hz, 1H), 7.22 (dd, J=4.9, 7.6 Hz, 1H), 7.34 (d, J=8.6 Hz, 1H), 7.58 (d, J=7.6 Hz, 1H), 7.89 (br, 1H), 8.06 (br, 1H), 8.36 (d, J=3.3 Hz, 1H).

EXAMPLE 46

Compound 46

In a manner similar to that in Step 4-3 in Example 4, the acid chloride of Compound B3 was reacted with 2-(aminomethyl)-4-methylpyridine, and then the 3-position of the reaction product was deprotected with sodium methoxide (a 28% methanol solution) to give desulfamoylated Compound 46. Next, in a manner similar to that in Step 5-2 in Example 5, the desulfamoylated Compound 46 was sulfamoylated with sulfamoyl chloride in the presence of sodium hydride to give Compound 46.

ESI-MS m/z: 482 [M+H]$^+$; $^1$H-NMR (DMSO-d$_6$) δ(ppm): 0.94 (s, 3H), 1.27–1.62 (m, 5H), 1.90 (m, 1H), 2.09 (m, 1H), 2.25–2.41 (m, 7H), 2.86 (m, 2H), 4.38 (d, J=5.9 Hz, 2H), 6.51 (s, 1H), 6.97–7.09 (m, 4H), 7.34 (d, J=8.6 Hz, 1H), 7.88 (br, 2H), 8.32–8.36 (m, 2H).

EXAMPLE 47

Compound 47

In a manner similar to that in Step 4-3 in Example 4, the acid chloride of Compound B3 was reacted with 2-(aminomethyl)-4-methoxypyridine, and then the 3-position of the reaction product was deprotected with sodium methoxide (a 28% methanol solution) to give desulfamoylated Compound 47. Next, in a manner similar to that in Step 5-2 in Example 5, the desulfamoylated Compound 47 was sulfamoylated with sulfamoyl chloride in the presence of sodium hydride to give Compound 47.

ESI-MS m/z: 498 [M+H]$^+$; $^1$H-NMR (DMSO-d$_6$) δ(ppm): 0.94 (s, 3H), 1.42–1.68 (m, 5H), 2.01 (m, 1H), 2.05 (m, 1H), 2.27–2.42 (m, 4H), 2.86 (m, 2H), 3.80 (s, 3H), 4.36 (d, J=5.9 Hz, 2H), 6.51 (s, 1H), 6.78 (d, J=2.3 Hz, 1H), 6.85 (m, 1H), 6.98 (d, J=2.3 Hz, 1H), 7.02 (d, J=8.6 Hz, 1H), 7.33 (d, J=8.6 Hz, 1H), 7.88 (br, 2H), 8.33 (m, 1H).

EXAMPLE 48

Compound 48

In a manner similar to that in Step 4-3 in Example 4, the acid chloride of Compound B3 was reacted with 2-(aminomethyl)pyrazine, and then the 3-position of the reaction product was deprotected with sodium methoxide (a 28% methanol solution) to give desulfamoylated Compound 48. Next, in a manner similar to that in Step 5-2 in Example 5, the desulfamoylated Compound 48 was sulfamoylated with sulfamoyl chloride in the presence of sodium hydride to give Compound 48.

ESI-MS m/z: 469 [M+H]$^+$; $^1$H-NMR (DMSO-d$_6$) δ(ppm): 0.93 (s, 3H), 1.32–1.67 (m, 5H), 1.90 (m, 1H), 2.08 (m, 1H), 2.22–2.42 (m, 4H), 2.87 (m, 2H), 4.46 (d, J=5.3 Hz, 2H), 6.52 (s, 1H), 6.98 (s, 1H), 7.02 (d, J=8.6 Hz, 1H), 7.34 (d, J=8.6 Hz, 1H), 7.83 (br, 2H), 8.44–8.60 (m, 4H).

EXAMPLE 49

Compound 49

In a manner similar to that in Step 1-1 in Example 1, the acid chloride of Compound B1 was reacted with 2-(aminomethyl)-5-methylpyrazine, and then the 3-position of the reaction product was deprotected with boron tribromide (a 1.0 mol/L dichloromethane solution) to give desulfamoylated Compound 49. Next, in a manner similar to that in Step 5-2 in Example 5, the desulfamoylated Compound 49 was sulfamoylated with sulfamoyl chloride in the presence of sodium hydride to give Compound 49.

ESI-MS m/z: 483 [M+H]$^+$; $^1$H-NMR (DMSO-d$_6$) δ(ppm): 0.93 (s, 3H), 1.35–1.63 (m, 5H), 1.90 (m, 1H), 2.10 (m, 1H), 2.22–2.40 (m, 4H), 2.47 (s, 3H), 2.85 (m, 2H), 4.41 (d, J=6.3 Hz, 2H), 6.50 (s, 1H), 6.97 (s, 1H), 7.01 (d, J=8.2 Hz, 1H), 7.32 (d, J=8.6 Hz, 1H), 7.87 (br, 2H), 8.39 (br, 1H), 8.45 (m, 2H).

EXAMPLE 50

Compound 50

In a manner similar to that in Step 1-1 in Example 1, the acid chloride of Compound B1 was reacted with 2-(2-aminoethyl)pyridine, and then the 3-position of the reaction product was deprotected with boron tribromide (a 1.0 mol/L dichloromethane solution) to give desulfamoylated Compound 50. Next, in a manner similar to that in Step 5-2 in Example 5, the desulfamoylated Compound 50 was sulfamoylated with sulfamoyl chloride in the presence of sodium hydride to give Compound 50.

ESI-MS m/z: 482 [M+H]$^+$; $^1$H-NMR (CDCl$_3$) δ(ppm): 0.91 (s, 3H), 1.42–1.60 (m, 5H), 1.87 (m, 1H), 2.08 (m, 1H), 2.19–2.39 (m, 4H), 2.84–2.96 (m, 4H), 3.40 (m, 2H), 6.33 (s, 1H), 6.97 (s, 1H), 7.01 (d, J=8.6 Hz, 1H), 7.19–7.26 (m, 2H), 7.33 (d, J=8.6 Hz, 1H), 7.70 (dt, J=1.3, 7.6 Hz, 1H), 7.81–7.90 (m, 3H), 8.49 (d, J=4.9 Hz, 1H).

EXAMPLE 51

Compound 51

In a manner similar to that in Step 1-1 in Example 1, the acid chloride of Compound B1 was reacted with 3-(2-aminoethyl)pyridine, and then the 3-position of the reaction product was deprotected with boron tribromide (a 1.0 mol/L dichloromethane solution) to give desulfamoylated Compound 51. Next, in a manner similar to that in Step 5-2 in Example 5, the desulfamoylated Compound 51 was sulfamoylated with sulfamoyl chloride in the presence of sodium hydride to give Compound 51.

ESI-MS m/z: 482 [M+H]$^+$; $^1$H-NMR (DMSO-d$_6$) δ(ppm): 0.90 (s, 3H), 1.39–1.57 (m, 5H), 1.88 (m, 1H), 2.05 (m, 1H), 2.22–2.38 (m, 4H), 2.78 (m, 2H), 2.85 (m, 2H), 3.40 (m, 2H), 6.32 (s, 1H), 6.97 (s, 1H), 7.02 (d, J=8.6 Hz, 1H), 7.31 (m, 2H), 7.62 (d, J=7.6 Hz, 1H), 7.88 (br, 3H), 8.42 (s, 2H).

EXAMPLE 52

Compound 52

In a manner similar to that in Step 1-1 in Example 1, the acid chloride of Compound B1 was reacted with 4-(2- aminoethyl)pyridine, and then the 3-position of the reaction product was deprotected with boron tribromide (a 1.0 mol/L dichloromethane solution) to give desulfamoylated Compound 52. Next, in a manner similar to that in Step 5-2 in Example 5, the desulfamoylated Compound 52 was sulfamoylated with sulfamoyl chloride in the presence of sodium hydride to give Compound 52.

ESI-MS m/z: 482 [M+H]$^+$; $^1$H-NMR (DMSO-d$_6$) δ(ppm): 0.90 (s, 3H), 1.35–1.58 (m, 5H), 1.88 (m, 1H), 2.05 (m, 1H), 2.20–2.35 (m, 4H), 2.76–2.87 (m, 4H), 3.40 (m, 2H), 6.32 (s, 1H), 6.97 (d, J=2.3 Hz, 1H), 7.02 (d, J=8.6 Hz, 1H), 7.23 (d, J=5.9 Hz, 2H), 7.33 (d, J=8.6 Hz, 1H), 7.89 (br, 3H), 8.46 (d, J=5.9 Hz, 2H).

EXAMPLE 53

Compound 53

In a manner similar to that in Step 4-3 in Example 4, the acid chloride of Compound B3 was reacted with 2-(3-aminopropyl)pyridine, and then the 3-position of the reaction product was deprotected with sodium methoxide (a 28% methanol solution) to give desulfamoylated Compound 53. Next, in a manner similar to that in Step 5-2 in Example 5, the desulfamoylated Compound 53 was sulfamoylated with sulfamoyl chloride in the presence of sodium hydride to give Compound 53.

ESI-MS m/z: 496 [M+H]$^+$; $^1$H-NMR (DMSO-d$_6$) δ(ppm): 0.92 (s, 3H), 1.36–1.58 (m, 5H), 1.74–1.92 (m, 3H), 2.05 (m, 1H), 2.23–2.38 (m, 4H), 2.72 (m, 2H), 2.85 (m, 2H), 3.12 (m, 2H), 6.36 (s, 1H), 6.97 (d, J=2.6 Hz, 1H), 7.01 (d, J=8.3 Hz, 1H), 7.18 (m, 1H), 7.26 (d, J=7.9 Hz, 1H), 7.33 (d, J=8.6 Hz, 1H), 7.68 (m, 1H), 7.80 (br, 1H), 7.87 (br, 2H), 8.47 (d, J=5.0 Hz, 1H).

EXAMPLE 54

Compound 54

In a manner similar to that in Step 6-1 in Example 6, the acid chloride of Compound B3 was reacted with 3-(3-aminopropyl)pyridine hydrochloride in the presence of triethylamine, and then the 3-position of the reaction product was deprotected with sodium methoxide (a 28% methanol solution) to give desulfamoylated Compound 54. Next, in a manner similar to that in Step 5-2 in Example 5, the desulfamoylated Compound 54 was sulfamoylated with sulfamoyl chloride in the presence of sodium hydride to give Compound 54.

ESI-MS m/z: 496 [M+H]$^+$; $^1$H-NMR (DMSO-d$_6$) δ(ppm): 0.92 (s, 3H), 1.37–1.58 (m, 5H), 1.75 (m, 2H), 1.87 (m, 1H), 2.07 (m, 1H), 2.23–2.37 (m, 4H), 2.60 (m, 2H), 2.86 (m, 2H), 3.12 (m, 2H), 6.36 (s, 1H), 6.97 (d, J=2.6 Hz, 1H), 7.02 (dd, J=2.6, 8.3 Hz, 1H), 7.28–7.34 (m, 2H), 7.64 (m, 1H), 7.80 (br, 1H), 7.88 (br, 2H), 8.40 (dd, J=1.6, 4.6 Hz, 1H), 8.44 (d, J=1.0 Hz, 1H).

EXAMPLE 55

Compound 55

In a manner similar to that in Step 4-3 in Example 4, the acid chloride of Compound B3 was reacted with 4-(3-aminopropyl)pyridine, and then the 3-position of the reaction product was deprotected with sodium methoxide (a 28% methanol solution) to give desulfamoylated Compound 55. Next, in a manner similar to that in Step 5-2 in Example 5, the desulfamoylated Compound 55 was sulfamoylated with sulfamoyl chloride in the presence of sodium hydride to give Compound 55.

ESI-MS m/z: 496 [M+H]$^+$; $^1$H-NMR (DMSO-d$_6$) δ(ppm): 0.92 (s, 3H), 1.40–1.60 (m, 5H), 1.76 (m, 2H), 1.89 (m, 1H), 2.06 (m, 1H), 2.23–2.37 (m, 4H), 2.60 (m, 2H), 2.85 (m, 2H), 3.12 (m, 2H), 6.35 (s, 1H), 6.97 (d, J=2.6 Hz, 1H), 7.02 (d, J=8.6 Hz, 1H), 7.24 (d, J=5.9 Hz, 2H), 7.33 (d, J=8.6 Hz, 1H), 7.80 (br, 1H), 7.88 (br, 2H), 8.45 (d, J=5.9 Hz, 2H).

EXAMPLE 56

Compound 56

In a manner similar to that in Step 4-3 in Example 4, the acid chloride of Compound B3 was reacted with 2-(3-aminopropyl)pyrazine, and then the 3-position of the reaction product was deprotected with sodium methoxide (a 28% methanol solution) to give desulfamoylated Compound 56. Next, in a manner similar to that in Step 1-2 in Example 1, the desulfamoylated Compound 56 was sulfamoylated with sulfamoyl chloride to give Compound 56.

ESI-MS m/z: 497 [M+H]$^+$; $^1$H-NMR (DMSO-d$_6$) δ(ppm): 0.92 (s, 3H), 1.31–1.68 (m, 5H), 1.81–1.99 (m, 3H), 2.06 (m, 1H), 2.18–2.46 (m, 4H), 2.75–2.95 (m, 4H), 3.26 (m, 2H), 6.36 (s, 1H), 6.98 (s, 1H), 7.02 (d, J=8.3 Hz, 1H), 7.33 (d, J=8.9 Hz, 1H), 7.81–7.94 (br, 3H), 8.46 (d, J=2.3 Hz, 1H), 8.48 (m, 2H).

EXAMPLE 57

Compound 57

In a manner similar to that in Step 38-1 in Example 38, the acid chloride of Compound B1 was reacted with 2-aminothiazole, and then the 3-position of the reaction product was deprotected with boron tribromide (a 1.0 mol/L dichloromethane solution) in a manner similar to that in Step 1-1 in Example 1 to give desulfamoylated Compound 57. Next, in a manner similar to that in Step 5-2 in Example 5, the desulfamoylated Compound 57 was sulfamoylated with sulfamoyl chloride in the presence of sodium hydride to give Compound 57.

FAB-MS m/z: 460 [M+H]$^+$; $^1$H-NMR (DMSO-d$_6$) δ(ppm): 0.97 (s, 3H), 1.32–1.72 (m, 5H), 1.92 (m, 1H), 2.17 (m, 1H), 2.24–2.47 (m, 4H), 2.88 (m, 2H), 7.00 (d, J=8.6 Hz, 1H), 7.02 (s, 1H), 7.04 (s, 1H), 7.20 (d, J=3.6 Hz, 1H), 7.34 (d, J=8.6 Hz, 1H), 7.49 (d, J=3.6 Hz, 1H), 7.90 (br s, 2H), 12.06 (br, 1H).

EXAMPLE 58

Compound 58

In a manner similar to that in Step 38-1 in Example 38, the acid chloride of Compound B1 was reacted with 3-aminoisoxazole, and then the 3-position of the reaction product was deprotected with boron tribromide (a 1.0 mol/L dichloromethane solution) in a manner similar to that in Step 1-1 in Example 1 to give desulfamoylated Compound 58. Next, in a manner similar to that in Step 5-2 in Example 5, the desulfamoylated Compound 58 was sulfamoylated with sulfamoyl chloride in the presence of sodium hydride to give Compound 58.

FAB-MS m/z: 444 [M+H]$^+$; $^1$H-NMR (DMSO-d$_6$) δ(ppm): 0.96 (s, 3H), 1.33–1.69 (m, 5H), 1.90 (m, 1H), 2.15 (m, 1H), 2.23–2.47 (m, 4H), 2.87 (m, 2H), 6.90 (s, 1H), 6.96 (d, J=1.7 Hz, 1H), 6.98 (d, J=2.3 Hz, 1H), 7.02 (dd, J=2.3, 8.6 Hz, 1H), 7.34 (d, J=8.6 Hz, 1H), 7.89 (s, 2H), 8.78 (d, J=1.7 Hz, 1H), 10.85 (s, 1H).

EXAMPLE 59

Compound 59

In a manner similar to that in Step 38-1 in Example 38, the acid chloride of Compound B3, which was obtained in Step 4-3 in Example 4, was reacted with 3-amino-5-methylisoxazole, and then the 3-position of the reaction product was deprotected with potassium carbonate in a manner similar to that in Step 18-2 in Example 18 to give desulfamoylated Compound. 59. Next, in a manner similar to that in Step 5-2 in Example 5, the desulfamoylated Compound 59 was sulfamoylated with sulfamoyl chloride in the presence of sodium hydride to give Compound 59.

ESI-MS m/z: 458 [M+H]$^+$; $^1$H-NMR (DMSO-d$_6$) δ(ppm): 0.94 (s, 3H), 1.32–1.70 (m, 5H), 1.90 (m, 1H), 2.14 (m, 1H), 2.37 (s, 3H), 2.22–2.47 (m, 4H), 2.87 (m, 2H), 6.66 (s, 1H), 6.87 (s, 1H), 6.98 (s, 1H), 7.01 (d, J=8.6 Hz, 1H), 7.33 (d, J=8.6 Hz, 1H), 7.89 (s, 2H), 10.70 (s, 1H).

EXAMPLE 60

Compound 60

In a manner similar to that in Step 38-1 in Example 38, the acid chloride of Compound B3, which was obtained in Step 4-3 in Example 4, was reacted with 5-amino-3,4-dimethylisoxazole, and then the 3-position of the reaction product was deprotected with potassium carbonate in a manner similar to that in Step 18-2 in Example 18 to give desulfamoylated Compound 60. Next, in a manner similar to that in Step 5-2 in Example 5, the desulfamoylated Compound 60 was sulfamoylated with sulfamoyl chloride in the presence of sodium hydride to give Compound 60.

ESI-MS m/z: 472 [M+H]$^+$; $^1$H-NMR (DMSO-d$_6$) δ(ppm): 0.94 (s, 3H), 1.33–1.70 (m, 5H), 1.78 (s, 3H), 1.90 (m, 1H), 2.15 (s, 3H), 2.08–2.47 (m, 5H), 2.80–2.94 (m, 2H), 6.77 (s, 1H), 6.98 (s, 1H), 7.02 (d, J=8.6 Hz, 1H), 7.33 (d, J=8.6 Hz, 1H), 7.89 (s, 2H), 10.29 (s, 1H).

EXAMPLE 61

Compound 61

In a manner similar to that in Step 38-1 in Example 38, the acid chloride of Compound B3, which was obtained in Step 4-3 in Example 4, was reacted with 2-amino-1,3,4-thiadiazole, and then the 3-position of the reaction product was deprotected with potassium carbonate in a manner similar to that in Step 18-2 in Example 18 to give desulfamoylated Compound 61. Next, in a manner similar to that in Step 5-2 in Example 5, the desulfamoylated Compound 61 was sulfamoylated with sulfamoyl chloride in the presence of sodium hydride to give Compound 61.

FAB-MS m/z: 461 [M+H]$^+$; $^1$H-NMR (DMSO-d$_6$) δ(ppm): 0.96 (s, 3H), 1.34–1.72 (m, 5H), 1.92 (m, 1H), 2.10–2.50 (m, 5H), 2.88 (m, 2H), 6.98 (s, 1H), 7.03 (d, J=8.2 Hz, 1H), 7.12 (s, 1H), 7.34 (d, J=8.2 Hz, 1H), 7.89 (s, 2H), 9.15 (s, 1H), 12.50 (br, 1H).

EXAMPLE 62

Compound 62

In a manner similar to that in Step 38-1 in Example 38, the acid chloride of Compound B3, which was obtained in Step 4-3 in Example 4, was reacted with 5-amino-1-ethylpyrazole, and then the 3-position of the reaction product was deprotected with potassium carbonate in a manner similar to that in Step 18-2 in Example 18 to give desulfamoylated Compound 62. Next, in a manner similar to that in Step 5-2 in Example 5, the desulfamoylated Compound 62 was sulfamoylated with sulfamoyl chloride in the presence of sodium hydride to give Compound 62.

ESI-MS m/z: 471 [M+H]$^+$; $^1$H-NMR (DMSO-d$_6$) δ(ppm): 0.96 (s, 3H), 1.28 (t, J=7.3 Hz, 3H), 1.37–1.73 (m, 5H), 1.92 (m, 1H), 2.08–2.47 (m, 5H), 2.30–2.98 (m, 2H), 3.95 (q, J=7.3 Hz, 2H), 6.13 (s, 1H), 6.71 (s, 1H), 6.98 (s, 1H), 7.02 (d, J=8.6 Hz, 1H), 7.33 (d, J=8.6 Hz, 1H), 7.39 (s, 1H), 7.89 (s, 2H), 9.65 (s, 1H).

EXAMPLE 63

Compound 63

In a manner similar to that in Step 38-1 in Example 38, the acid chloride of Compound B3, which was obtained in Step 4-3 in Example 4, was reacted with 5-aminotetrazole monohydrate, and then the 3-position of the reaction product was deprotected with potassium carbonate in a manner similar to that in Step 18-2 in Example 18 to give desulfamoylated Compound 63. Next, in a manner similar to that in Step 5-2 in Example 5, the desulfamoylated Compound 63 was sulfamoylated with sulfamoyl chloride in the presence of sodium hydride to give Compound 63.

ESI-MS m/z: 445 [M+H]$^+$; $^1$H-NMR (DMSO-d$_6$) δ(ppm): 0.98 (s, 3H), 1.23–1.73 (m, 5H), 1.90 (m, 1H), 2.10–2.50 (m, 5H), 2.87 (m, 2H), 6.98 (s, 1H), 7.02 (d, J=8.6 Hz, 1H), 7.08 (s, 1H), 7.34 (d, J=8.6 Hz, 1H), 7.90 (s, 2H), 11.88 (s, 1H).

EXAMPLE 64

Compound 64

Step 64-1:

3-(Aminomethyl)-1,2,4-oxadiazole hydrochloride (336 mg, 0.247 mmol) and triethylamine (0.138 mL, 0.824 mmol) were dissolved in pyridine (1.4 mL) followed by addition of a dichloromethane solution (1.4 mL) of the acid chloride of Compound B3 (70 mg, 0.21 mmol), which was prepared in Step 4-3 in Example 4, and then the mixture was stirred at room temperature for 3 hours. Water was added to the reaction mixture, and then the mixture was extracted with ethyl acetate. The organic layer was washed with a saturated saline solution, and then dried over anhydrous sodium sulfate. The solvent was evaporated under reduced pressure, and the resulting residue was purified by preparative thin-layer chromatography (chloroform/methanol=40/1) to give Compound B10 (49 mg; yield 56%).

Step 64-2:

Compound B10 (10 mg, 0.023 mmol) was dissolved in THF (0.38 mL) followed by addition of propylamine (9 mg, 0.1 mmol), and then the mixture was stirred at room temperature for 75 hours. The reaction mixture was concentrated, and the resulting residue was purified by preparative thin-layer chromatography (chloroform/acetone=9/1) to give desulfamoylated Compound 64 (9 mg, quantitative).

Step 64-3:

In a manner similar to that in Step 1-2 in Example 1, the desulfamoylated Compound 64 was sulfamoylated with sulfamoyl chloride in the presence of 2,6-di-tert-butyl-4-methylpyridine to give Compound 64.

ESI-MS m/z: 459 [M+H]$^+$; $^1$H-NMR (DMSO-d$_6$) δ(ppm): 0.91 (s, 3H), 1.42–1.57 (m, 5H), 1.89 (m, 1H), 2.08 (m, 1H), 2.30 (m, 4H), 2.86 (m, 2H), 4.47 (d, J=6.3 Hz, 2H), 6.49 (br s, 1H), 6.97 (br s, 1H), 7.01 (d, J=8.6 Hz, 1H), 7.33 (d, J=8.6 Hz, 1H), 7.88 (br s, 2H), 8.44 (t, J=5.8 Hz, 1H), 9.53 (s, 1H).

EXAMPLE 65

Compound 65

In a manner similar to that in Step 18-1 in Example 18, Compound B3 was reacted with 2-(aminoethyl)-1-methylpyrrole in the presence of EDCI and HOBt, and then the 3-position of the reaction product was deprotected with potassium carbonate in a manner similar to that in Step 18-2 in Example 18 to give desulfamoylated Compound 65. Next, in a manner similar to that in Step 1-2 in Example 1, the desulfamoylated Compound 65 was sulfamoylated with sulfamoyl chloride in the presence of 2,6-di-tert-butyl-4-methylpyridine to give Compound 65.

FAB-MS m/z: 484 [M+H]$^+$; $^1$H-NMR (DMSO-d$_6$) δ(ppm): 0.92 (s, 3H), 1.40–1.57 (m, 5H), 1.88 (m, 1H), 2.08 (m, 1H), 2.31 (m, 4H), 2.75 (m, 2H), 2.87 (m, 2H), 3.45 (m, 2H), 3.69 (s, 3H), 5.91 (t, J=4.0 Hz, 1H), 6.36 (s, 1H), 6.49 (d, J=3.6 Hz, 1H), 6.97 (s, 1H), 7.01 (d, J=8.6 Hz, 1H), 7.32 (m, 4H), 7.88 (br s, 1H), 7.95 (t, J=5.6 Hz, 1H).

EXAMPLE 66

Compound 66

In a manner similar to that in Step 18-1 in Example 18, Compound B3 was reacted with 1-(3-aminopropyl) imidazole in the presence of EDCI and HOBt, and then the 3-position of the reaction product was deprotected with potassium carbonate in a manner similar to that in Step 18-2 in Example 18 to give desulfamoylated Compound 66. Next, in a manner similar to that in Step 5-2 in Example 5, the desulfamoylated Compound 66 was sulfamoylated with sulfamoyl chloride in the presence of sodium hydride to give Compound 66.

FAB-MS m/z: 485 [M+H]$^+$; $^1$H-NMR (DMSO-d$_6$) δ(ppm): 0.92 (s, 3H), 1.41–1.54 (m, 5H), 1.86 (m, 3H), 2.05 (m, 1H), 2.31 (m, 4H), 2.86 (m, 2H), 3.07 (m, 2H), 3.96 (t, J=6.8 Hz, 1H), 6.38 (s, 3H), 6.89 (s, 1H), 6.97 (s, 1H), 7.01 (d, J=8.6 Hz, 1H), 7.19 (s, 1H), 7.33 (d, J=8.6 Hz, 1H), 7.64 (s, 1H), 7.84 (t, J=5.6 Hz, 1H), 7.89 (s, 2H), 8.31 (s, 1H).

EXAMPLE 67

Compound 67

In a manner similar to that in Step 4-3 in Example 4, the acid chloride of Compound B3 was reacted with 1-(3-aminopropyl)-2-pyrrolidinone, and then the 3-position of the reaction product was deprotected with sodium methoxide (a 28% methanol solution) to give desulfamoylated Compound 67. Next, in a manner similar to that in Step 5-2 in Example 5, the desulfamoylated Compound 67 was sulfamoylated with sulfamoyl chloride in the presence of sodium hydride to give Compound 67.

ESI-MS m/z: 502 [M+H]$^+$; $^1$H-NMR (DMSO-d$_6$) δ(ppm): 0.92 (s, 3H), 1.45–1.63 (m, 7H), 1.89–2.10 (m, 4H), 2.19–2.37 (m, 6H), 2.86 (m, 2H), 3.06 (m, 2H), 3.18 (m, 2H), 3.27 (m, 2H), 6.37 (d, J=1.4 Hz, 1H), 6.97 (d, J=2.3 Hz, 1H), 7.01 (dd, J=2.6, 8.3 Hz, 1H), 7.33 (d, J=8.6 Hz, 1H), 7.73 (br, 1H), 7.88 (br, 2H).

EXAMPLE 68

Compound 68

In a manner similar to that in Step 6-1 in Example 6, the acid chloride of Compound B3 was reacted with O-(2-pyridylmethyl)hydroxylamine hydrochloride in the presence of triethylamine, and then the 3-position of the reaction product was deprotected with sodium methoxide (a 28% methanol solution) in a manner similar to that in Step 4-3 in Example 4 to give desulfamoylated Compound 68. Next, in a manner similar to that in Step 5-2 in Example 5, the desulfamoylated Compound 68 was sulfamoylated with sulfamoyl chloride in the presence of sodium hydride to give Compound 68.

ESI-MS m/z: 484 [M+H]$^+$; $^1$H-NMR (DMSO-d$_6$) δ(ppm): 0.92 (s, 3H), 1.32–1.58 (m, 5H), 1.89 (m, 1H), 2.07 (m, 1H), 2.15–2.42 (m, 4H), 2.85 (m, 2H), 4.91 (s, 2H), 6.31 (s, 1H), 6.97 (d, J=2.6 Hz, 1H), 7.02 (d, J=8.3 Hz, 1H), 7.31–7.38 (m, 2H), 7.57 (d, J=7.9 Hz, 1H), 7.79–7.94 (m, 4H), 8.54 (d, J=4.6 Hz, 1H).

EXAMPLE 69

Compound 69

In a manner similar to that in Step 4-3 in Example 4, the acid chloride of Compound B3 was reacted with 2-pyridylhydrazine, and then the 3-position of the reaction product was deprotected with sodium methoxide (a 28% methanol solution) to give desulfamoylated Compound 69. Next, in a manner similar to that in Step 1-2 in Example 1, the desulfamoylated Compound 69 was sulfamoylated with sulfamoyl chloride in the presence of 2,6-di-tert-butyl-4-methylpyridine to give Compound 69.

ESI-MS m/z: 469 [M+H]$^+$; $^1$H-NMR (DMSO-d$_6$) δ(ppm): 0.94 (s, 3H), 1.40–1.67 (m, 5H), 1.90 (m, 1H), 2.13 (m, 1H), 2.23–2.37 (m, 4H), 2.87 (m, 2H), 6.54 (d, J=8.3 Hz, 1H), 6.60 (s, 1H), 6.68 (m, 1H), 6.98 (s, 1H), 7.01 (d, J=8.3 Hz, 1H), 7.33 (d, J=8.3 Hz, 1H), 7.51 (m, 1H), 7.88 (br, 2H), 8.05 (d, J=3.9 Hz, 1H), 8.20 (s, 1H), 9.73 (s, 1H).

EXAMPLE 70

Compound 70

Step 70-1:

In a manner similar to that in Step 64-1 in Example 64, the acid chloride of Compound B3, which was prepared in Step 4-3 in Example 4, was reacted with 2-(methylsulfonyl) ethanol in the presence of triethylamine to give Compound B11.

Step 70-2:

Sodium hydride (6 mg, 0.1 mmol, 60% dispersion in oil) was suspended in anhydrous THF (0.4 mL) followed by addition of 2-(methylsulfonyl)ethanol (23 mg, 0.18 mmol) under ice-cooling, and then the mixture was stirred at the same temperature for 1.5 hours. Compound B11 (21 mg, 0.046 mmol), which was dissolved in THF (0.4 mL), was added to the reaction mixture, and the mixture was stirred at the same temperature for 40 minutes. Water was added to the reaction mixture, and then the mixture was extracted with ethyl acetate. The organic layer was washed with a saturated saline solution, and then dried over anhydrous sodium sulfate. The solvent was evaporated under reduced pressure, and the resulting residue was purified by preparative thin-layer chromatography (chloroform/methanol=20/1) to give desulfamoylated Compound 70 (6 mg; yield 31%).

Step 70-3:

In a manner similar to that in Step 1-2 in Example 1, the desulfamoylated Compound 70 was sulfamoylated with sulfamoyl chloride in the presence of 2,6-di-tert-butyl-4-methylpyridine to give Compound 70.

$^1$H-NMR (DMSO-d$_6$) δ(ppm): 0.89 (s, 3H), 1.41–1.65 (m, 5H), 1.88 (m, 1H), 2.13 (m, 1H), 2.29–2.40 (m, 4H), 2.85 (m, 2H), 3.03 (s, 3H), 3.55 (t, J=5.8 Hz, 2H), 4.44 (t, J=5.8 Hz, 2H), 6.83 (br s, 1H), 6.97 (br s, 1H), 7.01 (d, J=8.6 Hz, 1H), 7.33 (d, J=8.6 Hz, 1H), 7.88 (br s, 2H).

EXAMPLE 71

Compound 71

In a manner similar to that in Step 64-1 in Example 64, the acid chloride of Compound B3 was reacted with diethylene glycol monomethyl ether in the presence of triethylamine, and then the 3-position of the reaction product was deprotected with diethylene glycol monomethyl ether and sodium hydride in a manner similar to that in Step 70-2 in Example 70 to give desulfamoylated Compound 71. Next, in a manner similar to that in Step 1-2 in Example 1, the desulfamoylated Compound 71 was sulfamoylated with sulfamoyl chloride in the presence of 2,6-di-tert-butyl-4-methylpyridine to give Compound 71.

ESI-MS m/z: 480 [M+H]$^+$; $^1$H-NMR (DMSO-d$_6$) δ(ppm): 0.89 (s, 3H), 1.38–1.70 (m, 5H), 1.89 (m, 1H), 2.12 (m, 1H), 2.34 (m, 4H), 2.87 (m, 2H), 3.24 (s, 3H), 3.45 (m, 2H), 3.54 (m, 2H), 3.64 (t, J=4.8 Hz, 2H), 4.19 (t, J=4.6 Hz, 2H), 6.78 (br s, 1H), 6.98 (d, J=2.6 Hz, 1H), 7.02 (dd, J=2.5, 8.4 Hz, 1H), 7.34 (d, J=8.6 Hz, 1H), 7.89 (br s, 2H).

EXAMPLE 72

Compound 72

In a manner similar to that in Step 64-1 in Example 64, the acid chloride of Compound B3 was reacted with tetrahydro-4H-pyran-4-ol in the presence of triethylamine, and then the 3-position of the reaction product was deprotected with tetrahydro-4H-pyran-4-ol and sodium hydride in a manner similar to that in Step 70-2 in Example 70 to give desulfamoylated Compound 72. Next, in a manner similar to that in Step 1-2 in Example 1, the desulfamoylated Compound 72 was sulfamoylated with sulfamoyl chloride in the presence of 2,6-di-tert-butyl-4-methylpyridine to give Compound 72.

ESI-MS m/z: 462 [M+H]$^+$; $^1$H-NMR (DMSO-d$_6$) δ(ppm): 0.91 (s, 3H), 1.38–1.71 (m, 7H), 1.89 (m, 3H), 2.12 (m, 1H), 2.34 (m, 4H), 2.87 (m, 2H), 3.51 (m, 2H), 3.79 (m, 2H), 4.96 (m, 1H), 6.81 (br s, 1H), 6.98 (br s, 1H), 7.02 (br d, J=8.6 Hz, 1H), 7.34 (d, J=8.9 Hz, 1H), 7.89 (br s, 2H).

EXAMPLE 73

Compound 73

Compound 1 (425 mg, 0.987 mmol) was dissolved in ethanol (20 mL) followed by addition of 10% palladium on carbon (28 mg, 50% water), and then the mixture was stirred in a hydrogen atmosphere at room temperature for 14 hours. The reaction mixture was filtered through Celite, and the resulting filtrate was concentrated. The resulting residue thus obtained was triturated with ethanol (50 mL) to give Compound 73 (177 mg; yield 41%).

ESI-MS m/z: 433 [M+H]$^+$; $^1$H-NMR (DMSO-d$_6$) δ(ppm): 0.67 (s, 3H), 1.20–1.92 (m, 14H), 2.00–2.36 (m, 3H), 2.66 (t, J=8.6 Hz, 1H), 2.76–2.90 (m, 2H), 3.20–3.60 (m, 4H), 6.95 (d, J=2.6 Hz, 1H), 7.00 (dd, J=2.6, 8.6 Hz, 1H), 7.31 (d, J=8.6 Hz, 1H), 7.83 (br s, 2H).

EXAMPLE 74

Compound 74

In a manner similar to that in Example 73, Compound 74 was obtained by catalytic reduction of Compound 13.

FAB-MS m/z: 450 [M+H]$^+$; $^1$H-NMR (DMSO-d$_6$) δ(ppm): 0.59 (s, 3H), 1.24–1.48 (m, 6H), 1.70 (m, 2H), 1.88 (m, 2H), 2.03–2.38 (m, 11H), 2.83 (m, 2H), 3.08 (m, 2H), 3.27 (m, 1H), 6.96 (d, J=2.3 Hz, 1H), 7.01 (dd, J=2.6, 8.6 Hz, 1H), 7.35 (d, J=8.6 Hz, 1H), 7.38 (br, 1H), 7.88 (br, 2H).

EXAMPLE 75

Compound 75

In a manner similar to that in Example 73, Compound 75 was obtained by catalytic reduction of Compound 17.

FAB-MS m/z: 464 [M+H]$^+$; $^1$H-NMR (DMSO-d$_6$) δ(ppm): 0.59 (s, 3H), 1.29–1.49 (m, 6H), 1.71 (m, 2H), 1.80 (s, 3H), 1.84 (m, 2H), 2.06 (m, 1H), 2.19 (m, 2H), 2.33 (m, 1H), 2.83 (m, 2H), 3.02–3.11 (m, 3H), 3.21 (m, 1H), 6.96 (d, J=2.3 Hz, 1H), 7.01 (dd, J=2.6, 8.6 Hz, 1H), 7.35 (d, J=8.6 Hz, 1H), 7.53 (br, 1H), 7.88 (br, 3H).

EXAMPLE 76

Compound 76

In a manner similar to that in Example 73, Compound 76 was obtained by catalytic reduction of Compound 18.

FAB-MS m/z: 437 [M+H]$^+$; $^1$H-NMR (DMSO-d$_6$) δ(ppm): 0.59 (s, 3H), 1.30 (m, 5H), 1.42–1.89 (m, 4H), 2.27 (m, 4H), 2.83 (m, 2H), 3.24 (s, 3H), 3.35 (m, 4H), 6.96 (d, J=2.3 Hz, 1H), 7.01 (dd, J=2.6, 8.6 Hz, 2H), 7.34 (d, J=8.6 Hz, 2H), 7.50 (m, 1H), 7.87 (br, 2H).

EXAMPLE 77

Compound 77

In a manner similar to that in Example 73, Compound 77 was obtained by catalytic reduction of Compound 22.

FAB-MS m/z: 451 [M+H]$^+$; $^1$H-NMR (DMSO-d$_6$) δ(ppm): 0.59 (s, 3H), 1.24–1.54 (m, 9H), 1.67 (m, 2H), 1.86 (m, 2H), 2.05–2.34 (m, 4H), 2.82 (br, 2H), 2.92 (m, 2H), 3.18 (m, 2H), 4.40 (br, 1H), 6.96 (br s, 1H), 7.00 (d, J=8.6 Hz, 2H), 7.34 (d, J=8.6 Hz, 2H), 7.48 (t, J=5.3 Hz, 1H), 7.84 (br, 2H).

EXAMPLE 78

Compound 78

In a manner similar to that in Example 73, Compound 78 was obtained by catalytic reduction of Compound 29.

FAB-MS m/z: 493 [M+H]$^+$; $^1$H-NMR (CDCl$_3$) δ(ppm): 0.70 (s, 3H), 0.92 (d, J=6.9 Hz, 3H), 0.96 (d, J=6.9 Hz, 3H), 1.26–1.54 (m, 6H), 1.82–1.94 (m, 3H), 2.09–2.30 (m, 6H), 2.88 (m, 2H), 3.75 (s, 3H), 4.62 (m, 1H), 4.98 (s, 2H), 5.82 (d, J=8.2 Hz, 1H), 7.04 (br s, 1H), 7.07 (br d, J=8.9 Hz, 1H), 7.29 (d, J=8.9 Hz, 1H).

EXAMPLE 79

Compound 79

In a manner similar to that in Example 73, Compound 79 was obtained by catalytic reduction of Compound 33.

FAB-MS m/z: 491 [M+H]$^+$; $^1$H-NMR (CDCl$_3$) δ(ppm): 0.78 (s, 3H), 1.39–1.58 (m, 9H), 1.81–1.96 (m, 4H), 2.10–2.28 (m, 4H), 2.66 (t, J=9.6 Hz, 1H), 2.87 (m, 2H), 3.65–3.71 (m, 2H), 3.72 (s, 3H), 4.51 (m, 1H), 5.04 (s, 2H), 7.04 (br s, 1H), 7.07 (d, J=8.9 Hz, 1H), 7.28 (d, J=8.9 Hz, 1H).

EXAMPLE 80

Compound 80

In a manner similar to that in Example 73, Compound 80 was obtained by catalytic reduction of Compound 38.

FAB-MS m/z: 456 [M+H]$^+$; $^1$H-NMR (DMSO-d$_6$) δ(ppm): 0.67 (s, 3H), 1.26–1.50 (m, 5H), 1.65–1.93 (m, 5H), 2.07–2.42 (m, 3H), 2.70 (m, 1H), 2.83 (m, 2H), 6.96 (d, J=2.3 Hz, 1H), 7.01 (dd, J=2.3, 8.6 Hz, 1H), 7.08 (dd, J=4.5, 7.5 Hz, 1H), 7.35 (d, J=8.6 Hz, 1H), 7.76 (dd, J=7.5, 8.6 Hz, 1H), 7.88 (s, 2H), 8.10 (d, J=8.6 Hz, 1H), 8.30 (dd, J=0.7, 4.5 Hz, 1H), 10.08 (s, 1H).

EXAMPLE 81

Compound 81

Step 81-1:

Ethyl [17(20)E]-3-methoxy-19-norpregna-1,3,5(10),17(20)-tetraen-21-oate (Compound B12, 382 mg, 1.08 mmol), which was obtained according to the method described in *Chemische Berichte*, Vol. 111, p. 3094 (1978), was dissolved in ethanol (10 mL) followed by addition of an aqueous lithium hydroxide solution (1.0 mol/L, 10 mL), and then the mixture was refluxed for 1 hour. Hydrochloric acid was added to the reaction mixture, and the resulting precipitate was collected by filtration to give Compound B13 (306 mg; yield 93%).

Step 81-2:

Compound B13 (302 mg, 0.926 mmol) was dissolved in dichloromethane (5 mL) followed by addition of oxalyl chloride (0.316 mL, 3.70 mmol), and then the mixture was stirred at room temperature for 2 hours. The reaction mixture was concentrated, and the resulting acid chloride of Compound B13 was dissolved in dichloromethane (5 mL), followed by addition of propylamine (0.310 mL, 3.77 mmol), and then the mixture was stirred at room temperature for 1 hour. The reaction mixture was concentrated, and the resulting residue was purified by silica gel column chromatography (chloroform/methanol=50/1) to give Compound B14 (368 mg; yield 100%).

Step 81-3:

In a manner similar to that in Step 1-1 in Example 1, Compound B14 was treated with boron tribromide (a 1.0 mol/L dichloromethane solution), and then sulfamoylated with sulfamoyl chloride in a manner similar to that in Step 1-2 in Example 1 to give Compound 81.

ESI-MS m/z: 433 [M+H]$^+$; $^1$H-NMR (DMSO-d$_6$) δ(ppm): 0.79 (s, 3H), 0.83 (t, J=7.3 Hz, 3H), 1.45–1.80 (m, 7H), 1.70–2.00 (m, 3H), 2.16–2.56 (m, 3H), 2.70–2.90 (m, 4H), 3.00 (dt, J=5.6, 6.9 Hz, 2H), 5.56 (br s, 1H), 6.96 (d, J=2.3 Hz, 1H), 7.00 (dd, J=2.3, 8.6 Hz, 1H), 7.34 (d, J=8.6 Hz, 1H), 7.72 (br t, J=5.6 Hz, 1H), 7.84 (br s, 2H).

EXAMPLE 82

Compound 82

Step 82-1:

In a manner similar to that in Example 73, Compound B15 was obtained by catalytic reduction of Compound B12. Next, the 3-position of Compound B15 was deprotected with boron tribromide (a 1.0 mol/L dichloromethane solution) in a manner similar to that in Step 1-1 in Example 1 to give Compound B16 (270 mg; yield 83%).

Step 82-2:

Compound B16 (91 mg, 0.27 mmol) was dissolved in ethanol (5 mL) followed by addition of an aqueous potassium hydroxide solution (1 mol/L, 5 mL), and then the mixture was stirred at room temperature for 3 hours. Hydrochloric acid (1 mol/L) was added to the reaction mixture under ice-cooling, and then the mixture was extracted with ethyl acetate. After the organic layer was washed with a saturated saline solution and dried over anhydrous sodium sulfate, the solvent was evaporated under reduced pressure. The resulting residue was purified by preparative thin-layer chromatography (chloroform/methanol=40/1) to give Compound B17 (58 mg; yield 69%).

Step 82-3:

In a manner similar to that in Step 1-2 in Example 1, Compound B17 was sulfamoylated with sulfamoyl chloride in the presence of 2,6-di-tert-butyl-4-methylpyridine to give Compound 82.

FAB-MS m/z: 394 [M+H]$^+$; $^1$H-NMR (CD$_3$OD) δ(ppm): 0.68 (s, 3H), 1.24–1.51 (m, 6H), 1.87–2.09 (m, 7H), 2.12 (dd, J=9.6, 14.5 Hz, 1H), 2.29 (m, 1H), 2.40 (dd, J=4.9, 14.5 Hz, 1H), 2.87 (m, 2H), 7.00 (br s, 1H), 7.03 (br d, J=8.6 Hz, 1H), 7.31 (d, J=8.6 Hz, 1H).

EXAMPLE 83

Compound 83

In a manner similar to that in Step 5-2 in Example 5, Compound B16 was sulfamoylated with sulfamoyl chloride in the presence of sodium hydride to give Compound 83.

FAB-MS m/z: 422 [M+H]$^+$; $^1$H-NMR (CD$_3$OD) δ(ppm): 0.65 (s, 3H), 1.25 (t, J=7.3 Hz, 3H), 1.28–1.48 (m, 6H), 1.80–2.01 (m, 7H), 2.14 (dd, J=9.2, 14.5 Hz, 1H), 2.26 (m, 1H), 2.39 (dd, J=5.0, 14.5 Hz, 1H), 2.85 (m, 2H), 4.11 (q, J=7.3 Hz, 2H), 7.01 (d, J=2.3 Hz, 1H), 7.03 (dd, J=2.3, 8.3 Hz, 1H), 7.29 (d, J=8.3 Hz, 1H).

EXAMPLE 84

Compound 84

Step 84-1:

Compound B17 (174 mg, 0.555 mmol), ethylamine hydrochloride (194 mg, 2.38 mmol), N-hydroxysuccinimide (149 mg, 1.29 mmol) and triethylamine (0.500 mL, 3.59 mmol) were dissolved in dichloromethane (5 mL) followed by addition of EDCI (250 mg, 1.30 mmol), and then the mixture was stirred at room temperature for 5 hours. Ethyl acetate was added to the reaction mixture, and the organic layer was washed with an aqueous saturated ammonium chloride solution, hydrochloric acid (1 mol/L) and a saturated saline solution in that order, and then dried over anhydrous magnesium sulfate. The solvent was evaporated under reduced pressure, and the resulting residue was purified by preparative thin-layer chromatography (chloroform/methanol=20/1) to give desulfamoylated Compound 84 (36 mg; yield 19%).

Step 84-2:

In a manner similar to that in Step 1-2 in Example 1, the desulfamoylated Compound 84 was sulfamoylated with sulfamoyl chloride in the presence of 2,6-di-tert-butyl-4-methylpyridine to give Compound 84.

FAB-MS m/z: 421 [M+H]$^+$; $^1$H-NMR (CDCl$_3$) δ(ppm): 0.63 (s, 3H), 1.15 (t, J=6.9 Hz, 3H), 1.21–1.49 (m, 6H), 1.81–2.04 (m, 7H), 2.20–2.26 (m, 3H), 2.86 (m, 2H), 3.28 (m, 2H), 5.83 (br s, 2H), 7.03 (br s, 1H), 7.06 (br d, J=8.9 Hz, 1H), 7.29 (d, J=8.9 Hz, 1H).

EXAMPLE 85

Compound 85

In a manner similar to that in Step 84-1 in Example 84, Compound B17 was reacted with propylamine in the presence of N-hydroxysuccinimide, triethylamine and EDCI to give desulfamoylated Compound 85. Next, in a manner similar to that in Step 1-2 in Example 1, the desulfamoylated Compound 85 was sulfamoylated with sulfamoyl chloride in the presence of 2,6-di-tert-butyl-4-methylpyridine to give Compound 85.

FAB-MS m/z: 435 [M+H]$^+$; $^1$H-NMR (CDCl$_3$) δ(ppm): 0.64 (s, 3H), 0.93 (t, J=7.3 Hz, 3H), 1.02–1.40 (m, 6H), 1.53

(m, 2H), 1.60–1.96 (m, 7H), 2.01–2.32 (m, 3H), 2.87 (m, 2H), 3.17 (m, 2H), 6.80 (br s, 2H), 7.03 (br s, 1H), 7.06 (br d, J=8.6 Hz, 1H), 7.29 (d, J=8.6 Hz, 1H).

EXAMPLE 86

Compound 86

In a manner similar to that in Step 84-1 in Example 84, Compound B17 was reacted with dimethylamine in the presence of N-hydroxysuccinimide, triethylamine and EDCI to give desulfamoylated Compound 86. Next, in a manner similar to that in Step 1-2 in Example 1, the desulfamoylated Compound 86 was sulfamoylated with sulfamoyl chloride in the presence of 2,6-di-tert-butyl-4-methylpyridine to give Compound 86.

FAB-MS m/z: 421 [M+H]$^+$; $^1$H-NMR (CDCl$_3$) δ(ppm): 0.66 (s, 3H), 1.25–1.59 (m, 7H), 1.81–2.04 (m, 6H), 2.14 (m, 1H), 2.28 (m, 1H), 2.44 (dd, J=3.6, 14.8 Hz, 1H), 2.87 (m, 2H), 2.95 (s, 3H), 3.03 (s, 3H), 4.99 (s, 2H), 7.03 (br s, 1H), 7.07 (br d, J=8.6 Hz, 1H), 7.30 (d, J=8.6 Hz, 1H).

EXAMPLE 87

Compound 87

In a manner similar to that in Step 84-1 in Example 84, Compound B17 was reacted with pyrrolidine in the presence of N-hydroxysuccinimide, triethylamine and EDCI to give desulfamoylated Compound 87. Next, in a manner similar to that in Step 1-2 in Example 1, the desulfamoylated Compound 87 was sulfamoylated with sulfamoyl chloride in the presence of 2,6-di-tert-butyl-4-methylpyridine to give Compound 87.

FAB-MS m/z: 447 [M+H]$^+$; $^1$H-NMR (CDCl$_3$) δ(ppm): 0.65 (s, 3H), 1.21–1.50 (m, 6H), 1.80–2.29 (m, 13H), 2.38 (dd, J=3.6, 14.5 Hz, 1H), 2.86 (m, 2H), 3.46 (m, 4H), 5.16 (s, 2H), 7.04 (br d, J=2.3 Hz, 1H), 7.07 (dd, J=2.3, 8.6 Hz, 1H), 7.29 (d, J=8.6 Hz, 1H).

EXAMPLE 88

Compound 88

In a manner similar to that in Step 84-1 in Example 84, Compound B17 was reacted with morpholine in the presence of N-hydroxysuccinimide, triethylamine and EDCI to give desulfamoylated Compound 88. Next, in a manner similar to that in Step 1-2 in Example 1, the desulfamoylated Compound 88 was sulfamoylated with sulfamoyl chloride in the presence of 2,6-di-tert-butyl-4-methylpyridine to give Compound 88.

FAB-MS m/z: 463 [M+H]$^+$; $^1$H-NMR (CDCl$_3$) δ(ppm): 0.67 (s, 3H), 1.21–1.52 (m, 6H), 1.83–2.31 (m, 9H), 2.44 (dd, J=4.0, 14.8 Hz, 1H), 2.87 (m, 2H), 3.49 (m, 2H), 3.64 (m, 2H), 3.68 (m, 4H), 5.03 (s, 2H), 7.03 (br s, 1H), 7.07 (br d, J=8.2 Hz, 1H), 7.30 (d, J=8.2 Hz, 1H).

EXAMPLE 89

Compound 89

Step 89-1:

17-Cyano-3-hydroxyestra-1,3,5(10),16-tetraene 3-methanesulfinate (Compound B18, 200 mg, 0.559 mmol), which was obtained according to the method described in *The Journal of Organic Chemistry*, Vol. 59, p. 6683 (1994), was dissolved in THF (6 mL) followed by addition of diisobutylaluminium hydride (0.9 mL, 0.8 mmol, a 0.9 mol/L n-hexane solution), and then the mixture was stirred for 1.8 hours under ice-cooling. 5% sulfuric acid was added to the reaction mixture, and then the mixture was extracted with ethyl acetate. The organic layer was washed with a saturated saline solution, and then dried over anhydrous sodium sulfate. The solvent was evaporated under reduced pressure, and the resulting residue was purified by preparative thin-layer chromatography (chloroform/acetone=60/1) to give Compound B19 (96 mg).

ESI-MS m/z: 361 [M+H]$^+$; $^1$H-NMR (CDCl$_3$) δ(ppm): 0.94 (s, 3H), 1.39–2.54 (m, 8H), 2.92 (m, 1H), 3.13 (s, 3H), 6.84 (m, 1H), 7.03 (dd, J=2.6, 8.9 Hz, 1H), 7.31 (d, J=8.3 Hz, 1H), 9.75 (s, 1H).

Step 89-2:

Compound B19 (96 mg) was dissolved in methanol (4 mL) followed by addition of acetic acid (0.1 mL), morpholine (0.146 mL, 1.68 mmol) and sodium triacetoxyborohydride (355 mg, 1.68 mmol), and then the mixture was stirred at room temperature for 12.7 hours. Water was added to the reaction mixture, and then the mixture was extracted with ethyl acetate. The organic layer was washed with a saturated saline solution, and then dried over anhydrous sodium sulfate. The solvent was evaporated under reduced pressure, and the resulting residue was purified by preparative thin-layer chromatography (chloroform/acetone=20/1) to give Compound B20 (41 mg; yield 17%).

ESI-MS m/z: 432 [M+H]$^+$; $^1$H-NMR (CDCl$_3$) δ(ppm): 0.84 (s, 3H), 1.40–1.68 (m, 5H), 1.96 (m, 2H), 2.15–2.38 (m, 4H), 2.44 (m, 4H), 2.88 (m, 2H), 2.94 (d, J=14.5 Hz, 1H), 3.01 (d, J=14.5 Hz, 1H), 3.12 (s, 3H), 3.71 (m, 4H), 5.53 (d, J=1.3 Hz, 1H), 6.99 (d, J=2.3 Hz, 1H), 7.03 (dd, J=2.6, 8.3 Hz, 1H), 7.30 (d, J=8.6 Hz, 1H).

Step 89-3:

Compound B20 (40 mg, 0.093 mmol) was dissolved in methanol (2.4 mL) followed by addition of an aqueous sodium hydroxide solution (6 mol/L, 0.3 mL), and then the mixture was stirred at 60° C. for 2.8 hours. Water and hydrochloric acid (0.5 mol/L) were added to the reaction mixture, and then the mixture was extracted with ethyl acetate. The organic layer was washed with a saturated saline solution and dried over anhydrous sodium sulfate, and the solvent was evaporated under reduced pressure. The resulting residue was purified by preparative thin-layer chromatography (chloroform/methanol=15/1) to give desulfamoylated Compound 89 (27 mg; yield 84%).

Step 89-4:

In a manner similar to that in Step 1-2 in Example 1, the desulfamoylated Compound 89 was sulfamoylated with sulfamoyl chloride in the presence of 2,6-di-tert-butyl-4-methylpyridine to give Compound 89.

ESI-MS m/z: 433 [M+H]$^+$; $^1$H-NMR (DMSO-d$_6$) δ(ppm): 0.81 (s, 3H), 1.39–1.56 (m, 5H), 1.88 (m, 3H), 2.13 (m, 1H), 2.34 (m, 6H), 2.86 (m, 2H), 2.88 (t, J=13.5 Hz, 1H), 2.97 (t, J=13.5 Hz, 1H), 3.32 (s, 3H), 3.56 (m, 4H), 5.51 (br s, 1H), 6.97 (d, J=2.3 Hz, 1H), 7.02 (dd, J=2.5, 8.4 Hz, 1H), 7.33 (d, J=8.6 Hz, 1H), 7.88 (br s, 2H).

EXAMPLE 90

Compound 90

Step 90-1:

Compound B2 (150 mg, 0.337 mmol) was dissolved in THF (6 mL) followed by addition of dichlorobis(triphenylphosphine)palladium(II) (24 mg, 0.034 mmol), diethyl(3-pyridyl)borane (74 mg, 0.51 mmol) and an aqueous sodium carbonate solution (1 mol/L, 2 mL), and then the mixture was stirred in an argon atmosphere at 80° C. for 1.8 hours. Water was added to the reaction mixture, and then the mixture was extracted with ethyl acetate. The organic layer was washed with a saturated saline solution, and then dried over anhydrous sodium sulfate. The solvent was evaporated under reduced pressure, and the resulting residue was purified by preparative thin-layer chromatography (chloroform/methanol=100/1) to give Compound B21 (95 mg; yield 75%).

ESI-MS m/z: 374 [M+H]$^+$; $^1$H-NMR (CDCl$_3$) δ(ppm): 1.03 (s, 3H), 1.40–1.86 (m, 5H), 1.97 (m, 1H), 2.14 (m, 1H), 2.41 (m, 4H), 2.92 (m, 2H), 6.02 (br s, 1H), 6.82 (s, 1H), 6.84 (dd, J=2.6, 8.3 Hz, 1H), 7.22 (dd, J=5.0, 7.9 Hz, 1H), 7.27 (d, J=7.9 Hz, 1H), 7.67 (ddd, J=1.7, 2.0, 7.9 Hz, 1H), 8.47 (dd, J=1.5, 4.8 Hz, 1H), 8.65 (d, J=2.3 Hz, 1H).

Step 90-2:

In a manner similar to that in Step 18-2 in Example 18, Compound B21 was treated with potassium carbonate, and then sulfamoylated with sulfamoyl chloride in the presence of 2,6-di-tert-butyl-4-methylpyridine in a manner similar to that in Step 1-2 in Example 1 to give Compound 90.

ESI-MS m/z: 411 [M+H]$^+$; $^1$H-NMR (DMSO-d$_6$) δ(ppm): 1.02 (s, 3H), 1.45–1.77 (m, 5H), 1.93 (m, 1H), 2.14 (m, 2H), 2.36 (m, 3H), 2.88 (m, 2H), 6.16 (br s, 1H), 6.99 (br s, 1H), 7.03 (dd, J=2.0, 8.6 Hz, 1H), 7.36 (m, 2H), 7.80 (br d, J=7.9 Hz, 1H), 7.89 (br s, 2H), 8.45 (br d, J=5.0 Hz, 1H), 8.62 (d, J=2.0 Hz, 1H).

EXAMPLE 91

Compound 91

Step 91-1:

Compound B3 (406 mg, 1.19 mmol) was dissolved in ether (6 mL) followed by addition of methyllithium (7.0 mL, 7.2 mmol, a 1.03 mol/L ether solution) at −78° C., and then the mixture was stirred for 1.5 hours under ice-cooling. An aqueous saturated ammonium chloride solution was added to the reaction mixture, and then the mixture was extracted with ethyl acetate. The organic layer was washed with a saturated saline solution and dried over anhydrous sodium sulfate, and the solvent was evaporated under reduced pressure. The resulting residue was purified by silica gel column chromatography (chloroform), and then recrystallized from a mixed solvent of ethanol and water to give desulfamoylated Compound 91 (23 mg; yield 6%).

$^1$H-NMR (CDCl$_3$) δ(ppm): 0.99 (s, 3H), 1.43 (s, 6H), 1.46–1.72 (m, 4H), 1.78 (m, 1H), 1.85–2.00 (m, 2H), 2.09–2.40 (m, 4H), 2.75–2.96 (m, 2H), 4.90 (br, 1H), 5.65 (t, J=1.5 Hz, 1H), 6.57 (d, J=2.6 Hz, 1H), 6.62 (dd, J=2.6, 8.6 Hz, 1H), 7.14 (d, J=8.6 Hz, 1H).

Step 91-2:

In a manner similar to that in Step 1-2 in Example 1, the desulfamoylated Compound 91 was sulfamoylated with sulfamoyl chloride in the presence of 2,6-di-tert-butyl-4-methylpyridine to give Compound 91.

ESI-MS m/z: 374 [M-OH]$^+$; $^1$H-NMR (CDCl$_3$) δ(ppm): 0.99 (s, 3H), 1.429 (s, 3H), 1.432 (s, 3H), 1.15–2.08 (m, 7H), 2.10–2.43 (m, 4H), 2.91 (m, 2H), 4.97 (s, 2H), 5.66 (d, J=1.7 Hz, 1H), 7.05 (s, 1H), 7.08 (d, J=8.6 Hz, 1H), 7.30 (d, J=8.6 Hz, 1H).

EXAMPLE 92

Compound 92

Step 92-1:

The acid chloride of Compound B3 (503 mg, 1.48 mmol), which was obtained in Step 4-3 in Example 4, was dissolved in THF (10 mL) followed by addition of 28% aqueous ammonia (3.0 mL), and then the mixture was stirred at room temperature for 23.5 hours. Methanol and hydrochloric acid (1 mol/L) were added to the reaction mixture, and the resulting precipitate was collected by filtration and dried under reduced pressure to give Compound B22.

ESI-MS m/z: 298 [M+H]$^+$; $^1$H-NMR (DMSO-d$_6$) δ(ppm): 0.89 (s, 3H), 1.22–1.61 (m, 5H), 1.83 (m, 1H), 2.02 (m, 1H), 2.08–2.39 (m, 4H), 2.63–2.87 (m, 2H), 6.44 (s, 2H), 6.51 (d, J=8.6 Hz, 1H), 6.73 (s, 1H), 7.03 (d, J=8.6 Hz, 1H), 7.23 (s, 1H), 9.00 (m, 1H).

Step 92-2:

Compound B22 (134 mg, 0.451 mmol) was dissolved in DMF (3 mL) followed by addition of chloroacetone (0.430 mL, 5.40 mmol), and then the mixture was stirred at 100° C. for 7.5 hours. Chloroacetone (0.430 mL, 5.40 mmol) was further added to the reaction mixture and then the mixture was stirred at the same temperature for 3 hours. The reaction mixture was concentrated, and then the resulting residue was purified by preparative thin-layer chromatography (chloroform/methanol=40/1) to give desulfamoylated Compound 92 (96 mg; yield 63%).

ESI-MS m/z: 336 [M+H]$^+$; $^1$H-NMR (DMSO-d$_6$) δ(ppm): 0.94 (s, 3H), 1.30–1.77 (m, 5H), 1.87 (m, 1H), 2.10 (s, 3H), 2.06–2.27 (m, 2H), 2.27–2.43 (m, 2H), 2.48–2.59 (m, 1H), 2.68–2.84 (m, 2H), 6.46 (s, 1H), 6.49 (s, 1H), 6.52 (d, J=8.6 Hz, 1H), 7.05 (d, J=8.6 Hz, 1H), 7.72 (s, 1H), 9.02 (s, 1H).

Step 92-3:

In a manner similar to that in Step 1-2 in Example 1, the desulfamoylated Compound 92 was sulfamoylated with sulfamoyl chloride to give Compound 92.

APCI-MS m/z: 415 [M+H]$^+$; $^1$H-NMR (DMSO-d$_6$) δ(ppm): 0.95 (s, 3H), 1.35–1.79 (m, 5H), 1.92 (m, 1H), 2.10 (s, 3H), 2.16 (m, 1H), 2.25–2.47 (m, 3H), 2.54 (m, 1H), 2.88 (m, 2H), 6.50 (s, 1H), 6.99 (s, 1H), 7.03 (d, J=8.6 Hz, 1H), 7.35 (d, J=8.6 Hz, 1H), 7.73 (s, 1H), 7.89 (s, 2H).

EXAMPLE 93

Compound 93

Step 93-1:

The acid chloride of Compound B3 (403 mg, 1.12 mmol), which was obtained in Step 4-3 in Example 4, was dissolved in THF (12 mL) followed by addition of isopropyl-(2-methoxymethoxy-1-methylethyl)amine (722 mg, 1.12 mmol), which was obtained in Reference Example 5, triethylamine (0.187 mL, 1.34 mmol) and DMAP (164 mg, 1.34 mmol), and then the mixture was stirred at room temperature for 9.5 hours and then at 60° C. for 14.5 hours. Water was added to the reaction mixture, and then the mixture was extracted with ethyl acetate. The organic layer was washed with a saturated saline solution and dried over anhydrous sodium sulfate, and the solvent was evaporated under reduced pressure. The resulting residue was purified by preparative thin-layer chromatography (chloroform/methanol=40/1) to give Compound B23 (332 mg; yield 61%).

APCI-MS m/z: 484 [M+H]$^+$; $^1$H-NMR (CDCl$_3$) δ(ppm): 1.08 (s, 3H), 1.20–1.26 (br, 6H), 1.46 (br, 3H), 1.64 (br, 5H), 1.93 (br, 3H), 2.15 (br, 1H), 2.28 (s, 3H), 2.33 (br, 3H), 2.91 (br, 2H), 3.36 (d, J=2.5 Hz, 3H), 3.78–4.13 (br, 2H), 4.33 (br, 1H), 4.62 (d, J=3.3 Hz, 2H), 4.74 (m, 1H), 5.71 (s, 1H), 6.80 (s, 1H), 6.83 (d, J=8.4 Hz, 1H), 7.25 (d, J=2.8 Hz, 1H).

Step 93-2:

In a manner similar to that in Step 18-2 in Example 18, Compound B23 was treated with potassium carbonate, and the resulting desulfamoylated Compound 93 (255 mg, 0.577 mmol) was dissolved in DMAC (5.1 mL). Sulfamoyl chloride (133 mg, 1.15 mmol) was added to the mixture, and the mixture was stirred at room temperature for 1.3 hours. Water was added to the reaction mixture, and then the mixture was extracted with ethyl acetate. The organic layer was washed with a saturated saline solution and dried over anhydrous sodium sulfate, and the solvent was evaporated under reduced pressure. The resulting residue was purified by preparative thin-layer chromatography (chloroform/methanol=18/1) to give Compound 93 (287 mg; yield 96%).

APCI-MS m/z: 521 [M+H]$^+$; $^1$H-NMR (DMSO-d$_6$) δ(ppm): 0.98 (s, 3H), 1.12 (br, 6H), 1.32 (br, 3H), 1.50 (br, 5H), 1.84 (br, 2H), 2.06 (br, 1H), 2.33 (br, 3H), 2.85 (br, 2H), 3.26 (d, J=2.0 Hz, 3H), 3.41 (br, 1H), 3.77 (br, 1H), 4.25 (br, 1H), 4.56 (br s, 2H), 4.67 (m, 1H), 5.69 (s, 1H), 6.98 (d, J=2.3 Hz, 1H), 7.02 (dd, J=2.5, 8.4 Hz, 1H), 7.32 (d, J=8.6 Hz, 1H), 7.89 (s, 2H).

EXAMPLE 94

Compound 94

Compound 93 (146 mg, 0.280 mmol) was dissolved in dichloromethane (4.4 mL) followed by addition of thiophenol (0.144 mL, 1.40 mmol) and a boron trifluoride-diethyl ether complex (0.11 mL, 0.84 mmol), and then the mixture was stirred at room temperature for 1.3 hours. An aqueous saturated sodium hydrogencarbonate solution was added to the reaction mixture, and then the mixture was extracted with ethyl acetate. The organic layer was washed with a saturated saline solution and dried over anhydrous sodium sulfate, and the solvent was evaporated under reduced pressure. The resulting residue was purified by preparative thin-layer chromatography (chloroform/methanol=15/1) to give Compound 94 (198 mg; yield 88%).

APCI-MS m/z: 475 [M−H]$^−$; $^1$H-NMR (DMSO-d$_6$) δ(ppm): 0.98 (d, J=1.7 Hz, 3H), 1.03–1.40 (br, 9H), 1.50 (m, 5H), 1.85 (br, 2H), 2.06 (br, 1H), 2.32 (br, 3H), 2.87 (br, 2H), 3.22–3.64 (br, 2H), 4.23 (br, 1H), 4.75 (m, 1H), 5.70 (brs, 1H), 6.98 (s, 1H), 7.01 (dd, J=2.3, 8.6 Hz, 1H), 7.32 (d, J=8.6 Hz, 1H), 7.88 (s, 2H).

EXAMPLE 95

Compound 95

An acetone solution (1 mL) of Compound 94 (60 mg, 0.13 mmol) was added to an acetone solution (0.5 mL) of Jones reagent (chromium(VI) oxide-sulfuric acid-acetone) (0.133 mL) under ice-cooling, and the mixture was stirred at the same temperature for 2 hours. Further, Jones reagent (0.266 mL) divided into two parts was added thereto at different times, and then the mixture was stirred for 24 hours. Next, isopropyl alcohol (0.3 mL) was added to the reaction mixture, and the mixture was stirred at room temperature for 0.5 hours. Water was added to the reaction mixture, and then the mixture was extracted with ethyl acetate. The organic layer was washed with a saturated saline solution and dried over anhydrous sodium sulfate, and the solvent was evaporated under reduced pressure. The resulting residue was purified by preparative thin-layer chromatography (chloroform/methanol=12/1) to give Compound 95 (21 mg; yield 33%).

APCI-MS m/z: 489 [M−H]$^−$; $^1$H-NMR (DMSO-d$_6$) δ(ppm): 0.86 (s, 3H), 1.14–1.53 (m, 14H), 1.87–2.23 (m, 2H), 2.15 (m, 1H), 2.27–2.38 (m, 3H), 2.87 (br, 2H), 3.93 (m, 1H), 4.35 (br, 1H), 5.73 (m, 1H), 6.98 (s, 1H), 7.01 (d, J=8.6Hz, 1H), 7.33 (m, 1H), 7.89 (brs, 2H), 11.96 (br, 1H).

Methods for producing the compounds used in the Examples are described below.

REFERENCE EXAMPLE 1

2-(tert-Butyldimethylsilyloxy)ethylamine

Ethanolamine (2.00 g, 32.7 mmol) was dissolved in DMF (15 mL) followed by addition of imidazole (1.11 g, 16.4 mmol) and tert-butyldimethylsilyl chloride (2.46 g, 16.4 mmol), and then the mixture was stirred at room temperature for 12 hours. Water and an aqueous saturated sodium hydrogencarbonate solution were added to the reaction mixture in that order, and then the mixture was extracted with ethyl acetate. The organic layer was washed with a saturated saline solution and dried over anhydrous sodium sulfate, and the solvent was evaporated under reduced pressure. The resulting residue was purified by silica gel column chromatography (chloroform/methanol=10/1) to give 2-(tert-butyldimethylsilyloxy)ethylamine (1.59 g; yield 56%).

FAB-MS m/z: 176 [M+H]$^+$; $^1$H-NMR (CDCl$_3$) δ(ppm): 0.07 (s, 6H), 0.90 (s, 9H), 2.78 (t, J=5.3 Hz, 2H), 3.63 (t, J=5.3 Hz, 2H).

REFERENCE EXAMPLE 2

4-(tert-Butyldimethylsilyloxy)-1-butylamine

In a manner similar to that in Reference Example 1, 4-amino-1-butanol was reacted with tert-butyldimethylsilyl chloride in the presence of imidazole to give 4-(tert-butyldimethylsilyloxy)-1-butylamine.

$^1$H-NMR (CDCl$_3$) δ(ppm): 0.09 (s, 6H), 0.91 (s, 9H), 1.58 (m, 4H), 3.32 (q, J=6.3 Hz, 2H), 3.64 (t, J=5.8 Hz, 1H).

REFERENCE EXAMPLE 3

2-(3-Aminopropyl)pyrazine

Step 3-1:

Copper iodide (146 mg, 0.768 mmol) was dissolved in triethylamine (2.5 mL) followed by addition of dichlorobis(triphenylphosphine)palladium(II) (180 mg, 0.256 mmol), and then the mixture was stirred at room temperature for 10 minutes. A THF solution (5 mL) of iodopyradine (1.05 g, 5.12 mmol) and N-propargylphthalimide (948 mg, 5.12 mmol), and triethylamine (5 mL) were added to the reaction mixture in that order, and the mixture was stirred under reflux for 1.5 hours. Hydrochloric acid (1 mol/L) was added to the reaction mixture, and then the mixture was extracted with chloroform. The organic layer was washed with a saturated saline solution and dried over anhydrous sodium sulfate, and the solvent was evaporated under reduced pressure. The resulting residue was purified by silica gel column chromatography (hexane/ethyl acetate=2/1) to give N-[3-(2-pyrazinyl)-2-propynyl]phthalimide (780 mg; yield 58%).

$^1$H-NMR (CDCl$_3$) δ(ppm): 4.75 (s, 2H), 7.75–7.78 (m, 2H), 7.88–7.93 (m, 2H), 8.48 (d, J=2.6 Hz, 1H), 8.51 (dd, J=1.7, 2.6 Hz, 1H), 8.65 (d, J=1.0 Hz, 1H).

Step 3-2:

N-[3-(2-Pyrazinyl)-2-propynyl]phthalimide (780 mg, 2.96 mmol) was dissolved in DMF (30 mL) followed by addition of 10% palladium on carbon (500 mg, 50% water), and then the mixture was stirred in a hydrogen atmosphere at room temperature for 5.5 hours. The reaction mixture was filtered through Celite, and the resulting filtrate was concentrated to give N-[3-(2-pyrazinyl)propyl]phthalimide (521 mg; yield 66%).

$^1$H-NMR (CDCl$_3$) δ(ppm): 2.19 (m, 2H), 2.89 (t, J=7.3 Hz, 2H), 3.81 (t, J=6.9 Hz, 2H), 7.70–7.73 (m, 2H), 7.82–7.85 (m, 2H), 8.37 (s, 1H), 8.46 (m, 2H).

Step 3-3:

N-[3-(2-Pyrazinyl)propyl]phthalimide (521 mg, 1.95 mmol) was dissolved in chloroform (15 mL) followed by addition of anhydrous hydrazine (1.5 mL), and then the mixture was stirred at room temperature for 20 hours. The resulting precipitate was removed by filtration, and the filtrate was washed with water and dried over anhydrous sodium sulfate. The solvent was evaporated under reduced pressure, and 2-(3-aminopropyl)pyrazine (240 mg; yield 90%) was thus obtained.

$^1$H-NMR (CDCl$_3$) δ(ppm): 1.43 (br, 2H), 1.90 (m, 2H), 2.77 (t, J=7.3 Hz, 2H), 2.88 (t, J=6.9 Hz, 2H), 8.40 (d, J=2.3 Hz, 1H), 8.48 (m, 2H).

REFERENCE EXAMPLE 4

3-(Aminomethyl)-1,2,4-oxadiazole hydrochloride

Step 4-1:

Phthalimide (892 mg, 6.01 mmol) was dissolved in DMF (10 mL) followed by addition of 3-(chloromethyl)-1,2,4-oxadiazole (713 mg, 6.01 mmol), cesium carbonate (2.95 g, 9.02 mmol) and tetrabutylammonium iodide (3.35 g, 8.02 mmol), and then the mixture was stirred at room temperature for 2.5 hours. Water was added to the reaction mixture, and the resulting precipitate was collected by filtration and dried under reduced pressure to give N-(1,2,4-oxadiazol-3-ylmethyl)phthalimide (1.15 g; yield 83%).

ESI-MS m/z: 176 [M+H]$^+$; $^1$H-NMR (CDCl$_3$) δ(ppm): 5.09 (s, 2H), 7.77 (m, 2H), 7.92 (m, 2H), 8.68 (s, 1H).

Step 4-2:

N-(1,2,4-Oxadiazol-3-ylmethyl)phthalimide (1.10 g, 4.78 mmol) was dissolved in chloroform (30 mL) followed by addition of hydrazine monohydrate (0.812 mL, 16.7 mmol), and then the mixture was stirred at room temperature for 4.5 hours. The resulting precipitate was removed by filtration, the filtrate was concentrated, and ethyl acetate (10 mL) was added to the resulting residue. The resulting insoluble substances were removed by filtration. An 4 mol/L ethyl acetate solution of hydrogen chloride (2.65 mL) was added to the resulting filtrate. The resulting precipitate was collected by filtration, and dried under reduced pressure to give 3-(aminomethyl)-1,2,4-oxadiazole hydrochloride (624 mg; yield 96%).

$^1$H-NMR (DMSO-d$_6$) δ(ppm): 4.33 (s, 2H), 8.77 (br s, 3H), 9.77 (s, 1H).

REFERENCE EXAMPLE 5

Isopropyl-(2-methoxymethoxy-1-methylethyl)amine

Step 5-1:

Methyl 2-bromopropionate (10.0 g, 59.9 mmol) was dissolved in acetonitrile (200 mL) followed by addition of isopropylamine (15.3 mL, 180 mmol), potassium carbonate (24.8 g, 180 mmol) and benzyltriethylammonium chloride (1.36 g, 5.99 mmol), and then the mixture was stirred at 70° C. for 17 hours. Water was added to the reaction mixture, and then the mixture was extracted with ethyl acetate. The organic layer was washed with a saturated saline solution, and then dried over anhydrous sodium sulfate. The solvent was evaporated under reduced pressure, and methyl 2-(isopropylamino)propionate (6.70 g; yield 77%) was thus obtained.

APCI-MS m/z: 146 [M+H]$^+$; $^1$H-NMR (CDCl$_3$) δ(ppm): 1.02 (d, J=6.3 Hz, 3H), 1.05 (d, J=6.3 Hz, 3H), 1.29 (d, J=6.9 Hz, 3H), 2.74 (m, 1H), 3.45 (q, J=7.0 Hz, 1H), 3.72 (s, 3H).

Step 5-2:

Lithium aluminium hydride (911 mg, 24.0 mmol) was suspended in ether (26 mL) followed by dropwise addition of an ether solution (20 mL) of methyl 2-(isopropylamino) propionate (2.32 g, 16.0 mmol), under ice-cooling. While gradually warmed up to room temperature, the reaction mixture was stirred for 2 hours, and then sodium sulfate 10-hydrate (8.76 g, 27.2 mmol) was gradually added thereto, and the mixture was stirred at room temperature for 2 hours.

The reaction mixture was filtered through Celite, and the resulting filtrate was concentrated under reduced pressure to give 2-isopropylamino-1-propanol (1.56 g; yield 83%).

APCI-MS m/z: 118 [M+H]$^+$; $^1$H-NMR (CDCl$_3$) δ(ppm): 1. 02 (d, J=6. 1 Hz, 3H), 1.03 (d, J=6.4 Hz, 3H), 1.08 (d, J=6.3 Hz, 3H), 2.84 (m, 1H), 2.92 (m, 1H), 3.16 (m, 1H), 3.51 (m, 1H).

Step 5-3:

A THF solution (15 mL) of 2-isopropylamino-1-propanol (1.23 g, 10.5 mmol) was added dropwise to a suspension of sodium hydride (504 mg, 0.29 mmol, 60% oil) in THF (9 mL), and the mixture was stirred at the same temperature for 15 minutes. Next, chloromethyl methyl ether (1.20 mL, 15.8 mmol) was added thereto, and the mixture stirred at room temperature for 45 minutes. An aqueous saturated sodium hydrogencarbonate solution was added to the reaction mixture, and then the mixture was extracted with ethyl acetate. The organic layer was washed with a saturated saline solution, and then dried over anhydrous sodium sulfate. The solvent was evaporated under reduced pressure, and isopropyl-(2-methoxymethoxy-1-methylethyl)amine (0.91 g; yield 54%) was thus obtained. $^1$H-NMR (CDCl$_3$) δ(ppm): 1.05 (d, J=6.1 Hz, 3H), 1.06 (d, J=5.3 Hz, 3H), 1.08 (d, J=5.3 Hz, 3H), 2.94 (m, 2H), 3.36 (s, 3H), 3.38 (m, 1H), 3.47 (m, 1H), 4.63 (s, 2H).

PREPARATION EXAMPLE 1

Tablets

Tablets having the following composition are prepared in a usual manner.

| Compound 1 | 5 mg |
|---|---|
| Lactose | 60 mg |
| Potato starch | 30 mg |
| Polyvinyl alcohol | 2 mg |
| Magnesium stearate | 1 mg |
| Tar colorant | a little |

PREPARATION EXAMPLE 2

Granules

Granules having the following composition are prepared in a usual manner.

| Compound 7 | 5 mg |
|---|---|
| Lactose | 280 mg |

Industrial Applicability

The present invention provides steroid sulfatase inhibitors comprising, as the active ingredient, an estra-1,3,5(10)-triene derivative or a pharmaceutically acceptable salt thereof. The present invention also provides estra-1,3,5(10)-triene derivatives or pharmaceutically acceptable salts thereof that have inhibitory activity against steroid sulfatase and are useful for treating or preventing steroid hormone-dependent diseases.

What is claimed is:

1. A method for inhibiting steroid sulfatase, which comprises administering, to a patient in need thereof, a therapeutically effective amount of an estra-1,3,5(10)-triene derivative which is represented by formula (I):

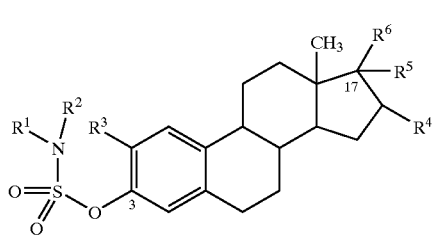

<wherein $R^1$ and $R^2$ are the same or different and represent a hydrogen atom or a lower alkyl group, or $R^1$ and $R^2$ are combined with N adjacent thereto to form a nitrogen-containing heterocyclic group;

$R^3$ represents a hydrogen atom;

$R^4$ represents a hydrogen atom, or is combined with $R^5$ to form a bond;

$R^5$ represents hydrogen atom, or is combined with $R^4$ to form a bond, or is combined with $R^6$ to form $=CR^7R^8$ <wherein $R^7$ represents a hydrogen atom or a substituted or unsubstituted lower alkyl group; $R^8$ represents $COR^9$ {wherein $R^9$ represents a hydrogen atom, a substituted or unsubstituted lower alkyl group, a substituted or unsubstituted lower cycloalkyl group, a substitute or unsubstituted aryl group, a substituted or unsubstituted heterocyclic group, or $OR^{10}$ (wherein $R^{10}$ represents a substituted or unsubstituted aryl group, or a substituted or unsubstituted heterocyclic group)}, $X^1NR^{11}R^{12}$ <wherein $R^{11}$ and $R^{12}$ are the same or different and represent a hydrogen atom, a substituted or unsubstituted lower alkyl group, a substitute or unsubstituted lower cycloalkyl group, a substituted or unsubstituted aryl group, a substituted or unsubstituted heterocyclic group, $OR^{13}$ (wherein $R^{13}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group), or $NR^{14}R^{15}$ {wherein $R^{14}$ and $R^{15}$ are the same or different and represent a hydrogen atom, a substituted or unsubstituted lower alkyl group, a substitute or unsubstituted lower cycloalkyl group, a substituted or unsubstituted aryl group, a substituted or unsubstituted heterocyclic group, $COR^{16}$ (wherein $R^{16}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group), or $SO_2R^{17}$ (wherein $R^{17}$ represents a substituted or unsubstituted lower alkyl group, a substituted or unsubstituted lower cycloalkyl group, a substituted or unsubstituted aryl group, or a substituted or unsubstituted heterocyclic group)}, and $X^1$ represents $C=O$ or $C=S>$, $CSR^{18}$ (wherein $R^{18}$ represents a substituted or unsubstituted heterocyclic group), a substituted or unsubstituted aryl group, a substituted or unsubstituted heterocyclic group, $CR^{19}R^{20}(OH)$ (wherein $R^{19}$ and $R^{20}$ are the same or different and represent a hydrogen atom, a substituted or unsubstituted lower alkyl group, a substituted or unsubstituted lower cycloalkyl group, a substituted or unsubstituted aryl group, or a substituted or unsubstituted heterocyclic group), or $CHR^{21}R^{22}$ <wherein $R^{21}$ represents a hydrogen atom, a substituted or unsubstituted lower alkyl group, substituted or unsubstituted lower cycloalkyl group, a substituted or unsubstituted aryl group, or a substituted or unsubstituted heterocyclic group, $R^{22}$ represents a substituted or unsubstituted aryl group, a substituted or unsubstituted heterocyclic group, or $NR^{23}R^{24}$ {wherein $R^{23}$ and $R^{24}$ are the same or different and represent a hydrogen atom, a substituted or unsubstituted lower alkyl group, a substituted or unsubstituted lower cycloalkyl group, a substituted or unsubstituted aryl group, a substituted or unsubstituted heterocyclic group, $X^2R^{25}$ (wherein $R^{25}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group, and $X^2$ represents $C=O$ or $C=S$), $CO_2R^{26}$ (wherein $R^{26}$ represents a substituted or unsubstituted lower alkyl group, a substituted or unsubstituted lower cycloalkyl group, a substituted or unsubstituted aryl group, or a substituted or unsubstituted heterocyclic group), $X^3NR^{27}R^{28}$ (wherein $R^{27}$ and $R^{28}$ are the same or different and represent a hydrogen atom, a substituted or unsubstituted lower alkyl group, a substituted or unsubstituted lower cycloalkyl group, a substituted or unsubstituted aryl group, or a substituted or unsubstituted heterocyclic group, and $X^3$ represents $C=O$ or $C=S$), or $SO_2R^{29}$ (wherein $R^{29}$ represents an amino group, a mono or di(lower alkyl)amino group, a substituted or unsubstituted lower alkyl group, a substituted or unsubstituted lower cycloalkyl group, a substituted or unsubstituted aryl group, or a substituted or unsubstituted heterocyclic group)}>>;

$R^6$ represents
1) a cyano group,
2) an amino group,
3) $CHR^{30}R^{31}$ <wherein $R^{30}$ represents a hydrogen atom, or a substituted or unsubstituted lower alkyl group, $R^{31}$ represents $COR^{32}$ {wherein $R^{32}$ represents a hydrogen atom, a substituted or unsubstituted lower alkyl group, a substituted or unsubstituted lower cycloalkyl group, a substituted or unsubstituted aryl group, a substituted or unsubstituted heterocyclic group, or $OR^{33}$ (wherein $R^{33}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group)}, $X^4NR^{34}R^{35}$ <wherein $R^{34}$ and $R^{35}$ are the same or different and represent a hydrogen atom, a substituted or unsubstituted lower alkyl group, a substituted or unsubstituted lower cycloalkyl group, a substituted or unsubstituted aryl group, a substituted or unsubstituted heterocyclic group, $OR^{36}$ (wherein $R^{36}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group), or $NR^{37}R^{38}$ {wherein $R^{37}$ and $R^{38}$ are the same or different and represent a hydrogen atom, a substituted or unsubstituted lower alkyl group, a substituted or unsubstituted lower cycloalkyl group, a substituted or unsubstituted aryl group, a substituted or unsubstituted heterocyclic group, $COR^{39}$ (wherein $R^{39}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group), or $SO_2R^{40}$ (wherein $R^{40}$ represents a substituted or unsubstituted lower alkyl group, a substituted or unsubstituted lower cycloalkyl group, a substituted or unsubstituted aryl group, or a substituted or unsubstituted heterocyclic group)}, and $X^4$ represents C=O or C=S>, $CSR^{41}$ (wherein $R^{41}$ represents a substituted or unsubstituted heterocyclic group), $CR^{42}R^{43}$(OH) (wherein $R^{42}$ and $R^{43}$ have the same meanings as defined for $R^{19}$ and $R^{20}$ above, respectively), or $CHR^{44}R^{45}$ (wherein $R^{44}$ and $R^{45}$ have the same meanings as defined for $R^{21}$ and $R^{22}$ above, respectively)>, 4) $COR^{53}$ <wherein $R^{53}$ represents a substituted lower alkyl group, a substituted lower cycloalkyl group, a substituted or unsubstituted aryl group, a substituted or unsubstituted heterocyclic group, $OR^{54}$ (wherein $R^{54}$ represents a substituted lower alkyl group, a substituted or unsubstituted lower cycloalkyl group, a substituted or unsubstituted aryl group, or a substituted or unsubstituted heterocyclic group), or $NR^{55}R^{56}$ <wherein $R^{55}$ represents a hydrogen atom, a substituted or unsubstituted lower alkyl group, a substituted or unsubstituted lower cycloalkyl group, a substituted or unsubstituted aryl group, a substituted or unsubstituted heterocyclic group, or $OR^{57}$ (wherein $R^{57}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group), and $R^{56}$ represents a substituted lower alkyl group, a substituted or unsubstituted lower cycloalkyl group, a substituted or unsubstituted aryl group, a substituted or unsubstituted heterocyclic group, $OR^{58}$ (wherein $R^{58}$ represents a substituted lower alkyl group, a substituted or unsubstituted lower cycloalkyl group, a substituted or unsubstituted aryl group, or a substituted or unsubstituted heterocyclic group), or $NR^{59}R^{60}$ {wherein $R^{59}$ and $R^{60}$ are the same or different and represent a hydrogen atom, a substituted or unsubstituted lower alkyl group, a substituted or unsubstituted lower cycloalkyl group, a substituted or unsubstituted aryl group, a substituted or unsubstituted heterocyclic group, $COR^{61}$ (wherein $R^{61}$ represents hydrogen atom, a substituted or unsubstituted lower alkyl group, a substituted or unsubstituted lower cycloalkyl group, a substituted or unsubstituted aryl group, or a substituted or unsubstituted heterocyclic group), or $SO_2R^{62}$ (wherein $R^{62}$ represents a substituted or unsubstituted lower alkyl group, a substituted or unsubstituted lower cycloalkyl group, a substituted or unsubstituted aryl group, or a substituted or unsubstituted heterocyclic group)}>>, 5) $CSR^{63}$ {wherein $R^{63}$ represents a substituted or unsubstituted heterocyclic group, or $NR^{64}R^{65}$ (wherein $R^{64}$ and $R^{65}$ have the same meanings as defined for $R^{34}$ and $R^{35}$ above, respectively)}, 6) a substituted or unsubstituted aryl group, 7) a substituted or unsubstituted heterocyclic group, 8) $CR^{71}R^{72}$(OH) (wherein $R^{71}$ represents a hydrogen atom, a substituted or unsubstituted lower alkyl group a substituted or unsubstituted lower cycloalkyl group, a substituted or unsubstituted aryl group, or a substituted or unsubstituted heterocyclic group, and $R^{72}$ represents a substituted or unsubstituted lower alkyl group, a substituted or unsubstituted lower cycloalkyl group, a substituted or unsubstituted aryl group, or a substituted or unsubstituted heterocyclic group), 9) $CHR^{73}R^{74}$ (wherein $R^{73}$ and $R^{74}$ have the same meanings as defined for $R^{21}$ and $R^{22}$ above, respectively), 10) $NR^{82}R^{83}$ {wherein $R^{82}$ represents a hydrogen atom, a substituted or unsubstituted lower alkyl group a substituted or unsubstituted lower cycloalkyl group, a substituted or unsubstituted aryl group, or a substituted or unsubstituted heterocyclic group, and $R^{83}$ represents a substituted or unsubstituted lower alkyl group, a substituted or unsubstituted lower cycloalkyl group, a substituted or unsubstituted aryl group, a substituted or unsubstituted heterocyclic group, $COR^{84}$ (wherein $R^{84}$ represents a substituted lower alkyl group, a substituted or unsubstituted lower cycloalkyl group, a substituted or unsubstituted aryl group, or a substituted or unsubstituted heterocyclic group), $CSR^{85}$ (wherein $R^{85}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group), $CO_2R^{86}$ (wherein $R^{86}$ represents a substituted or unsubstituted lower alkyl group, a substituted or unsubstituted lower cycloalkyl group, a substituted or unsubstituted aryl group, or a substituted or unsubstituted heterocyclic group), $X^9NR^{87}R^{88}$ (wherein $R^{87}$ and $R^{88}$ are the same or different and represent a hydrogen atom, a substituted or unsubstituted lower alkyl group, a substituted or unsubstituted lower cycloalkyl group, a substituted or unsubstituted aryl group, or a substituted or unsubstituted heterocyclic group, and $X^9$ represents C=O or C=S), or $SO_2R^{89}$ (wherein $R^{89}$ represents an amino group, a mono or di(lower alkyl)amino group, a substituted or unsubstituted lower alkyl group, a substituted or unsubstituted lower cycloalkyl group, a substituted or unsubstituted aryl group, or a substituted or unsubstituted heterocyclic group)}, or 11) $NR^{90}COR^{91}$ (wherein $R^{90}$ represents a substituted lower alkyl group, a substituted or unsubstituted lower cycloalkyl group, a substituted or unsubstituted aryl group, or a substituted or unsubstituted heterocyclic group, and $R^{91}$ represents a hydrogen atom or a lower alkyl group), or 12) $R^6$ is combined with $R^5$ to form =$CR^7R^8$ (wherein $R^7$ and $R^8$ have the same meanings as defined above, respectively)>, or a pharmaceutically acceptable salt thereof.

2. An estra-1,3,5(10)-triene derivative which is represented by formula (1A):

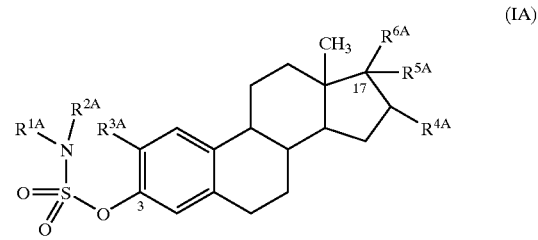

(IA)

<wherein $R^{1A}$ and $R^{2A}$ are the same or different and represent a hydrogen atom or a lower alkyl group, or $R^{1A}$ and $R^{2A}$ are combined with N adjacent thereto to form a nitrogen-containing heterocyclic group; $R^{3A}$ represents a hydrogen atom and $R^{4A}$ represents a hydrogen atom, or is combined with $R^{5A}$ to form a bond, and;

(1) when $R^{4A}$ is a hydrogen atom, $R^{5A}$ is a hydrogen atom, or is combined with $R^{6A}$ to form =$CR^{7A1}R^{8A1}$ {wherein $R^{7A1}$ represents a hydrogen atom or a substituted or unsubstituted lower alkyl group, $R^{8A1}$ represents $COR^{9A1}$ {wherein $R^{9A1}$ represents a hydrogen atom, a substituted or unsubstituted lower alkyl group, a substituted or unsubstituted lower cycloalkyl group, a substituted or unsubstituted aryl group, a substituted or unsubstituted heterocyclic group or $OR^{10}$ (wherein $R^{10}$ represents a substituted or unsubstituted aryl group or a substituted or unsubstituted heterocyclic group}}, $X^{1A1}NR^{11A1}R^{12A1}$ (wherein $R^{11A1}$ and $R^{12A1}$ are the same or different and represent a hydrogen atom, a substituted or unsubstituted lower alkyl group, a substituted or unsubstituted lower cycloalkyl group, a substituted or unsubstituted aryl group, a substituted or unsubstituted heterocyclic group, $OR^{13}$ (wherein $R^{13}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group), or $NR^{14}R^{15}$ {wherein $R^{14}$ and $R^{15}$ are the same or different and represent a hydrogen atom, a substituted or unsubstituted lower alkyl group, a substituted or unsubstituted lower cycloalkyl group, a substituted or unsubstituted aryl group, a substituted or unsubstituted heterocyclic group, $COR^{16}$ (wherein $R^{16}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group), or $SO_2R^{17}$ (wherein $R^{17}$ represents a substituted or unsubstituted lower alkyl group, a substituted or unsubstituted lower cycloalkyl group, a substituted or unsubstituted aryl group, or a substituted or unsubstituted heterocyclic group)}, and $X^{1A1}$ represents C=O or C=S>), $CSR^{18A1}$ (wherein $R^{18A1}$ represents a substituted or unsubstituted heterocyclic group), $CR^{19A1}R^{20A1}(OH)$ (wherein $R^{19A1}$ and $R^{20A1}$ are the same or different and represent a hydrogen atom, a substituted or unsubstituted lower alkyl group, a substituted or unsubstituted lower cycloalkyl group, a substituted or unsubstituted aryl group, or a substituted or unsubstituted heterocyclic group), or $CHR^{21A1}R^{22A1}$ (wherein $R^{21A1}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group, and $R^{22A1}$ represents a substituted or unsubstituted aryl group, a substituted or unsubstituted heterocyclic group, or $NR^{23}R^{24}$ {wherein $R^{23}$ and $R^{24}$ are the same or different and represent a hydrogen atom, a substituted or unsubstituted lower alkyl group, a substituted or unsubstituted lower cycloalkyl group, a substituted or unsubstituted aryl group, a substituted or unsubstituted heterocyclic group, $X^2R^{25}$ (wherein $R^{25}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group, and $X^2$ represents C=O or C=S), $CO_2R^{26}$ (wherein $R^{26}$ represents a substituted or unsubstituted lower alkyl group, a substituted or unsubstituted lower cycloalkyl group, a substituted or unsubstituted aryl group, or a substituted or unsubstituted heterocyclic group), $X^3NR^{27}R^{28}$ (wherein $R^{27}$ and $R^{28}$ are the same or different and represent a hydrogen atom, a substituted or unsubstituted lower alkyl group, a substituted or unsubstituted lower cycloalkyl group, a substituted or unsubstituted aryl group aryl, or a substituted or unsubstituted heterocyclic group, and $X^3$ represents C=O or C=S), or $SO_2R^{29}$ (wherein $R^{29}$ represents an amino group, a mono or di(lower alkyl)amino group, a substituted or unsubstituted lower alkyl group, a substituted or unsubstituted lower cycloalkyl group, a substituted or unsubstituted aryl group, or a substituted or unsubstituted heterocyclic group)};

$R^{6A}$ represents a cyano group, an amino group, $CHR^{30A1}R^{31A1}$ <wherein $R^{30A1}$ represents a hydrogen atom or a substituted or unsubstituted lower alkyl group, $R^{31A1}$ represents $COR^{32A1}$ (wherein $R^{32A1}$ represents a hydrogen atom, a substituted or unsubstituted lower alkyl group, a substituted or unsubstituted lower cycloalkyl group, a substituted or unsubstituted aryl group, a substituted or unsubstituted heterocyclic group, or $OR^{33}$ (wherein $R^{33}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group)}), $X^{4A1}NR^{34A1}R^{35A1}$ (wherein $R^{34A1}$ and $R^{35A1}$ are the same or different and represent a hydrogen atom, a substituted or unsubstituted lower alkyl group, a substituted or unsubstituted lower cycloalkyl group, a substituted or unsubstituted aryl group, a substituted or unsubstituted heterocyclic group, $OR^{36}$ (wherein $R^{36}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group), $NR^{37}R^{38}$ {wherein $R^{37}$ and $R^{38}$ are the same or different and represent a hydrogen atom, a substituted or unsubstituted lower alkyl group, a substituted or unsubstituted lower cycloalkyl group, a substituted or unsubstituted aryl group, a substituted or unsubstituted heterocyclic group, $COR^{39}$ (wherein $R^{39}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group, or $SO_2R^{40}$ (wherein $R^{40}$ represents a substitute or unsubstituted lower alkyl group, a substituted or unsubstituted lower cycloalkyl group, a substituted or unsubstituted aryl group, or a substituted or unsubstituted heterocyclic group)}, and $X^{4A1}$ represents C=O or C=S>, $CSR^{41A1}$ (wherein $R^{41A1}$ represents a substituted or unsubstituted heterocyclic group), or $CHR^{44A1}R^{45A1}$ <wherein $R^{44A1}$ has the same meaning as defined for $R^{21A1}$ above, $R^{45A1}$ represents $NR^{46A1}R^{47A1}$ {wherein $R^{46A1}$ has the same meaning as defined for $R^{23}$ above, $R^{47A1}$ represents $CSR^{48A1}$ (wherein $R^{48A1}$ has the same meaning as defined for $R^{25}$ above), $CO_2R^{49A1}$ (wherein $R^{49A1}$ has the same meaning as defined for $R^{26}$ above), $X^{6A1}NR^{50A1}R^{51A1}$ (wherein $R^{50A1}$, $R^{51A1}$ and $X^{6A1}$ have the same meanings as defined for $R^{27}$, $R^{28}$ and $X^3$ above, respectively) or $SO_2R^{52A1}$ (wherein $R^{52A1}$ has the same meaning as defined for $R^{29}$ above)}>>, $COR^{53A1}$ (wherein $R^{53A1}$ represents a substituted lower alkyl group, a substituted lower cycloalkyl group, a substituted or unsubstituted aryl group, a substituted or unsubstituted heterocyclic group, $OR^{54}$ (wherein $R^{54}$ represents a substituted lower alkyl group, a substituted or unsubstituted lower cycloalkyl group, a substituted or unsubstituted aryl group, or a substituted or unsubstituted heterocyclic group), or $NR^{55}R^{56}$ <wherein $R^{55}$ represents a hydrogen atom, a substituted or unsubstituted lower alkyl group, a substituted or unsubstituted lower cycloalkyl group, a substituted or unsubstituted aryl group, a substituted or unsubstituted heterocyclic group, or $OR^{57}$ (wherein $R^{57}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group, and $R^{56}$ represents a substituted lower alkyl group, a substituted or unsubstituted lower cycloalkyl group, a substituted or unsubstituted aryl group, a substituted or unsubstituted heterocyclic group, $OR^{58}$ (wherein $R^{58}$ represents a substituted lower alkyl group, a substituted or unsubstituted lower cycloalkyl group, a substituted or unsubstituted aryl group, or a substituted or unsubstituted heterocyclic group), or $NR^{59}R^{60}$ {wherein $R^{59}$ and $R^{60}$ are the same or different and represent a hydrogen atom, a substituted or unsubstituted lower alkyl group, a substituted or unsubstituted lower cycloalkyl group, a substituted or unsubstituted aryl group, a substituted or unsubstituted heterocyclic group, $COR^{61}$ (wherein $R^{61}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group), or $SO_2R^{62}$ (wherein $R^{62}$ represents a substituted or unsubstituted lower alkyl group, a substituted or unsubstituted lower cycloalkyl group, a substituted or unsubstituted aryl group, or a substituted or unsubstituted heterocyclic group)}>>), $CSR^{63A1}$ (wherein $R^{63A1}$ represents a substituted or unsubstituted heterocyclic group or $NR^{64}R^{65}$ (wherein $R^{64}$ and $R^{65}$ have the same meanings as defined for $R^{34A1}$ and $R^{35A1}$ above, respectively), $CR^{71A1}R^{72A1}(OH)$ (wherein $R^{71A1}$ represents hydrogen atom, a substituted or unsubstituted lower alkyl group, a substituted or unsubstituted lower cycloalkyl group, a substituted or unsubstituted aryl group, or a substituted or unsubstituted heterocyclic group, and $R^{72A1}$ represents a substituted or unsubstituted lower alkyl group, a substituted or unsubstituted lower cycloalkyl group, a substituted or unsubstituted aryl group, or a substituted or unsubstituted heterocyclic group), $CHR^{73A1}NR^{75A1}R^{76A1}$ (wherein $R^{73A1}$, $R^{75A1}$ and $R^{76A1}$ have the same meanings as defined for $R^{21A1}$, $R^{23}$ and $R^{24}$ above, respectively), $NR^{82A1}R^{83A1}$ (wherein $R^{82A1}$ has the same meaning as defined for $R^{71A1}$ above, and $R^{83A1}$ represents a substituted or unsubstituted lower alkyl group, a substituted or unsubstituted lower cycloalkyl group, a substituted or unsubstituted aryl group, or a substituted or unsubstituted heterocyclic group, $COR^{84}$ (wherein $R^{84}$ represents a substituted lower alkyl group, a substituted or unsubstituted lower cycloalkyl group, a substituted or unsubstituted aryl group, or a substituted or unsubstituted heterocyclic group), $CSR^{85}$ (wherein $R^{85}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group), $CO_2R^{86}$ (wherein $R^{86}$ represents a substituted or unsubstituted lower alkyl group, a substituted or unsubstituted lower cycloalkyl group, a substituted or unsubstituted aryl group, or a substituted or unsubstituted heterocyclic group), $X^9NR^{87}R^{88}$ (wherein $R^{87}$ and $R^{88}$ are the same or different and represent a hydrogen atom, a substituted or unsubstituted lower alkyl group, a substituted or unsubstituted lower cycloalkyl group, a substituted or unsubstituted aryl group, or a substituted or unsubstituted heterocyclic group, and $X^9$ represents C=O or C=S), or $SO_2R^{89}$ (wherein $R^{89}$ represents an amino group, a mono or di(lower alkyl)amino group, a substituted or unsubstituted lower alkyl group, a substituted or unsubstituted lower cycloalkyl group, a substituted or unsubstituted aryl group or a substituted or unsubstituted heterocyclic group), or $NR^{90A1}COR^{91A1}$ (wherein $R^{90A1}$ represents a substituted lower alkyl group, a substituted or unsubstituted lower cycloalkyl group, a substituted or unsubstituted aryl group, or a substituted or unsubstituted heterocyclic group, and $R^{91A1}$ represents a hydrogen atom or a lower alkyl group), or $R^{6A}$ is combined with $R^{5A}$ to form $=CR^{7A1}R^{8a1}$; and (2) when $R^{4A}$ is combined with $R^{5A}$ to form a bond, $R^{6A}$ represents a cyano group, $CHR^{30A2}R^{31A2}$ {wherein $R^{30A2}$ has the same meaning as defined for $R^{30A1}$ above, and $R^{31A2}$ represents $COR^{32}$ (wherein $R^{32}$ has the same meaning as defined for $R^{32A1}$), $X^4NR^{34}R^{35}$ (wherein $X^4$, $R^{34}$ and $R^{35}$ have the same meaning as defined for $X^{4A1}$, $R^{34A1}$ and $R^{35A1}$, respectively), $CSR^{41}$ (wherein $R^{41}$ has the same meaning as defined for $R^{41A1}$), $CR^{42}R^{43}(OH)$ (wherein $R^{42}$ and $R^{43}$ have the same meanings as defined for $R^{19A1}$ and $R^{20A1}$, respectively), or $CHR^{44}R^{45}$ (wherein $R^{44}$ and $R^{45}$ have the same meanings as defined for $R^{21A1}$ and $R^{22A1}$, respectively)}, $COR^{53A2}$ (wherein $R^{53A2}$ has the same meaning as defined for $R^{53A1}$ above), $CSR^{63A2}$ (wherein $R^{63A2}$ has the same meaning as defined for $R^{63A1}$ above), a substituted or unsubstituted aryl group, a substituted or unsubstituted heterocyclic group, $CR^{71A2}R^{72A2}(OH)$ (wherein $R^{71A2}$ and $R^{72A2}$ have the same meanings as defined for $R^{71A1}$ and $R^{72A1}$ above, respectively), $CHR^{73A2}R^{74A2}$ (wherein $R^{73A2}$ and $R^{74A2}$ have the same meanings as defined for $R^{21A1}$ and $R^{22A1}$ above, respectively), $NR^{82A2}R^{83A2}$ (wherein $R^{82A2}$ and $R^{83A2}$ have the same meanings as defined for $R^{82A1}$ and $R^{83A1}$ above, respectively), or $NR^{90A2}COR^{91A2}$ (wherein $R^{90A2}$ and $R^{91A2}$ have the same meanings as defined for $R^{90A1}$ and $R^{91A1}$ above, respectively)>, or a pharmaceutically acceptable salts thereof.

3. The estra-1,3,5(10)-triene derivative or the pharmaceutically acceptable salt thereof according to claim 2, wherein $R^{4A}$ is a hydrogen atom, and $R^{5A}$ and $R^{6A}$ are combined to form $=CR^{7A1}R^{8A1}$.

4. The estra-1,3,5(10)-triene derivative or the pharmaceutically acceptable salt thereof according to claim 3, wherein $R^{8A1}$ is $COR^{9A3}$ (wherein $R^{9A3}$ is a substituted or unsubstituted heterocyclic group), $X^{1A1}NR^{11A1}R^{12A1}$, or $CSR^{18A1}$.

5. The estra-1,3,5(10)-triene derivative or the pharmaceutically acceptable salt thereof according to claim 2, wherein $R^{4A}$ and $R^{5A}$ are hydrogen atoms.

6. The estra-1,3,5(10)-triene derivative or the pharmaceutically acceptable salt thereof according to claim 5, wherein $R^{6A}$ is $CHR^{30A1}R^{31A3}$ {$R^{31A3}$ represents $X^{4A1}NR^{34A1}R^{35A1}$ or $CSR^{41A1}$, $COR^{53A1}$, $CSR^{63A1}$, $NR^{82A1}R^{83A1}$ or $NR^{90A1}COR^{91A1}$.

7. The estra-1,3,5(10)-triene derivative or the pharmaceutically acceptable salt thereof according to claim 2, wherein $R^{4A}$ and $R^{5A}$ are combined to form a bond, and $R^{6A}$ is a cyano group, $CHR^{30A2}R^{31A2}$, $COR^{53A2}$, $CSR^{63A2}$, a substituted or unsubstituted aryl group, a substituted or unsubstituted heterocyclic group, $CR^{71A2}R^{72A2}(OH)$, $CHR^{73A2}R^{74A2}$, $NR^{82A2}R^{83A2}$, or $NR^{90A2}COR^{91A2}$.

8. The estra-1,3,5(10)-triene derivative or the pharmaceutically acceptable salt thereof according to claim 7, wherein $R^{6A}$ is $COR^{53A3}$ [wherein $R^{53A3}$ is a substituted or unsubstituted aryl group, a substituted or unsubstituted heterocyclic group, $OR^{54A1}$ (wherein $R^{54A1}$ represents a substituted lower alkyl group, a substituted or unsubstituted lower cycloalkyl group, a substituted or unsubstituted aryl group, or a substituted or unsubstituted heterocyclic group, or $NR^{55A1}R^{56A1}$ {wherein $R^{55A1}$ represents a hydrogen atom, a substituted or unsubstituted lower alkyl group, a substituted or unsubstituted lower cycloalkyl group, a substituted or unsubstituted aryl group, a substituted or unsubstituted heterocyclic group, or $OR^{57}$ (wherein $R^{57}$ represents a hydrogen atom, a substituted or unsubstituted lower alkyl group, substituted or unsubstituted lower cycloalkyl group, a substituted or unsubstituted aryl group, or substituted or unsubstituted heterocyclic group), $R^{56A1}$ represents a substituted lower alkyl group, a substituted or unsubstituted lower cycloalkyl group, a substituted or unsubstituted aryl group, a substituted or unsubstituted heterocyclic group, $OR^{58}$ (wherein $R^{58}$ represents a substituted lower alkyl group, a substituted or unsubstituted lower cycloalkyl group, a substituted or unsubstituted aryl group, a substituted or unsubstituted heterocyclic group) or $NR^{51}R^{60}$ [wherein $R^{51}$ and $R^{60}$ are the same or different and represent a hydrogen atom, a substituted or unsubstituted lower alkyl group, a substituted or unsubstituted lower cycloalkyl group, a substituted or unsubstituted aryl group, a substituted or unsubstituted heterocyclic group, $COR^{61}$ (wherein $R^{61}$ represents a hydrogen atom, a substituted or unsubstituted lower alkyl group, a substituted or unsubstituted lower cycloalkyl group, a substituted or unsubstituted aryl group, or a substituted or unsubstituted heterocyclic group) or $SO_2R^{62}$ (wherein $R^{62}$ represents a substituted or unsubstituted lower alkyl group, a substituted or unsubstituted lower cycloalkyl group, a substituted or unsubstituted aryl group, or a substituted or unsubstituted heterocyclic group)]})], $CSR^{63A2}$, a substituted or unsubstituted aryl group, a substituted or unsubstituted heterocyclic group, or $CR^{71A2}R^{72A2}(OH)$.

9. The estra-1,3,5(10)-triene derivative or the pharmaceutically acceptable salt thereof according to any one of claims 2 to 8, wherein $R^{34}$ is a hydrogen atom.

10. The estra-1,3,5(10)-triene derivative or the pharmaceutically acceptable salt thereof according to any one of claims 2 to 8, wherein $R^{1A}$, $R^{2A}$ and $R^{3A}$ are hydrogen atoms.

11. A method for treating a steroid sulfatase-related disease, which comprises administering a therapeutically effective amount of the estra-1,3,5(10)-triene derivatives or the pharmaceutically acceptable salt thereof described in claim 1 to patient in need thereof.

12. A method for inhibiting steroid sulfatase, which comprises administering a therapeutically effective amount of the estra-1,3,5(10)-triene derivative or the pharmaceutically acceptable salt thereof according to any one of claims 2 to 8 to a patient in need thereof.

13. A method for treating breast cancer, endometrial cancer, ovarian cancer or prostate cancer, which comprises administering a therapeutically effective amount of the estra-1,3,5(10)-triene derivative or the pharmaceutically acceptable salt thereof according to any one of claims 2 to 8 to a patient in need thereof.

14. A method for treating tumor, which comprises administering a therapeutically effective amount of the estra-1,3,5(10)-triene derivative or the pharmaceutically acceptable salt thereof according to any one of claims 2 to 8 to a patient in need thereof.

15. A method for treating a steroid sulfatase-related disease, which comprises administering a therapeutically effective amount of the estra-1,3,5(10)-triene derivative or the pharmaceutically acceptable salt thereof according to any one of claims 2 to 8 to a patient in need thereof.

16. A method for treating a steroid hormone-dependent disease, which comprises administering a therapeutically effective amount of the estra-1,3,5(10)-triene derivative or the pharmaceutically acceptable salt thereof according to any one of claims 2 to 8 to a patient in need thereof.

17. A method for treating a steroid hormone-dependent disease, which comprises administering a therapeutically effective amount of the estra-1,3,5(10)-triene derivative or the pharmaceutically acceptable salt thereof according to any one of claims 2 to 8 which further has an antiestrogen activity to a patient in need thereof.

18. A method for treating a steroid hormone-dependent disease, which comprises administering a therapeutically effective amount of the estra-1,3,5(10)-triene derivative or the pharmaceutically acceptable salt thereof according to any one of claims 2 to 8 which produces a phenol derivative having an antiestrogen activity through hydrolysis of a sulfamate in vivo to a patient in need thereof.

19. A method for treating malignant tumors, which comprises administering therapeutically effective amount of the estra-1,3,5(10)-triene derivative or the pharmaceutically acceptable salt thereof according to any one of claims 2 to 8 to a patient in need thereof.

20. A method for treating an androgen-dependent disease, which comprises administering a therapeutically effective amount of the estra-1,3,5(10)-triene derivative or the pharmaceutically acceptable salt thereof described in claim 1 to a patient in need thereof.

21. A method for treating an androgen-dependent disease, which comprises administering a therapeutically effective amount of the estra-1,3,5(10)-triene derivative or the pharmaceutically acceptable salt thereof according to any one of claims 2 to 8 to a patient in need thereof.

* * * * *

UNITED STATES PATENT AND TRADEMARK OFFICE
CERTIFICATE OF CORRECTION

PATENT NO. : 6,953,785 B2
DATED : October 11, 2005
INVENTOR(S) : Yoji Ino et al.

It is certified that error appears in the above-identified patent and that said Letters Patent is hereby corrected as shown below:

Column 4,
Line 2, "unsubstituted," should read -- unsubstituted --.

Column 5,
Line 6, "NR14R$^{15}$" should read -- NR$^{14}$R$^{15}$ --; and
Line 50, "X$^3$NR$^{27}$R$^{2}$" should read -- X$^3$NR$^{27}$R$^{28}$ --.

Column 10,
Line 67, "effective-amount" should read -- effective amount --.

Column 12,
Line 27, "dif ferent" should read -- different --.

Column 17,
Line 16, "in" should be deleted.

Column 19,
Line 38, "acetone" should read -- acetone, -- and "dichlorometh,ane," should read -- dichloromethane, --.

Column 21,
Line 48, "atmospheric pressure" should read -- atmospheres --.

Column 27,
Line 49, "R$^2$a," should read -- R$^{2a}$, --.

Column 32,
Line 23, "bytreating" should read -- by treating --.

UNITED STATES PATENT AND TRADEMARK OFFICE
CERTIFICATE OF CORRECTION

PATENT NO. : 6,953,785 B2
DATED : October 11, 2005
INVENTOR(S) : Yoji Ino et al.

It is certified that error appears in the above-identified patent and that said Letters Patent is hereby corrected as shown below:

Column 34,
Lines 20-29,

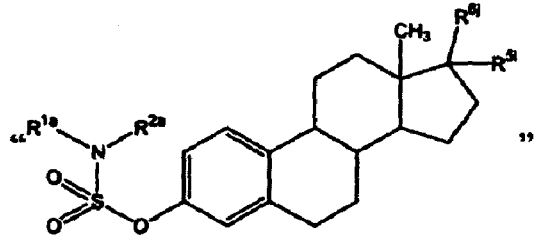

should read

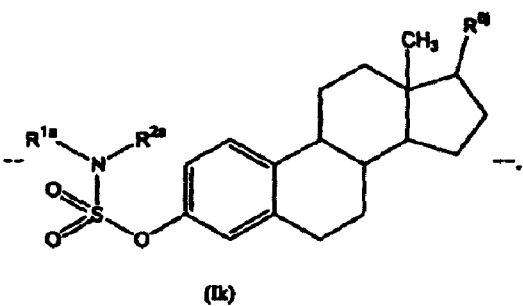

Column 56,
Line 35, "that," should read -- that --.

Column 65,
Line 33, "J 8.9 Hz," should read -- J=8.9 Hz, --.

Column 83,
Line 32, "(brs," should read -- (br s, --; and
Line 59, "(brs," should read -- (br s, --.

Column 90,
Line 62, "heterocvclic" should read -- heterocyclic --.

Column 91,
Lines 6, 18, 32 and 62, "arvl" should read -- aryl --;
Line 14, "heterocvclic" should read -- heterocyclic --; and
Line 28, "heterocv- " should read -- heterocy- --.

UNITED STATES PATENT AND TRADEMARK OFFICE
CERTIFICATE OF CORRECTION

PATENT NO. : 6,953,785 B2
DATED : October 11, 2005
INVENTOR(S) : Yoji Ino et al.

It is certified that error appears in the above-identified patent and that said Letters Patent is hereby corrected as shown below:

Column 92,
Line 1, "aryl group aryl" should read -- aryl group --;
Line 2, "erocvclic" should read -- erocyclic --;
Lines 8, 21, 37 and 46, "heterocvclic" should read -- heterocyclic --; and
Line 31, "heterocv" should read -- heterocy --.

Column 93,
Lines 4, 17, 22, 31 and 33, "heterocvclic" should read -- heterocyclic --;
Line 16, "arvl" should read -- aryl --;
Line 53, "erocvclic" should read -- erocyclic --.

Column 94,
Line 4, "heterocvclic" should read -- heterocyclic --;
Line 43, "salts" should read -- salt --;
Line 58, "{$R^{31A3}$" should read -- {wherein $R^{31A3}$ --; and
Line 59, "or $CSR^{41At}$," should read -- or $CSR^{41A1}$}, --.

Column 96,
Line 38, "administering" should read -- administering a --.

Signed and Sealed this

Twenty-third Day of May, 2006

JON W. DUDAS
*Director of the United States Patent and Trademark Office*